(12) United States Patent
Baday et al.

(10) Patent No.: US 11,338,290 B2
(45) Date of Patent: May 24, 2022

(54) SORTING BIOLOGICAL AND NON-BIOLOGICAL MOIETIES USING MAGNETIC LEVITATION

(71) Applicant: The Board of Trustees of the Leland Stanford Junior University, Stanford, CA (US)

(72) Inventors: Murat Baday, Menlo Park, CA (US); Naside Gozde Durmus, Palo Alto, CA (US); Semih Calamak, Palo Alto, CA (US); Utkan Demirci, Stanford, CA (US); Ronald W. Davis, Palo Alto, CA (US); Lars Steinmetz, San Francisco, CA (US); Jaeyoung Yang, Palo Alto, CA (US); Thiruppathiraja Chinnasamy, Mountain View, CA (US); Alessandro Tocchio, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/764,017

(22) PCT Filed: Sep. 30, 2016

(86) PCT No.: PCT/US2016/054987
§ 371 (c)(1),
(2) Date: Mar. 28, 2018

(87) PCT Pub. No.: WO2017/059353
PCT Pub. Date: Apr. 6, 2017

(65) Prior Publication Data
US 2018/0280977 A1    Oct. 4, 2018

Related U.S. Application Data

(60) Provisional application No. 62/236,692, filed on Oct. 2, 2015.

(51) Int. Cl.
*B01L 3/00* (2006.01)
*B03C 1/32* (2006.01)
(Continued)

(52) U.S. Cl.
CPC ... *B01L 3/502761* (2013.01); *B01L 3/502784* (2013.01); *B03C 1/288* (2013.01);
(Continued)

(58) Field of Classification Search
None
See application file for complete search history.

(56) References Cited

U.S. PATENT DOCUMENTS 6,432,630 B1 * 8/2002 Blankenstein ......... B01D 57/02
                                                         435/4
9,517,474 B2 * 12/2016 Mao ......................... B03C 1/32
(Continued)

FOREIGN PATENT DOCUMENTS

CN    103403557    11/2013
EP    0925494      6/1999
(Continued)

OTHER PUBLICATIONS

Microfluidic pumps—types, accuracy and applications, Elveflow, Accessed Aug. 19, 2021, https://www.elveflow.com/microfluidic-reviews/microfluidic-flow-control/high-accuracy-microfluidic-pumps/, pp. 1-12. (Year: 2021).*
(Continued)

*Primary Examiner* — David C Mellon
(74) *Attorney, Agent, or Firm* — Quarles & Brady LLP

(57) ABSTRACT

Systems and methods for levitating populations of moieties, cells, or other such units using one or more magnets in a microfluidic environment are provided. These systems and methods may be used to, for example, separate or sort heterogeneous populations of the units from one another, to
(Continued)

assembly a multi-unit assembly during the levitating of the units, and to evaluate samples at the point of care in real-time. These systems and methods may also utilize a frame that enables an imaging device, such as a smartphone, to capture the units in real time as they are manipulated in the system.

19 Claims, 39 Drawing Sheets

(51) Int. Cl.
    G01N 33/569    (2006.01)
    G01N 33/574    (2006.01)
    G01N 33/543    (2006.01)
    B03C 1/28      (2006.01)
    G01N 15/14     (2006.01)
    G01N 33/487    (2006.01)
    G16H 30/40     (2018.01)
    G06T 7/00      (2017.01)

(52) U.S. Cl.
    CPC ............... *B03C 1/32* (2013.01); *G01N 15/14* (2013.01); *G01N 33/4875* (2013.01); *G01N 33/54366* (2013.01); *G01N 33/56966* (2013.01); *G01N 33/574* (2013.01); *G06T 7/0016* (2013.01); *G16H 30/40* (2018.01); *B01L 2200/0652* (2013.01); *B01L 2300/0864* (2013.01); *B01L 2400/043* (2013.01); *B03C 2201/18* (2013.01); *B03C 2201/26* (2013.01); *G01N 2015/1486* (2013.01); *G06T 2207/30101* (2013.01); *G06T 2207/30242* (2013.01); *G06T 2211/428* (2013.01)

(56) References Cited

U.S. PATENT DOCUMENTS

| | | | |
|---|---|---|---|
| 2002/0187072 A1 | 12/2002 | Karp | |
| 2003/0095897 A1 | 5/2003 | Grate et al. | |
| 2008/0074449 A1 | 3/2008 | Lee et al. | |
| 2010/0285606 A1 | 11/2010 | Phillips et al. | |
| 2012/0080360 A1* | 4/2012 | Stone | B03C 1/288 209/214 |
| 2012/0122731 A1 | 5/2012 | Soh et al. | |
| 2013/0130226 A1 | 5/2013 | Lim et al. | |
| 2013/0133419 A1 | 5/2013 | Whitesides et al. | |
| 2013/0306566 A1* | 11/2013 | Mao | C12N 13/00 210/695 |
| 2014/0220617 A1 | 8/2014 | Yung et al. | |
| 2014/0248618 A1 | 9/2014 | Shaikh et al. | |
| 2016/0370386 A1* | 12/2016 | Demirci | G01N 33/574 |

FOREIGN PATENT DOCUMENTS

| | | |
|---|---|---|
| EP | 1916032 A1 | 4/2008 |
| JP | 2008119678 A | 5/2008 |
| JP | 2011185839 A | 9/2011 |
| JP | 2012159337 A | 8/2012 |
| JP | 2014182778 A | 9/2014 |
| WO | 9810267 A1 | 3/1998 |
| WO | 2008051189 A2 | 5/2008 |
| WO | 2010144745 A2 | 12/2010 |
| WO | 2014004577 A1 | 1/2014 |
| WO | 2015058206 A1 | 4/2015 |
| WO | 2015130913 A1 | 9/2015 |

OTHER PUBLICATIONS

Russian Federal Service for Intellectual Property, Search Report and Official Notification, Application No. 2018116084, dated Feb. 26, 2020, 8 pages.
European Patent Office, Extended Search Report, Application No. 168527798.6, dated May 2, 2019, 10 pages.
PCT International Search Report and Written Opinion, PCT/US2016/054987, dated Feb. 16, 2017, 14 pages.
Benkebil, et al., Diagnostic Accuracy of a New Point-of-Care Screening Assay for Celiac Disease, World Journal of Gastroenterology, 2013, 19(31):5111-5117.
Breslauer, et al., Mobile Phone Based Clinical Microscopy for Global Health Applications, PLoS ONE, 2009, 4(7):e6320, 7 pages.
Briggs, et al., Continuing Developments with the Automated Platelet Count, International Journal of Laboratory Hematology, 2007, 29:77-91.
Bwambok, et al., Paramagnetic Ionic Liquids for Measurements of Density Using Magnetic Levitation, Analytical Chemistry, 2013, 85:8442-8447.
Cheng, et al., Cell Detection and Counting Through Cell Lysate Impedance Spectroscopy in Microfluidic Devices, Lab an a Chip, 2007, 7(6):746-755.
Glynn, et al., CD4 Counting Technologies for HIV Therapy Monitoring in Resource-Poor Settings—State-of-the-art and Emerging Microtechnologies, Lab on a Chip, 2013, 13:2731-2748.
Grenvall, et al., Two-Dimensional Acoustic Particle Focusing Enables Sheathless Chip Coulter Counter with Planar Electrode Configuration, Lab on a Chip, 2014, 14(24):4629-4637.
Heikali, et al., A Niche for Microfluidics in Portable Hematology Analyzers, JALA, 2010, 15:319-328.
Huh, et al., Microfluidics for Flow Cytometric Analysis of Cells and Particles, Physiological Measurement, 2005, 26:R73-R98.
Inci, et al., Nanoplasmonic Quantitative Detection of Intact Viruses from Unprocessed Whole Blood, ACS Nano, 2013, 7(6):4733-4745.
Inglis, et al., Microfluidic High Gradient Magnetic Cell Separation, Journal of Applied Physics, 2006, 99:08K101, 3 pages.
Kallander, et al., Mobile Health (mHealth) Approaches and Lessons for Increased Performance and Retention of Community Health Workers in Low- and Middle-Income Countries: A Review, Journal of Medical Internet Research, 2013, 15(1):e17, 13 pages.
Lockett, et al., Analyzing Forensic Evidence Based on Density with Magnetic Levitation, Journal of Forensic Sciences, 2013, 58(1):40-45.
Lu, et al., Low Cost, Portable Detection of Gold Nanoparticle-labeled Microfluidic Immunoassay with Camera Cell Phone, Electrophoresis, 2009, 30(4):579-582.
Martinez, et al., Simple Telemedicine for Developing Regions: Camera Phones and Paper-Based Microfluidic Devices for Real-Time, Off-Site Diagnosis, Anal. Chem., 2008, 80(10):3699-3707.
Mirica, et al., Magnetic Levitation in the Analysis of Foods and Water, Journal of Agricultural and Food Chemistry, 2010, 58:6565-6569.
Mirica, et al., Using Magnetic Levitation for Three Dimensional Self-Assembly, Advanced Materials, 2011, 23:4134-4140.
Moon, et al., Enumeration of CD4+ T-Cells Using a Portable Microchip Count Platform in Tanzanian HIV-Infected Patients, PLoS ONE, 2011, 6(7):e21409, 8 pages.
Park, et al., Advances in Microfluidic PCR for Point-of-Care Infectious Disease Diagnostics, Biotechnol. Adv., 2011, 29(6):830-839.
Preechaburana, et al., Surface Plasmon Resonance Chemical Sensing on Cell Phones, Angewandte Chemie International Edition, 2012, 51(46):11585-11588.
Roy, et al., A Simple and Low-Cost Device Performing Blood Cell Counting Based on Lens-Free Shadow Imaging Technique, Sensors and Actuators B: Chemical, 2014, 201:321-328.
Sanavio, et al., On the Slow Diffusion of Point-of-Care Systems in Therapeutic Drug Monitoring, Frontiers in Bioengineering and Biotechnology, 2015, vol. 3, Article 20, pp. 1-15.
Shafiee, et al., Selective Isolation of Live/Dead Cells Using Contactless Dielectrophoresis (cDEP), Lab on a Chip, 2010, 10:438-445.
Shafiee, et al., Printed Flexible Plastic Microchip for Viral Load Measurement Through Quantitative Detection of Viruses in Plasma and Saliva, Scientific Reports, 2015, 4:9919, 9 pages.
Shen, et al., Point-of-Care Colorimetric Detection with a Smartphone, Lab on a Chip, 2012, 12(21):4240-4243.

(56) References Cited

OTHER PUBLICATIONS

Smith, et al., Cell-Phone-Based Platform for Biomedical Device Development and Education Applications, PLoS ONE, 2011, 6(3):e17150, 11 pages.
Songjaroen, et al., Blood Separation on Microfluidic Paper-Based Analytical Devices, Lab on a Chip, 2012, 12(18):3392-3398.
Tasoglu, et al., Paramagnetic Levitational Assembly of Hydrogels, Advanced Materials, 2013, 25:1137-1143.
Tasoglu, et al., Guided and Magnetic Self-Assembly of Tunable Magnetoceptive Gels, Nature Communications, 2014, 5:4702, 11 pages.
Van Osch, et al., Measuring the Arterial Input Function With Gradient Echo Sequences, Magnetic Resonance in Medicine, 2003, 49:1067-1076.
Vanjari, et al., Validation of a Simple and Cost-Effective Test for Enumeration of CD4 Cells, J Acquir Immune Defic Syndr, 2012, 61(5):e70-e71.
Wang, et al., Integration of Cell Phone Imaging with Microchip ELISA to Detect Ovarian Cancer HE4 Biomarker in Urine at the Point-of-Care, Lab on a Chip, 2011, 11(20):3411-3418.
Wang, et al., Micro-a-fluidics ELISA for Rapid CD4 Cell Count at the Point-of-Care, Scientific Reports, 2014, 4:3796, 9 pages.
Wang, et al., Microchip ELISA Coupled with Cell Phone to Detect Ovarian Cancer HE4 Biomarker in Urine, Methods in Molecular Biology, 2015, 1256:111-121.
Wang, et al., On-Chip Counting the Number and the Percentage of CD4+ T Lymphocytes, Lab on a Chip, 2008, 8:309-315.
Watkins, et al., A Microfabricated Electrical Differential Counter for the Selective Enumeration of CD4+ T Lymphocytes, Lab on a Chip, 2011, 11(8):1437-1447.
Wei, et al., Point-of-Care Platforms for Salivary Diagnostics, The Chinese Journal of Dental Research, 2012, 15(1):7-15.
Whitesides, Cool, or Simple and Cheap? Why Not Both?, Lab on a Chip, 2013, 13:11-13.
Yang, et al., Blood Cell Counting and Classification by Nonflowing Laser Light Scattering Method, Journal of Biomedical Optics, 2004, 9(5):995-1001.
Yetisen, et al., Paper-Based Microfluidic Point-of-Care Diagnostic Devices, Lab on a Chip, 2013, 13:2210-2251.
Ymeti, et al., A Single Platform Image Cytometer for Resource-Poor Settings to Monitor Disease Progression in HIV Infection, Cytometry Part A, 2007, 71A:132-142.
China National Intellectual Property Administration. Notice on the First Office Action for application 201680070911.9, dated Apr. 21, 2020. With translation.
Federal Service for Intellectual Property, Russia. Official Action for application 2018116084, dated May 22, 2020. With translation.
European Patent Office. Office Action for application 16852778.6, dated Dec. 14, 2020. 4 pages.
Japan Patent Office Notification for Reasons for Refusal for application 2018-516775, dated Nov. 10, 2020. With translation. 18 pages.
Kimura, A. "The Progress of Image Analyzers and their Applications to the Particle Shape and Size Distribution Measurement" Aerosol Research. Japanese Association of Aerosol Science and Technology. Sep. 20, 1989, vol. 4 No 3 (1989) p. 192-197. With machine translation.
Knowlton, S., et al. "Smart-phone based magnetic levitation for measuring densities." PLoS One 10.8 (2015):e0134400.
China National Intellectual Property Administration. Notice on the Second Office Action for application 201680070911.9, dated Dec. 28, 2020 With translation.
State of Israel Patent Authority. Office Action for application 258364, dated Dec. 9, 2020. With translation.
Japan Patent Office, Notification of Reasons for Refusal, Application No. 2018-516775, dated Jun. 8, 2021, 14 pages.
State of Israel, Ministry of Justice, The Patent Authority, Notification of Deficiencies in Patent Application No. 258364, Jun. 21, 2021, 8 pages.
Durmus et al., Magnetic Levitation of Single Cells, PNAS, 2015, 112(28):E3661-E3668.
Kose et al., Label-Free Cellular Manipulation and Sorting Via Biocompatible Ferrofluids, PNAS, 2009, 106(51):21478-21483.
Souza et al., Three-Dimensional Tissue Culture Based on Magnetic Cell Levitation, Nature Nanotechnology, 2010, 5(4):291-296.
Intellectual Property of India, Examination Report, Application No. 201837010877, dated Sep. 17, 2021, 7 pages.
Australian Government—IP Australia, Examination Report No. 1, Application No. 2016331215, Nov. 19, 2021, 15 pages.
Huang et al., A Microfluidics Approach for the Isolation of Nucleated Red Blood Cells (NRBCs) from the Peripheral Blood of Pregnant Women, Prenatal Diagnosis, 2008, 28(10):892-899.
Tasoglu et al., Manipulating Biological Agents and Cells in Micro-Scale Volumes for Applications in Medicine, Chemical Society Reviews, 2013, 42(13):5788-5808.
Winkleman et al., Density-Based Diamagnetic Separation: Devices for Detecting Binding Events and for Collecting Unlabeled Diamagnetic Particles in Paramagnetic Solutions, Analytical Chemistry, 2007, 79(17):6542-6550.
Zhu et al., Continuous-Flow Ferrohydrodynamic Sorting of Particles and Cells in Microfluidic Devices, Microfluidics and Nanofluidics, 2012, 13(4):645-654.

\* cited by examiner i-LEV pieces for basic imaging i-LEV pieces for fluorescent imaging i-LEV pieces for fluorescent imaging (advance)

a)

b)

SORTING BIOLOGICAL AND NON-BIOLOGICAL MOIETIES USING MAGNETIC LEVITATION

STATEMENT OF FEDERALLY SPONSORED RESEARCH OR DEVELOPMENT

This invention was made with Government support under contract 1150733 awarded by the National Science Foundation and under contracts CA199075, EB015776 and HG000205 awarded by the National Institutes of Health. The Government has certain rights in the invention.

CROSS-REFERENCE TO RELATED APPLICATIONS

This application represents the U.S. national stage entry of International Application No. PCT/US2016/054987 filed Sep. 30, 2016, which claims the benefit of U.S. Provisional Patent Application Serial No. 62/236,692 entitled "Sorting Biological and Non-Biological Moieties Using Magnetic Levitation" filed Oct. 2, 2015, the contents of which are incorporated by reference herein in its entirety for all purposes.

BACKGROUND

This disclosure relates to systems and methods for levitating populations of moieties, cells, or other such units using one or more magnets in a microfluidic environment. These systems and methods may be used to separate or sort heterogeneous populations of the units from one another, to assembly a multi-unit assembly during the levitating of the units. These systems and methods may also utilize a frame that enables an imaging device, such as a smartphone, to capture the units in real time as they are manipulated in the system.

Magnetic levitation has been traditionally used for analyses of densities and magnetic susceptibilities of individual, macroscopic objects and as a means effective in separating foods, determining the fat content in milk, cheese, and peanut butter, comparing a variety of grains on the basis of their intrinsic densities, guiding self-assembly of objects, and characterizing forensic-related evidence. These earlier magnetic levitation-based experiments were performed using large setups that were not compatible with or geared towards microscopy.

A wide variety of cellular processes, both physiological and pathological, are accompanied by transient or permanent changes in a cell's volumetric mass density or magnetic signature due to formation or quenching of intracellular paramagnetic reactive species, for example reactive oxygen species (ROS) or reactive nitrogen species (RNS). These events include cell-cycle stage, differentiation, cell-death (apoptosis/necrosis), malignancy, disease state, activation, phagocytosis, in vivo and ex vivo cell aging, viral infection, and specific as well as non-specific responses to drugs.

SUMMARY OF THE INVENTION

There is an emerging need for portable, robust, inexpensive and easy-to-use disease diagnosis and prognosis monitoring platforms to share health information at the point-of-living, including clinical and home settings. Herein, a magnetic levitation-based diagnosis system is provided in which different units (for example, white and red blood cells or other moieties) are levitated in a magnetic gradient and separated due to their unique densities in a magnetic gradient. Moreover, an easy-to-use, smartphone incorporated levitation system for corresponding analysis is disclosed. Using the portable imaging magnetic levitation (i-LEV) system, it is shown, for example, that white and red blood cells can be identified and cell numbers can be quantified without using any labels. In addition, cells or other moieties levitated in i-LEV can be distinguished at single unit resolution (for example, single cell), enabling diagnosis and monitoring, as well as clinical and research applications. Among other things, this enables disease diagnosis and monitoring using smartphones at various settings including home-settings and clinical settings.

There are many potential applications of such disclosed systems. Systems such as these may also be used, for example, as a microfluidic platform for label-free, high throughput isolation of circulating tumor cells (CTCs) from whole blood. The platform employs the principle of magnetic levitation to separate cells based on their density profiles while they flow in a microchannel. Cancer cells that typically have lower intrinsic densities than blood cells may be levitated at a higher level within the microchannel, in which three different paramagnetic fluids flow top-on-bottom (top and middle flows: carrier buffer, bottom flow: sample blood containing cancer cells). Those levitated cancer cells may then be extracted from the sample blood flow, and are collected within a carrier buffer fluid flowing on the top. Accordingly, the platform enables, for example, the high throughput isolation of rare CTCs from cancer patient's blood, which facilitates clinical studies for CTC-derived biomarkers and molecular targets.

Accordingly, the disclosed system can be highly applicable for use in the separation of plasma from whole blood and also for the isolation of CTC from whole blood as a few examples.

Still yet, the separation and sorting provided by the system has various other applications. For example, it invokes methods for multi-cellular assembly based on magnetic signatures, as enabling technology for three-dimensional cell culture. It further may be used for the magnetic levitation of cells as a potential ground-based simulation of microgravity. Still further, these tools may be used in method for sorting, recovery and characterization based on magnetic/density properties and imaging/molecular profiling.

According to one aspect of the present invention, a magnetic levitation-based diagnosis system is provided. The magnetic levitation-based diagnosis system includes a levitation device for separating a heterogeneous population of moieties in which variances in the moieties are based on differences in one or more of magnetic susceptibility and intrinsic density. The device includes at least one magnet producing a magnetic field in which the magnetic field is sized to interact with a microcapillary or microfluidic channel for reception of a sample containing the heterogeneous population of moieties. The microcapillary or microfluidic channel is defined by a plurality of layers having portions of the microcapillary or microfluidic channel formed therein with at least one of the plurality of layers providing an inlet channel into the microcapillary or microfluidic channel and at least two of the plurality of layers providing separate outlets from the microcapillary or microfluidic channel.

In some forms, the plurality of layers may include at least two layers in which each of layers includes a respective inlet and a respective outlet formed therein.

In some forms, each of the respective layers may be formed from a laser-machined material.

In some forms, a thin film may be disposed between at least two of the plurality of layers to establish a top and bottom outlet.

According to another aspect of the present invention, this system may be employed in a method of sorting. The method includes flowing a sample including the heterogeneous population of moieties and a paramagnetic medium into the inlet(s) and the microcapillary or microfluidic channel. A magnetic field is applied to the sample including the heterogeneous population of moieties to separate the heterogeneous population based on a difference in at least one of magnetic susceptibility and intrinsic density between individual members of the heterogeneous population of moieties and the paramagnetic medium. Thereafter, a first portion of the sample is flowed out of a top outlet and a second portion of the sample is flowed out of a bottom outlet, thereby separating a first group of the heterogeneous population of moieties from a second group of the heterogeneous population of moieties.

In some forms of this method, the plurality of layers may include at least three layers including a top, middle and bottom layer in which each of the three layers include a respective inlet and a respective outlet formed therein. It is contemplated that, in this form, the step of flowing the sample into the inlet(s) and the microcapillary or microfluidic channel may include introducing the sample including the heterogeneous population of moieties and a paramagnetic medium into the bottom inlet and the paramagnetic medium into the top and middle inlets. It is contemplated that as many layer, inlets, and/or outlets as is desired may be added to the system; while the form above identifies three or more layers, three layers is only one example number of layers that may be provide and likewise there may be more or less than three outlets.

In some forms, the sample may be a blood sample mixed with a paramagnetic medium. The blood sample may include circulating tumor cells (CTCs) or circulating tumor clusters/emboli (CTM) and the CTCs or CTM may be separated and flowed into the top channel after exposure to the magnetic field in the microcapillary or microfluidic channel.

In some forms, the method may further include the step of stabilizating of separated population of moieties with the assistance of at least one of temperature and cross-linking.

According to another aspect of the present invention, a method of sorting using a system including a device for separating a population of biological or non-biological moieties is provided in which the device includes at least one magnet producing a magnetic field that is sized to interact with a microcapillary or microfluidic channel for the reception of a sample containing the population of moieties. In this method, a sample including the population of moieties and a paramagnetic medium flows from an inlet into the microcapillary or microfluidic channel towards an outlet. While the sample is in the microcapillary or microfluidic channel, a magnetic field is applied using the magnet(s) to the sample. The application of the magnetic field blocks at least some, but not all, of members of the population of moieties from flowing towards the outlet, thereby separating the population of moieties.

In some forms of this method, the blocking of at least some, but not all, of members of the population of moieties may occur at a magnetic edge of the magnetic field due to high magnetic induction.

In some forms, the population of moieties may include a blood sample in which the blood cells are blocked from moving past the magnetic field produced by the magnet(s), but plasma is able to flow past the magnetic field produced by the magnet(s) through the microcapillary or microfluidic channel to the outlet.

In some forms, the method may further include the step of stabilizing of separated population of moieties with the assistance of at least one of temperature and cross-linking.

According to still another aspect of the present invention, a method is provided of assembling a multi-moiety assembly based on magnetic signatures using a magnetic levitation-based diagnosis system including a levitation device including at least one magnet producing a magnetic field in which the magnet(s) is/are proximate a microcapillary or microfluidic channel for reception of a sample containing a population of moieties. A sample including the population of moieties and a paramagnetic medium is introduced into the microcapillary or microfluidic channel. While the sample is in the microcapillary or microfluidic channel, a magnetic field is applied using the magnet(s) to the sample, such that the application of the magnetic field levitates at least a portion of the population of moieties to place the population of moieties in a spatial relationship to one another in which the population of moieties aggregate to form the multi-moiety assembly.

In some forms of this method, the aggregation of the population of moieties to form the multi-moiety assembly may occur spontaneously over a duration of time while the population of moieties substantially remain in the spatial relationship established by the levitation induced by the magnetic field.

In some forms, the magnetic field may be generated by permanent magnets. In other forms, the magnetic field may be generated by coils induced by electrical current. Still other forms of magnetic field generation may also be used.

The moieties may be a number of different types of units or materials. In some forms of the method, the moieties may be cells. In other forms of the method, the moieties may be polymeric.

In some forms of the method, the aggregation of the population of moieties to form the multi-moiety assembly may occurs and may result in stabilization with the assistance of at least one of temperature and cross-linking.

According to still yet another aspect of the present invention, a magnetic levitation-based diagnosis system is provided for use with an imaging device. The system includes a levitation device for separating a heterogeneous population of cells in which the variances in the cells are based on differences in magnetic susceptibility. The device includes at least one magnet producing a magnetic field in which the magnet(s) is/are proximate a microcapillary or microfluidic channel for reception of a sample containing a heterogeneous population of cells. The system further includes a light source, a lens (in some forms of the system, although the lens may be omitted), and a frame. The frame supports the levitation device, the light source, and, if present as part of the system, the lens. This frame is further configured to support an imaging device. The frame supports the light source in a position to transmit light through the levitation device and, if present, the lens to the imaging device for real-time observation of at least a portion of heterogeneous population of cells.

In some forms, the imaging device may be one of a smartphone, a CMOS camera, and a CCD camera. The data collected by the imaging device may be transmitted over Bluetooth or wifi or phone networks, particularly when the site of operation is the a remote point of care.

In some forms, the system may further include a neutral density filter supported by the frame in which the neutral density filter is positioned between the light source and the levitation device.

In some forms, the system may further include the imaging device supported by the frame in which the imaging device includes a camera. In this form, the frame may receive the imaging device in a position such that the camera is positioned to receive an image transmitted through the lens. The imaging device may be configured to observe the separation of a heterogeneous population of cells in real-time.

In some forms, the frame may have a compacted position to reduce the size of the frame for portability and an expanded position in which the frame is expanded. When the frame is in the expanded position, the frame may be configured to receive the imaging device in recesses on a top surface thereof.

When the imaging device is received in the frame, the camera of the imaging device may face the lens and a display of the imaging device may remain viewable for observation of the sample containing the heterogeneous population of cells.

According to still yet another aspect of the present invention, a method is provided for observing a heterogeneous population of cells in a magnetic levitation-based system. The sample of the population of cells is received or placed in a microcapillary or microfluidic channel of a levitation device. An imaging device is placed in a frame. The population of cells is separated in the levitation device. While separating the population of cells in the levitation device, the imaging device is used to collect images of the separation of the population of cells.

In some forms of this method, the collection of images of the separation of the population of cells may occur in real-time.

In some forms of this method, the sample may be blood. In other forms of this method, the sample may be a bodily fluid including saliva, urine, plasma, serum, and stool; swabs including skin, anal, nasal and vaginal swabs or environmental swabs from a door handle; and proximal fluids including tears, lavash fluid from lungs, interstitial tissue fluids from a breast. Of course, it will be appreciated that this sample list is exemplary and not limiting.

In some forms, the method may further include the step of counting and/or quantifying at least some of the population of cells from the collected images of the population of cells.

According to yet another aspect of the invention, a magnetic levitation-based system includes a levitation device for separating a heterogeneous population of moieties wherein variances in the moieties are based on differences in magnetic susceptibility and/or intrinsic density. The device including at least one magnet producing a magnetic field in which the magnetic field is sized to interact with a microcapillary or microfluidic channel for reception of a sample containing the heterogeneous population of moieties. The system further includes at least one needle at the inlet and/or outlet of the microcapillary or microfluidic channel for introducing or withdrawing fluid from the microcapillary or microfluidic channel at a respective pre-defined position over the height and/or width of the microcapillary or microfluidic channel.

In some forms, there may be a plurality of needles one or both of the inlet or the outlet and each of the plurality of needles may be in fluid communication with the microcapillary or microfluidic channel at a different spatial position.

In some forms, to promote sorting, the first injection needle at the inlet may be at a different height than a second suction needle at the outlet. As previously discussed, there may be magnetic separation of the moieties in the samples therebetween.

According to another aspect, a method of evaluating a quality of individual embryos and oocytes for use in reproductive medicine is disclosed. The method includes placing a sample including one or more embryos or oocytes in a microcapillary or microfluidic channel of a levitation device and levitating the sample including embryos or oocytes in the levitation device. The quality of the embryos or oocytes is graded on one or more of the density and levitation profile.

In some forms, the method may further include the step of selecting one or more of the embryos or oocytes based on the grading of the quality of the embryos or oocytes on one or more of the density and levitation profile and employing the one or more embryos or oocytes that are selected in an in vitro fertilization procedure.

According to another aspect, a method for levitating a plurality of moieties encapsulated in droplets in a magnetic levitation system is disclosed. The method includes the steps of encapsulating the plurality of moieties in a plurality of droplets and suspending the plurality of droplets in a sample, placing the sample containing the plurality of droplets in a microcapillary or microfluidic channel of the magnetic levitation system, and levitating the plurality of droplets in the magnetic levitation system.

In some forms of this method, the sample may further includes a plurality of droplets not encapsulating any of the plurality of moieties.

These and still other advantages of the invention will be apparent from the detailed description and drawings. What follows is merely a description of a preferred embodiment of the present invention. To assess the full scope of the invention, the claims should be looked to as the preferred embodiment is not intended to be the only embodiment within the scope of the claims.

BRIEF DESCRIPTION OF THE DRAWINGS

FIG. 1A illustrates the arrangement of magnets, capillary channels and mirrors found in the levitation device. FIG. 1B illustrates (I) A small volume (30 µL) of a blood sample being loaded or collected into the microcapillary from a patient, (II) the blood sample loaded to the microcapillary channel using capillary forces, (III) the sealing of the microcapillary channel with Critoseal™, and (IV) the capillary channel being introduced between two permanent neodymium magnets whose same poles are facing each other. FIG. 1C illustrates the i-LEV set-up including a smartphone, lens, levitation device, light source, and filters supported by a surrounding frame.

FIG. 2A shows WBC and RBC separation image taken by i-LEV. FIG. 2B shows RBC and WBCs levitated at different heights are imaged by conventional microscopy using bright field. FIG. 2C shows fluorescent images of CD45-labeled WBC. FIG. 2D shows the overlap of the bright field and CD45 images to confirm the separation of WBC and RBC. FIG. 2E shows live-dead assay imaging of RBCs and WBCs by i-LEV in which live RBCs levitate while dead WBCs aggregate at bottom of the capillaries. FIG. 2F shows bright field, FIG. 2G shows DAPI-labeled, and FIG. 2H show overlapped images of WBC using fluorescence microscopy.

FIG. 3A includes images of RBC band width at different time points showing changes in width of the levitated cell bands over time. FIG. 3B plots the width of the RBC at two different concentrations (90 and 450 million cells/mL) being analyzed by i-LEV over 30 min. FIG. 3C includes images of levitated red blood cells at different RBC concentrations varying from 250 million cells/mL to 0.8 million cells/mL and FIG. 3D plots the width of the blood band for each of these RBC concentrations with the graph being linear within a cell concentration range between 50 and 250 million cells/mL. FIG. 3E includes images of levitated WBC at different concentrations and FIG. 3F plots the width of the blood band is against the WBC concentration.

FIG. 4A is an image of RBC at a concentration of 100,000 cells/mL and FIG. 4B illustrates the detection of single blood cells using image algorithms. FIG. 4C illustrates density measurement of polyethylene beads in the magnetic levitation platform in which beads between 10-100 μm in diameter with different densities (1.025 g mL$^{-1}$, 1.031 g mL$^{-1}$, 1.044 g mL$^{-1}$, and 1.064 g mL$^{-1}$) are shown to have distinct levitation heights in 30 mM Gd$^+$. FIG. 4D illustrates beads with 1.064 g mL$^{-1}$ density have different levitation heights at different Gd$^+$ concentrations (10 mM, 30 mM, 60 mM). FIG. 4E shows a linear fitting curve that provides a standard function to measure densities of particles.

FIGS. 5A-5C are fluorescence microscopy images of WBC and RBC separation in different Gd+ concentrations (30, 60 and 90 mM), while FIGS. 5D-5F are the same process imaged using the i-LEV system. Both imaging platforms show that rising Gd$^+$ concentrations increase levitation height, whereas separation resolution decreases.

FIG. 7A shows that the levitation of red blood cells over time that 75 mg/mL of chloroquine was spiked into. FIG. 7B shows the levitation heights and image analysis of chloroquine concentrations of 1.25, 2.5, 5 ad 7.5 mg/mL. FIG. 7C is a zoomed in graph of FIG. 7B showing a more detailed graph to show effects of each concentration. FIG. 7D are the actual images of analyzed to generate the data sets in FIGS. 7B and 7C in which density beads were added each time for calibration experiments.

DETAILED DESCRIPTION OF THE INVENTION

Figure 1:
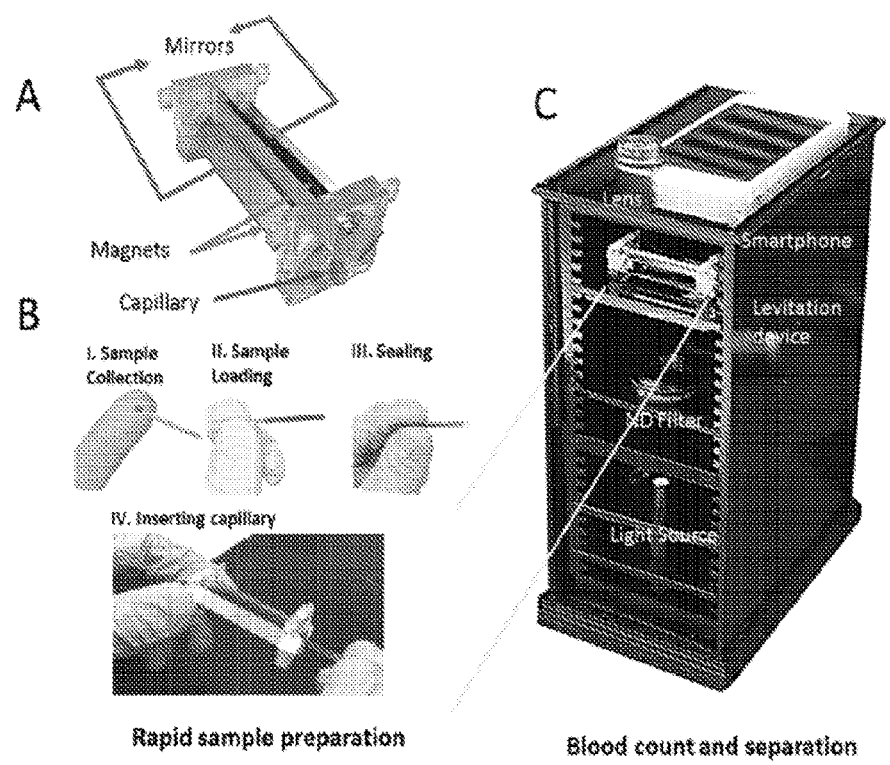
FIG. 1 illustrates the i-LEV platform for cell quantification and rapid sample preparation.

Below various exemplary structures are provided for the separation and sorting of biological and non-biological moieties, such as for example, cells. In each of the subsections below various aspects are described including the construction of an "i-LEV" device, which is a portable levitation system which may incorporate an imagining device (such as a smartphone) to provide point of care (POC) imaging and analysis of a sample containing a population of moieties. Subsequent description of moiety sorting and blocking techniques are then further described. Finally, the use of such levitation systems in the construction of 3-D self-assembled systems are described.

The following are provided by way of example only and to describe the concepts or provide proof-of-concept through experimental data. One having ordinary skill in the art will appreciate that these examples are not limiting, but only help to illustrate some of the applications and structures falling within the scope of the claims.

Integrating Cell Phone Imaging with Magnetic Levitation (i-LEV)

A magnetic levitation-based diagnosis system is disclosed herein that provides building blocks that can be assembled easily at any location to provide a portable set-up for imaging and analyzing blood or other types of samples.

This is a portable, robust, inexpensive and easy-to-use disease diagnosis and prognosis monitoring platforms to share health information at the point-of-living, including clinical and home settings. Recent advances in digital health technologies have improved early diagnosis, drug treatment, and personalized medicine. Smartphones with high-resolution cameras and high data processing power enable intriguing biomedical applications when integrated with diagnostic devices. Further, these devices have immense potential to contribute to public health in resource-limited settings where there is a particular need for portable, rapid, label-free, easy to use and affordable biomedical devices to diagnose and continuously monitor patients for precision medicine, especially those suffering from rare diseases, such as sickle cell anemia, thalassemia and chronic fatigue syndrome.

Here, a magnetic levitation-based diagnosis system is presented in which different cell types (for example, white and red blood cells) or moiety types are levitated in a magnetic gradient and separated due to their unique densities. Moreover, an easy-to-use, smartphone incorporated levitation system is introduced for cell and moiety analysis. Using this portable imaging magnetic levitation system (an example of which, the i-LEV, being referred to herein by name), it is shown that white and red blood cells can be identified and cell numbers can be quantified without using any labels. In addition, cells levitated in i-LEV can be distinguished at single cell resolution, potentially enabling diagnosis and monitoring, as well as clinical and research applications.

With the i-LEV, a finger prick blood sample can be collected and the blood levitated in a capillary of the system. Thereafter, a smartphone received in the system can take images to analyze the blood. The set-up includes several components to accommodate different applications.

Rapid diagnostic tools are used in multiple fields, including clinical and veterinary medicine, as well as food safety. Point-of-care (POC) devices enable inexpensive, rapid, portable, label-free, accessible and easy-to-use diagnostic solutions. Moreover, POC devices can be applied to monitor compliance and disease progression. However, most systems require extensive sample preparation and labeling steps, which limit their usage. Precision medicine tailors treatments to a patient's profile based on their genetic data. Cellular and molecular analyses are increasingly being performed by research institutions and drug companies to achieve more efficient drug development and improved early diagnoses. In this respect, smartphones with high-resolution cameras, fast computing power, graphics processors, data storage and connectivity capacities are used for various healthcare platforms, including telemedicine and POC diagnostics.

As one example, the red blood cell (RBC) and white blood cell (WBC) count is a diagnostic parameter assessed in pathology laboratories. Currently, hemocytometry, coulter counting or flow-cytometry are the most widely used methods to count and classify blood cells. In Table 1, the i-LEV device are compared to these established methods.

TABLE 1

| PARAMETERS | Hemocytometer[37] | Flow Cytometer (FACS)[27, 37] | Coulter Counter[38] | Miniature Microfluidic Device[39-41] | i-LEV |
|---|---|---|---|---|---|
| Functionality | Hemocytometers are cell-counting devices consisting of a microfluidic channel with 100 μm depth. Images are taken with a conventional microscope. | Flow cytometers are used for cell counting as well as cell sorting. Cells are suspended as they flow in a stream through a laser beam. | A Coulter Counter is designed for cell counting as the cells are suspended in electrolytes. | Several of these devices are used for blood counting and separation in microfluidic systems, including electro-osmotic flow, bifurcation, geometric obstructions, acoustic standing wave forces, porous filters, membrane filtration and cross-flow filtration. | I-LEV is used to asses blood counts. The width of the blood band across a capillary is measured to quantify the blood concentration. |
| Assay time | >20 min | >1 hr | >1 hr | >2 hr | 15 min stabilization time and less than 30 sec of analysis time |
| Labeling | Not required | Required | Not Required | Required | Not required |
| Cost | $10 | Requires LASER and detection system >$10,000 | >$5,000 | >$2,000 | $1 for chambers |
| Complexity | Since cell counting is performed manually, It is time consuming. It is not as sensitive due to sampling errors. | It requires high volume of blood. Reagents for pretreatment are expensive. Training required for laboratory technicians | Requires extensive design and circuit building. It must be calibrated regularly. | Miniature microfluidic devices require an independent liquid flow source such as a peristaltic pump or a syringe pump, and cannot easily be produced in a portable platform. | i-LEV consists of a magnetic evitation device and a smartphone. It requires a finger-prick volume of blood. |
| Accessibility | Deliverable and it can be used in centralized lab settings | Performed at established centers, hospitals and clinics. | Generally performed at established hospitals and clinics | Deliverable and it can be used without requiring centralized hospitals or clinics | I-LEV can provide simple blood counting tests accessible to the general public in multiple settings, including home and clinical settings. |

Coulter and flowcytometry are complex and expensive, whereas hemocytometry is inexpensive but labor intensive, time-consuming and not practical for POC testing. Recently developed methods have advanced the field by applying sensitive and robust technologies. However, an inexpensive and accurate blood count analyzer is still missing for POC treatment.

In recent years, magnetic levitation principles have been used to monitor and biologically characterize cells and cellular events. Earlier studies have shown that different cell types with various sizes ranging down to the sub-micron level can be aligned at unique heights using levitation platforms. Here, a smartphone-based magnetic levitation system is disclosed that, for example, identifies and quantifies blood cells without using labels. The system assesses RBC and WBC counts in whole blood samples by analyzing the width of the blood band in a high magnetic field. Previously, the separation of blood cells without labeling has posed a significant challenge in clinical diagnostics. Using the disclosed system, RBC and WBC can be separated due to their unique density signatures. The i-LEV device is an easy-to-use and easy-to-access POC solution for blood cell counting that could be used to monitor disease progression and drug effectiveness in the home-setting.

Example I: i-LEV Construction and Design

Figure 11:
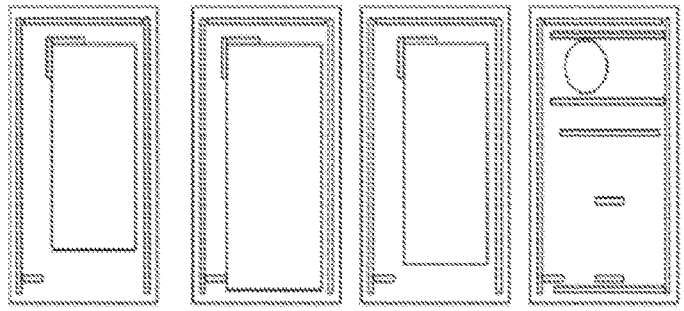
FIG. 11 illustrates an i-LEV frame component design for three different applications and three different phones. The bottom three rows are for different heights of i-LEV for different applications (i.e., basic imaging v. fluorescent imaging v. advanced fluorescent imaging). The top row illustrates the adapter piece for three different smartphones and bases.
Figure 11:
Figure 11:
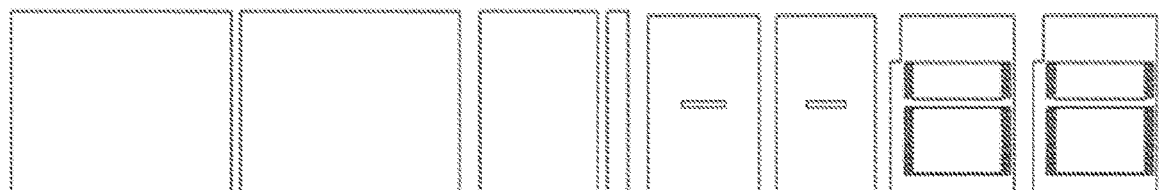
Figure 11:
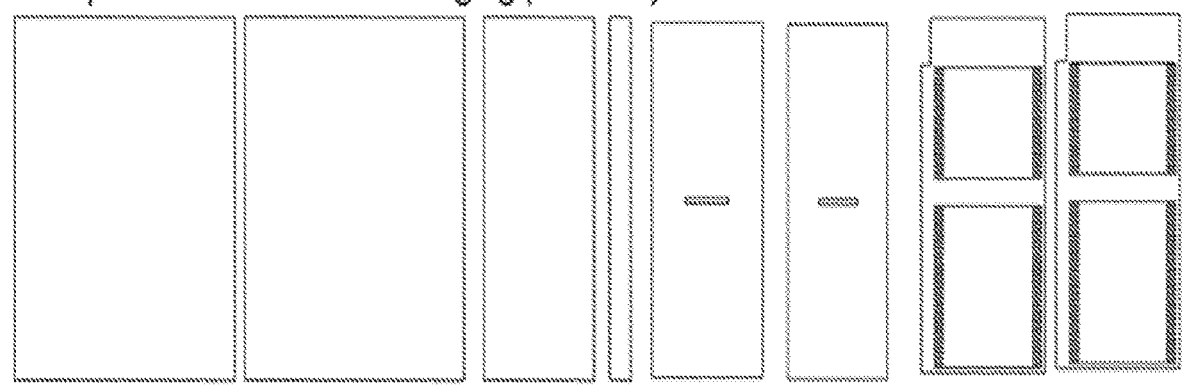

The experimental setup of the magnetic levitation-based diagnosis system is as follows to build and use one form of the i-LEV system as illustrated in FIG. 1C. 3 mm-thick poly-methyl methacrylate (PMMA) pieces cut with a laser cutter (VLS 2.30 Versa Laser) were used to assemble the i-LEV system with dimensions of 160, 100, 205 mm, as shown in FIG. 1C. Threads with 3 mm steps were designed to accommodate insertion parts for different applications. The top layer of the i-LEV system has several different versions that are compatible with different brands of smartphones, as can be seen in the top row of FIG. 11. The height of the set-up can be halved for simple experiments which do not require extensive optical systems and light sources. The full-size i-LEV system can accommodate fluorescent imaging hardware by inserting broadband LEDs, as well as excitation and emission filters. Micro capillary channel (1 mm×1 mm cross-section, 50 mm length and 0.2 mm wall thickness), N52 grade neodymium magnets (NdFeB) (50 mm length, 2 mm width and 5 mm height), and side mirrors are used to build the magnetic levitation device as illustrated in FIG. 1B.

As best seen in FIG. 1C, the levitation device is placed 3 cm below the smartphone that can contain a lens adapter. Phones with auto-focus features can adjust the focal plane without having to move the sample up and down. Before each separate measurement, a micro capillary channel is placed between the magnets after the plasma has been treated for 3 min at 100 W, 0.5 Torr. Two mirrors were placed at 45° to pass the light through the levitation channel, as the magnets block the direct incoming light. The channel illumination is aligned with the smartphone camera.

Figure 3:
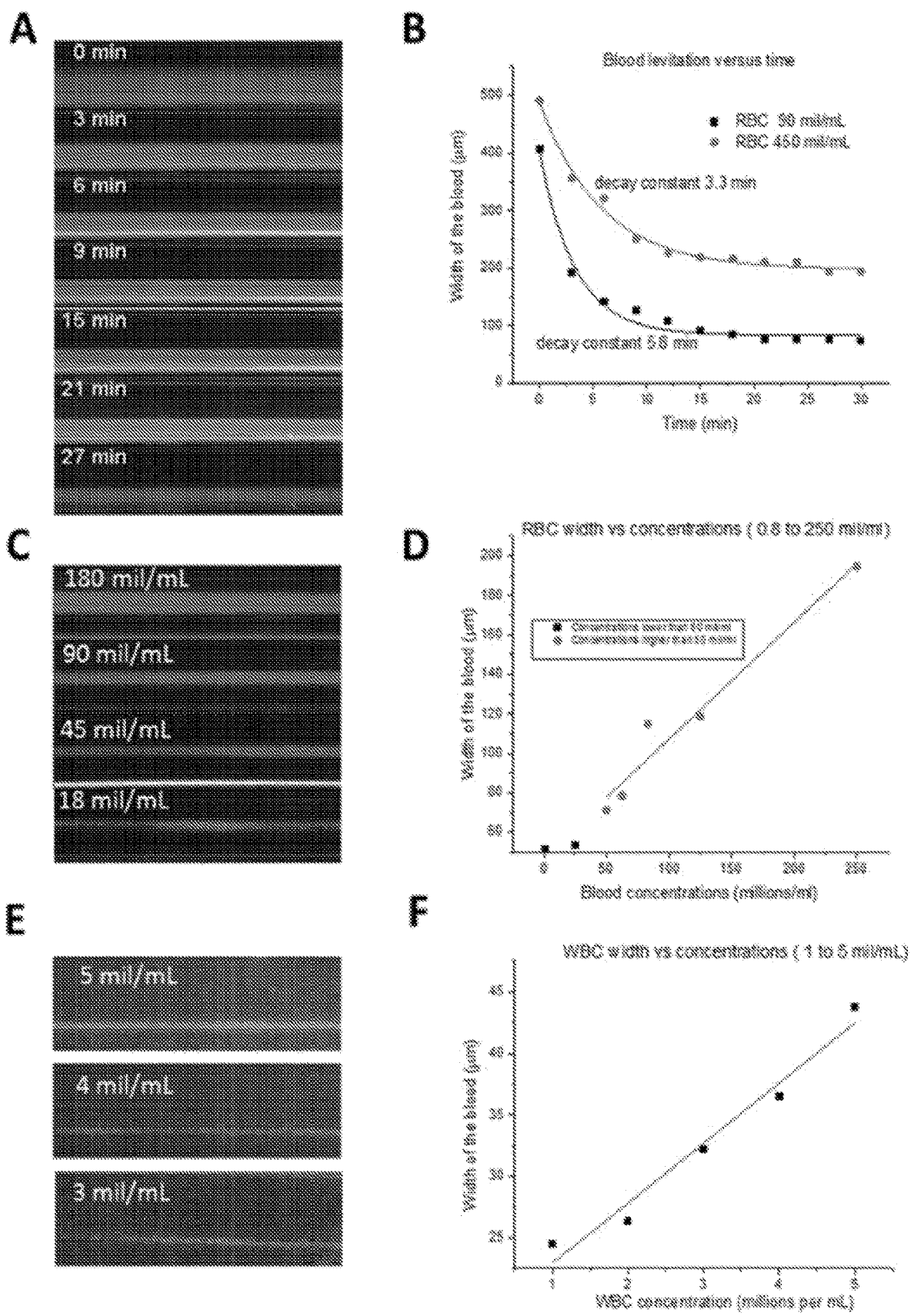
FIG. 3 shows the width of the red and white blood cells at different dilutions and time points.

Sample Measurements were taken. RBC, WBC and polyethylene beads were spiked in PBS containing different concentration of paramagnetic medium (30 mM, 60 mM and 90 mM Gd+). 30 µL of sample were pipetted into the micro capillaries and the channel was sealed with Critoseal™. The samples were levitated for 30 min until they reached their equilibrium height within the system. Calibration measurements were performed to quantify stabilization time as shown in FIGS. 3A and 3B. The width and height of the cells and beads were imaged and analyzed using imageJ.

The levitation of red blood cells (RBC) was as follows. Blood samples from healthy donors were received from Stanford University Blood Center. Whole blood was diluted at varying ratios in PBS containing 30 mM Gd+. Concentrations were described in the results. Concentrations of 450 and 90 million cells/mL of blood were used to measure blood stabilization time. Varying concentrations of blood, ranging from 250 to 0.8 million cells/mL were used to correlate the width of the blood band and cell concentrations.

The levitation of white blood cells (WBC) was as follows. Whole blood was mixed with RBC lysis buffer at a 1:10 ratio. RBC were lysed after 5 min of incubation and the blood samples were suspended at 1,500 rpm for 3 min. The resulting WBC pellet was re-suspended in PBS. Incremental concentrations between 1 and 5 million WBC/mL were used to correlate the width of the WBC levitation band with the cell concentrations.

Experiments were performed with live white blood cells. WBC were labeled with anti-CD45 antibody conjugated FITC (1:20 BD Pharmingen) for 30 min. WBC were then washed twice with PBS and re-suspended in PBS. At the end of this process, live WBC and 1×RBC were suspended (50:50) in PBS with 30 mM Gd+ at 1,500 rpm for 3 min. Cells were levitated for 30 min and imaged.

Experiments were performed with dead white blood cells. After RBC lysis, WBC were frozen overnight at −80° C. in PBS without a cryoprotective agent in order to kill WBC. After overnight incubation, dead WBC cells were stained with 4′,6-Diamidino-2-phenylindole dihydrochloride (DAPI) (1:1,000 Invitrogen) for 15 min at room temperature. After staining, dead WBC were washed twice with PBS and re-suspended in PBS. Finally dead WBC and 1.000× RBC were mixed and suspended (50:50) in PBS with 30 mM Gd+ at 1,500 rpm for 3 min. Cells were levitated for 30 min and imaged.

Image analysis was performed. Step-by-step image analysis of RBW was performed using ImageJ. Briefly, the image taken by the smartphone was uploaded to ImageJ. Then, the levitated blood band was cropped and the background was subtracted. The image was converted to 16-bit and the threshold was adjusted to "Default-BW" settings. Area, center of mass, and bounding rectangle were measured. Dividing the measured area by the bounding rectangle provided the average height of the blood band. Each step of image analysis is explained in more detail in the Supplementary Information.

The portable, magnetic levitation-based imaging platform shown in FIG. 1 has several components including: i. a front panel with several threads to mount components of the system; ii. a lens, which is placed right behind the smartphone to focus the images on the camera; iii. a levitation device with capillaries that is placed directly below the lens to image the band width of levitated blood cells; and iv. additional components such as simple LED light sources and ND filters to improve the images. The front panel has a slide-in door to block external light. The set-up was designed using poly-methyl methacrylate (PMMA) building blocks prepared with a laser cutter. The levitation device is made of magnets, mirrors, and channel. Two permanent magnets (50 mm length, 2 mm width and 5 mm height) are set up in such an orientation that the same poles face each other. A capillary channel (50 mm length, 1 mm×1 mm cross-section, 0.2 mm wall thickness) can be inserted between the magnets. Side mirrors are used to illuminate and observe the levitation channel. Samples spiked into a paramagnetic medium (in this instance, Gadavist) are levitated inside the medium at a position where the buoyancy force and the magnetic force are equal. The levitation height of the sample is calculated based on Equation 1.

$$\frac{\Delta \chi}{\mu_0} B \cdot \nabla B - \Delta \rho g = 0 \quad \text{(Eq. 1)}$$

Figure 2:
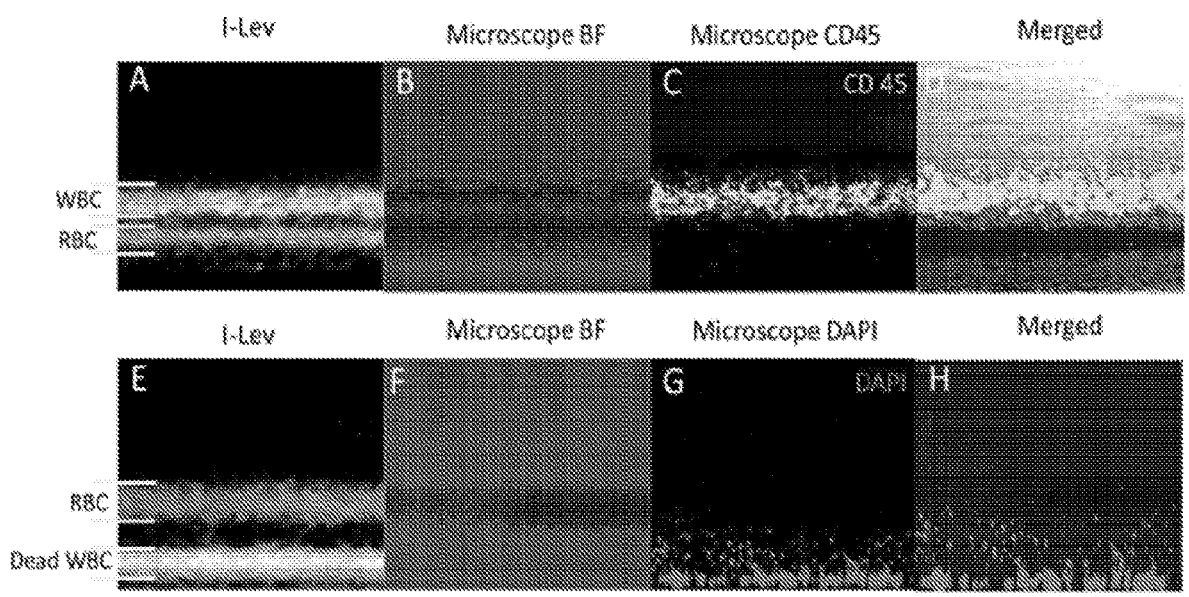
FIG. 2 illustrates the separation of red and white blood cells within the i-LEV platform.

The first part of the equation represents the magnetic force applied to a particle, while the second part represents the buoyancy force. The magnetic induction, gravitational acceleration, difference between volumetric densities of cells and medium, and permeability of the free space are represented by $B$, $g$, $\rho$, and $\mu_o$, respectively. Samples are levitated at unique heights mainly based on their density, independent of their mass and volume. To demonstrate the i-LEV system's potential to separate different sample species, RBC and WBC were mixed at equal concentrations of 5 million cells/mL and separated according to their different levitation characteristics as illustrated in FIG. 2A. The same samples were also imaged using regular microscopy to confirm the types of cells that levitated different heights as illustrated in FIGS. 2B-2D. Overlapped images of WBC labeled with CD45 and the bright field image of the mixed RBC and WBC sample clearly validated the i-LEV results as illustrated in FIGS. 2A-2D. Additionally, live-dead assays were performed with WBC and RBC. First, WBC were stained and frozen overnight. These dead cells were then spiked into RBC samples at equal concentrations. The i-LEV system shows only RBC levitated at the middle of the channel, whereas dead WBC aggregated at the base as illustrated in FIG. 2E. To validate the results, the dead WBC was stained with DAPI and visualized them by fluorescence microscopy. The overlapped bright field image of WBC seen in FIG. 2F and DAPI-stained WBC seen in FIG. 2G confirmed the dead-live assay results as illustrated in FIGS. 2F-2H.

Figure 5:
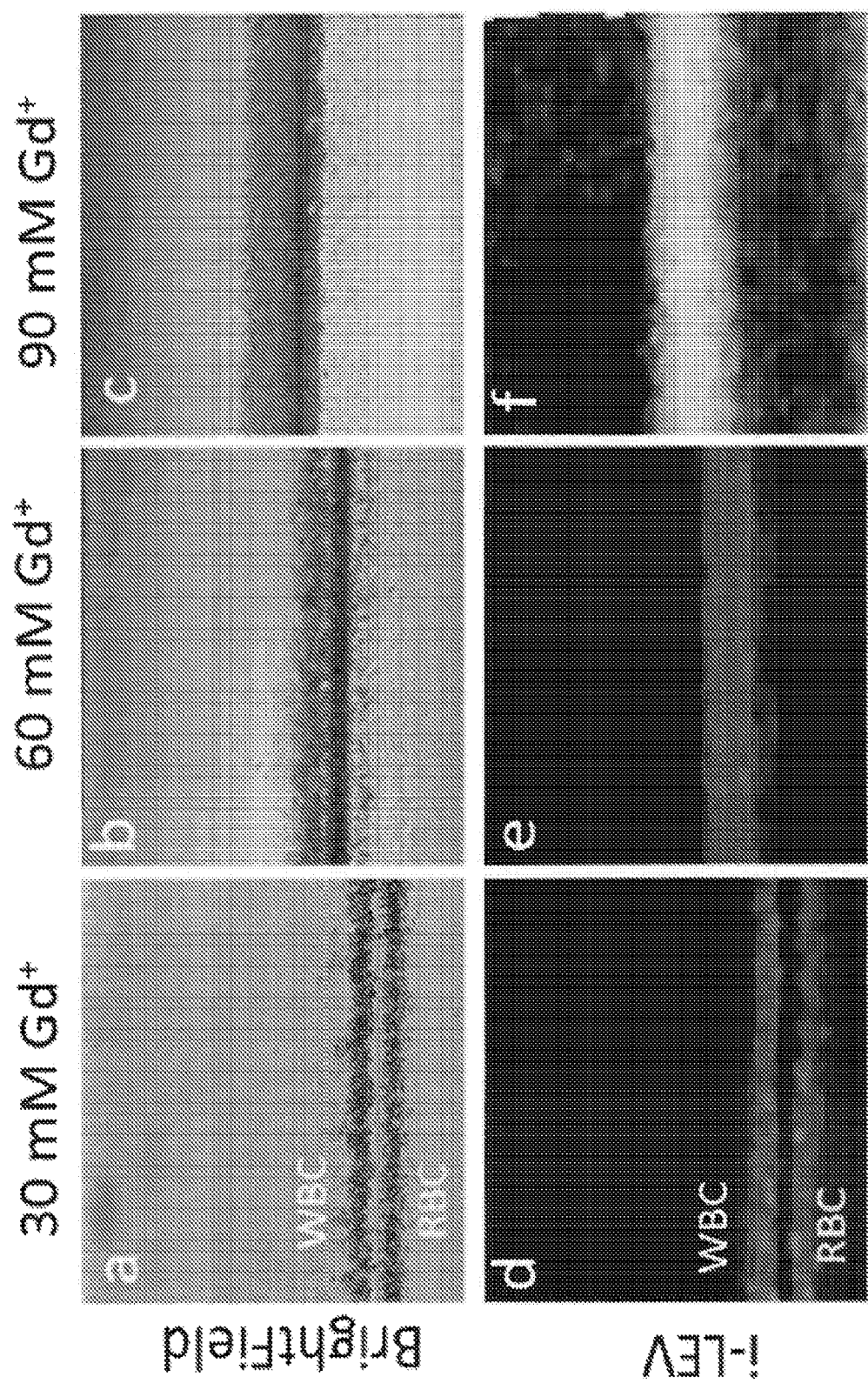
FIG. 5 illustrates RBC and WBC separation at different Gd$^+$ concentrations.

Next, a RBC and WBC mixture was levitated and separated using two other Gadolinium (Gd+) concentrations to identify the optimal Gd+ concentration for cell separation experiments as illustrated in FIG. 5. As the Gd+ concentration was increased (for example, from 60 and 90 mM) the levitation height rose and it became harder to distinguish the bands from one another. The results indicate that the ideal Gd+ concentration in this example experiment is around 30 mM, as this concentration allows optimal levitation while keeping the cells at an adequate distance from the capillary walls. In this condition, the resulting bands are easy to distinguish.

i-LEV was then used to quantify RBC spiked in phosphate buffered saline (PBS). To evaluate equilibration time, calibration measurements were first performed at different time points. The whole blood samples spiked in PBS at a final concentration of 450 million cells/mL were levitated for 30 min. Samples were imaged every 3 min during levitation, demonstrating that cells were equilibrated at their unique levitation heights after approximately 15 min as depicted in FIG. 3A. Experiments with 90 million cells/mL blood were performed to test the stabilization time at different concentrations. The exponential time constants for the stabilization curves were 5.8 min for 450 million cells/mL and 3.3 min for 90 million cells/mL. As further shown in FIG. 3B, the blood cell concentration versus time curves show that the equilibration time for the curves was again 15 min. Higher concentrations of blood cells took longer to equilibrate. Further validation experiments were performed to assess the changes in blood bandwidth at different concentrations. RBC were imaged with the i-LEV system at concentrations of 250, 125, 63, 50, 25 and 0.8 million cells/mL. Each sample was quantified using a hemocytometer to confirm the calculated blood counts. To assess the cell concentrations, the width of the levitated blood band across the channel was measured by dividing the total area of the blood by width of the illuminated region. At higher concentrations (between 50 to 250 million cells/mL), the blood width versus concentrations curves were linear with a slope of 0.6 micrometers per million cells/mL. However, as the cell concentration decreased (for example, from 0.8 to 25 million cells/mL) the curves lost their linearity as can be seen in FIG. 3D. For blood cell concentrations above 50 million cells/mL, it was observed that the width of the blood band during levitation was correlated with the cell concentration. WBC were also imaged at varying concentrations ranging from 1 to 5 million cells/mL and plotted the concentration against the width of the blood band as illustrated in FIGS. 3E-3F. WBC concentrations also correlated with the width of the blood band in a linear manner.

Figure 4:
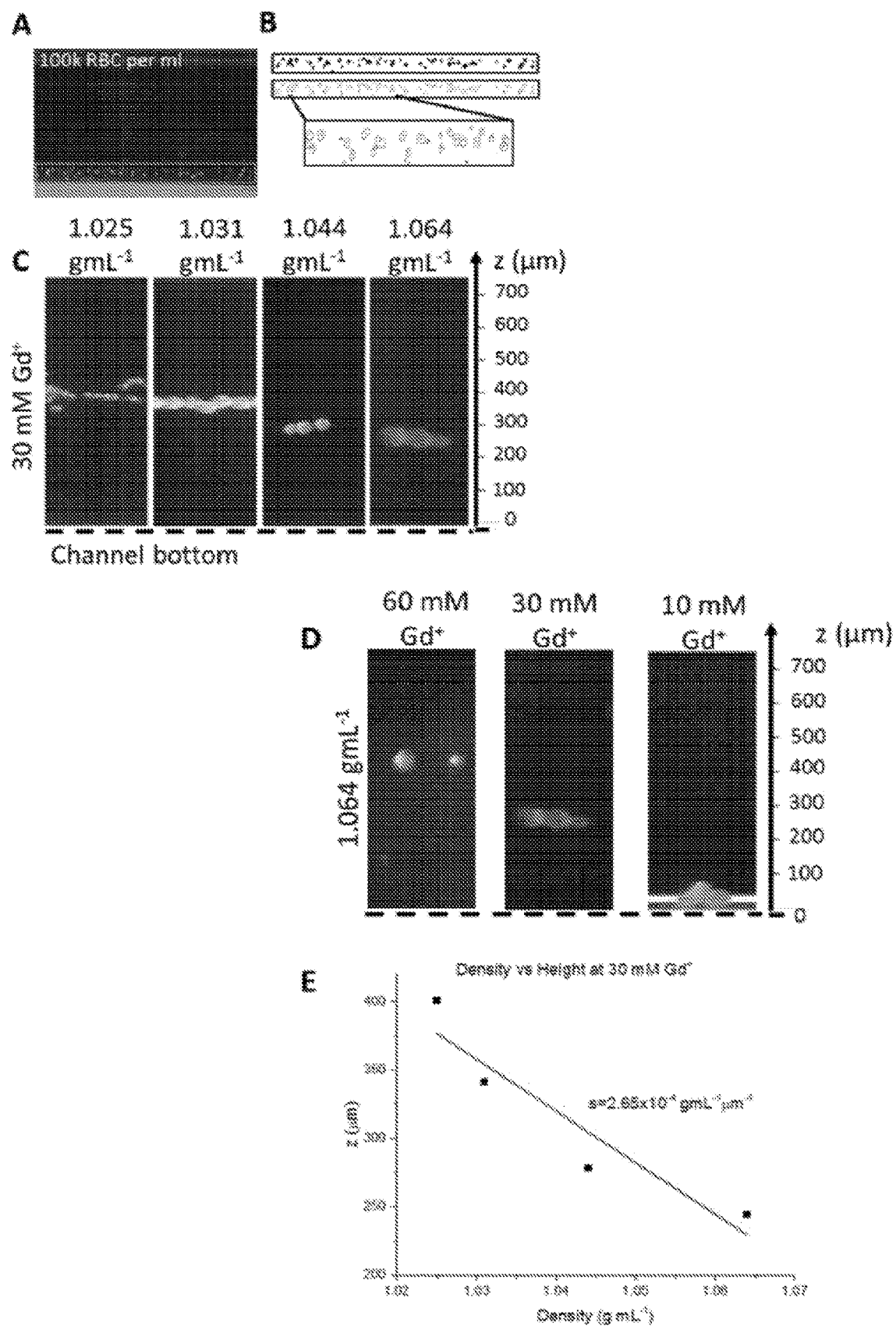
FIG. 4 illustrates single cell detection and density measurements.

Using the i-LEV platform, single cells were detected without using any labels. After diluting the RBC concentration to 100,000 cells/mL or lower, individual cells in the illuminated area were quantified using simple image processing tools as illustrated in FIGS. 4A-4B. Finally, polyethylene beads were levitated in the capillaries to check the levitation resolution of the platform and show its potential to calculate densities for different samples and cells. Beads with various sizes between 10-100 µm in diameter with densities of 1.025 g mL$^{-1}$, 1.031 g mL$^{-1}$, 1.044 g mL$^{-1}$ or 1.064 g mL$^{-1}$ showed distinct levitation heights in 30 mM Gd$^+$ as illustrated in FIG. 4C. It was also observed that beads with 1.064 g mL$^{-1}$ density had different levitation heights in different Gd$^+$ concentrations (10 mM, 30 mM, 60 mM) as illustrated in FIG. 4D.

Earlier studies have introduced several relevant biological applications for different magnetic levitation systems. Here, i-LEV is presented which represents a novel platform combining magnetic levitation with a smartphone device. The i-LEV system reliably analyses blood cell counts and can also detect individual cells. It is a rapid, portable, easy to use and affordable platform that leverages the availability of smartphones to address a medical need and count RBC as well as WBC from unprocessed whole blood. In the state of the art at present, blood processing is a clinical procedure and requires extensive materials and equipment, as well as trained professionals. Therefore, it can currently not be implemented in the POC setting. The disclosed system could, however, enable blood analyses from home and facilitate disease diagnosis and monitoring.

The i-LEV device can also perform fluorescent imaging, as the set-up carries several slots to insert fluorescent LEDs, lenses, excitation filters and emission filters as seen in FIG. 1C. Although, the current platform is static, it can be extended to enable dynamic flow experiments and monitor real-time effects of drugs on certain cell types that have been separated within capillaries. Additional applications of the system may include advanced tests, for example, to monitor circulating blood cells or sickle cell disease, especially in resource-constrained settings. Levitation systems integrated into smartphones could provide simple blood tests for large populations as smartphones are extensively used across the world. It is estimated that globally, approximately 5 billion people use mobile phones. In this respect, smartphone integrated medical technologies such as i-LEV could potentially play an important role in health services, particularly in developing countries with limited financial and logistical resources.

Figure 14:
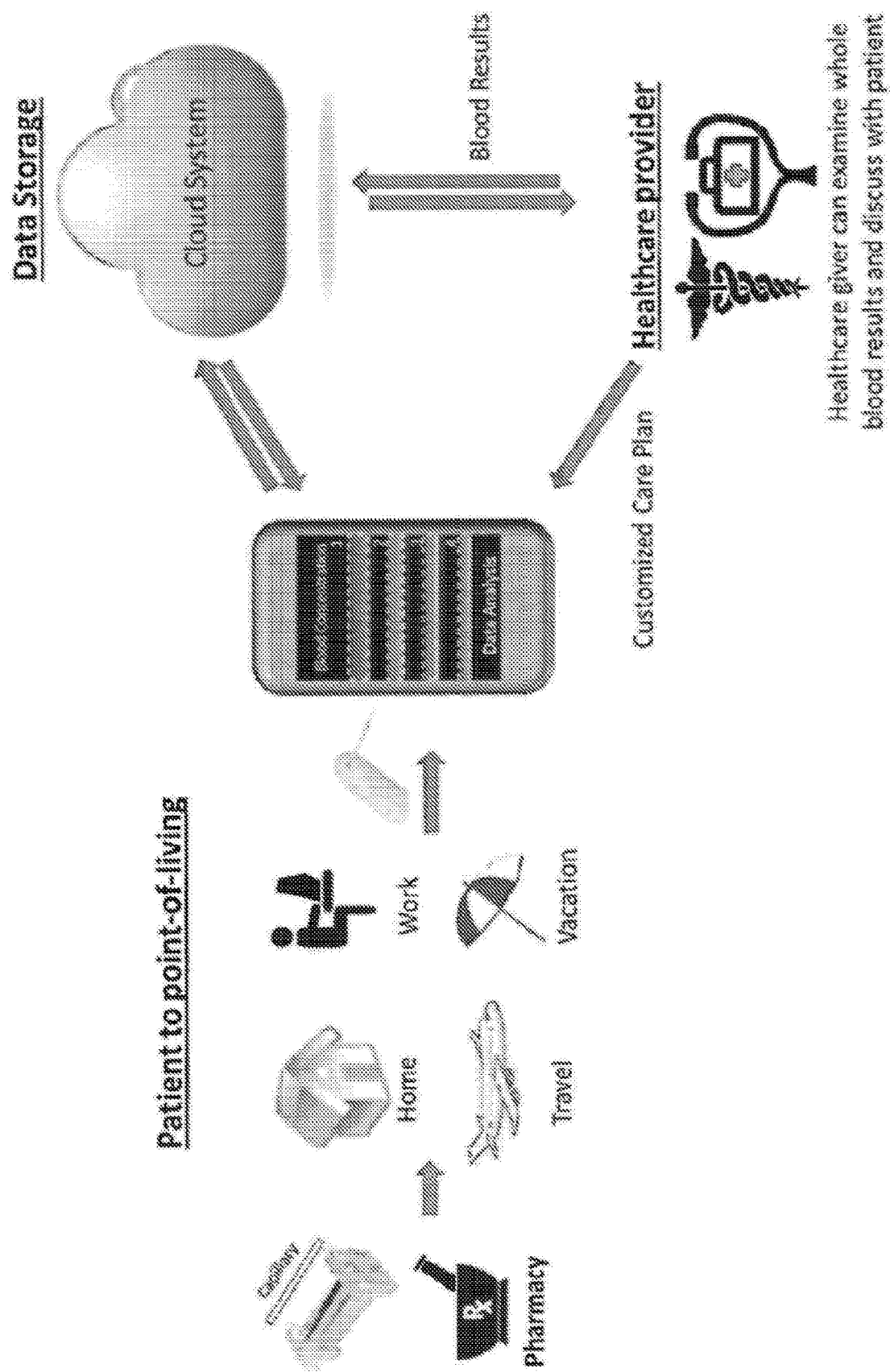
FIG. 14 is a diagram showing how i-LEV could be implemented and contribute to the healthcare system. Blood counting can be performed with an integrated mobile application at various settings (i.e., at home or work, or during travel or vacation). The mobile application reports the measurements to the healthcare provider. The healthcare provider analyzes the results and provides feedback through an online system.

The i-LEV test results can be analyzed and evaluated using an app and can also be transferred to healthcare providers via integrated cloud platforms as illustrated in FIG. 14 schematically. The portability, affordability and simplicity of this platform results in an easy-to-use set-up for blood counting in home settings, as well as biological or clinical laboratories.

This type of magnetic levitation-based diagnosis system can be used in various different types of applications. As one example, blood counting for several disease diagnosis and monitoring could be performed. As another example, white and red blood cells may be separated for accessing diseases like sickle cell anemia, thalassemia, and chronic fatigue syndrome. Still yet, this technology could be applied to address further medically relevant questions using a POC approach to diagnose and monitor diseases. For example, it has previously been shown that cells infected by viruses have distinct levitation characteristics, representing another promising application for the i-LEV system once again particularly relevant for developing countries.

The device utilize smartphone capabilities which enables portable, rapid, label-free, easy-to-use and affordable blood counting and analysis at home-settings as well as various resource-limited settings. Capabilities of smartphone levitation device combined with continuous sample flow enables high throughput isolation of cells of interest at resource constrained settings.

Some additional examples are now provided to illustrate the proof-of-concept that the cell phone-based magnetic levitation system version of i-LEV could be extended variety applications including (1) monitoring the effect of drugs, metabolites, chemicals; (2) studying the mechanobiology of cells under different conditions; and (3) studying embryo and oocyte differentiation and accessing the health of embryos/oocytes.

Example II: Monitoring the Effect of Drugs Using Levitation Device

Figure 7:
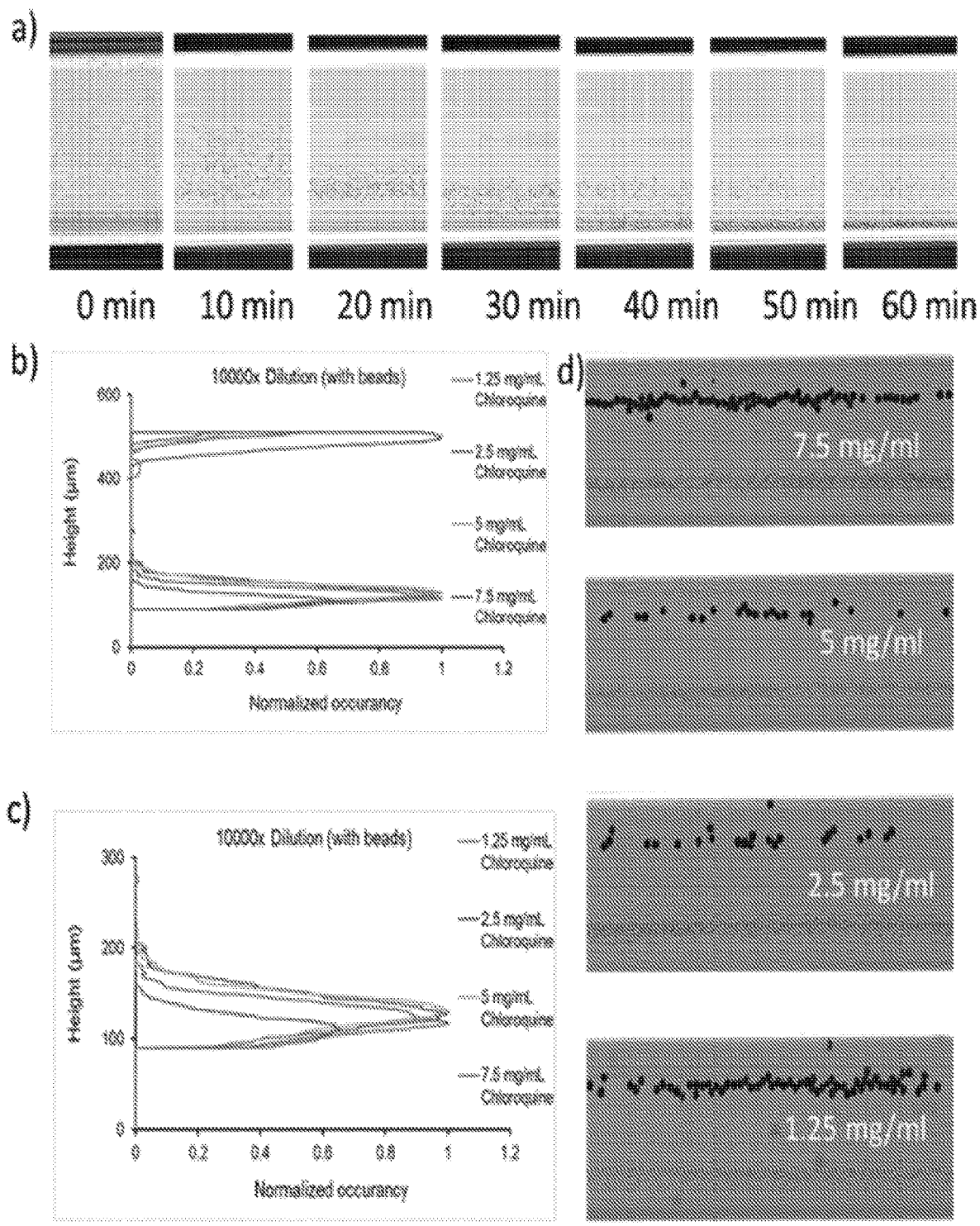
FIG. 7 shows the monitoring effect of drugs using a levitation device, specifically the effect of a malaria drug (chloroquine) on red blood cells.

Referring now to FIG. 7, the effect of drugs was monitored using the levitation device. The levitation system was specifically used to study the effect of a malaria drug called chloroquine on red blood cells. In FIG. 7A, 75 mg/mL of chloroquine was spiked into red blood cells and their levitation was monitored with an i-LEV device. It can be seen that, with increasing time of exposure, the levitation height of red blood cells decreases upon addition of chloroquine to the blood sample. The effect of different concentrations of chloroquine on whole blood was also imaged as is depicted in FIGS. 7B-7D, from which it can be seen that 1.5 and 7.5 mg/mL have similar effects while 2.5 and 5 mg/mL are similar. In FIGS. 7B and 7C (FIG. 7C being a zoomed in graph of a section of FIG. 7B), chloroquine concentrations of 1.25, 2.5, 5 and 7.5 mg/mL are spiked into blood and levitation heights of these images were analyzed. FIG. 7D illustrates the actual images that were analyzed to produce the plots of FIGS. 7B and 7C. In FIG. 7D, a certain density beads was added each time for calibration experiments.

Figure 8:
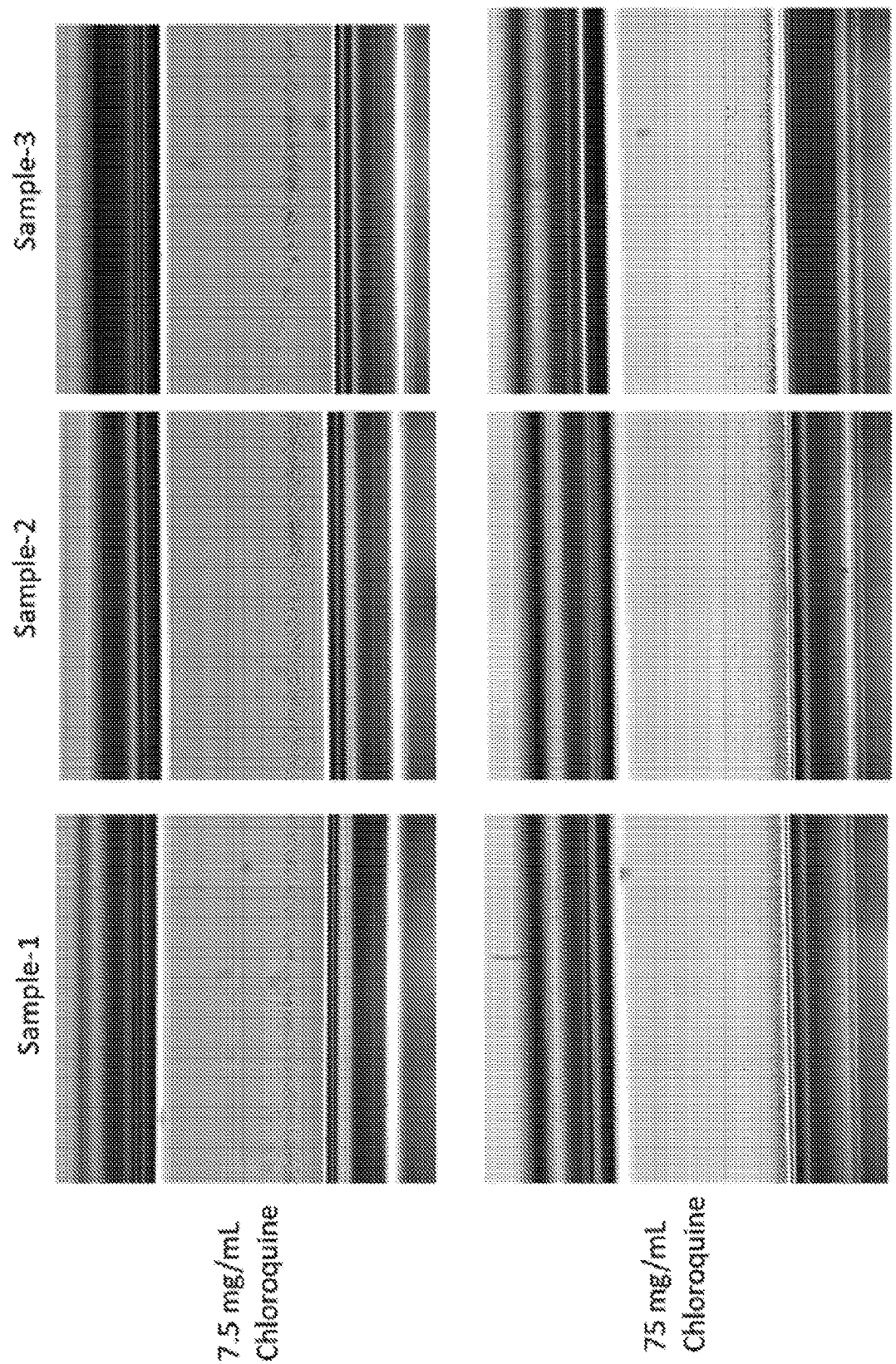
FIG. 8 shows the differential responses of various blood samples to chloroquine.

Turning now to FIG. 8, the responses of different blood samples (i.e., different blood samples "Sample-1", "Sample-2", and "Sample-3") are illustrated for the administration of chloroquine at 7.5 mg/mL and 75 mg/mL, the latter being a very high concentration of the drug. As can be seen, the blood sample levels out at a very low height within the capillary channel, especially after the high dosage treatment. The magnetic levitation system thus provides a quick way to see the drug effect on different blood types.

Figure 6:
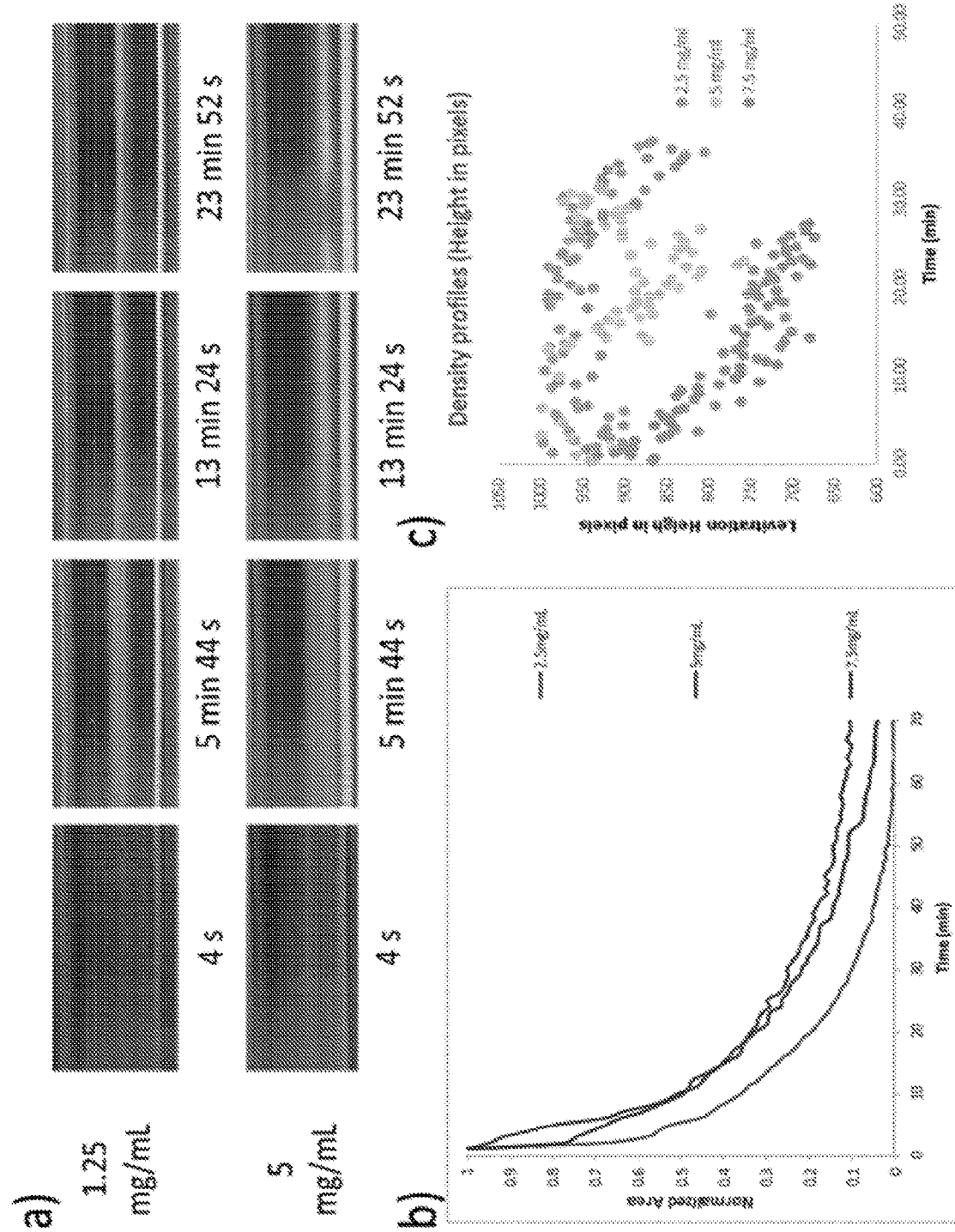
FIG. 6 shows the monitoring effect of chloroquine on RBCs using the cell phone based levitation system.

Still yet, FIG. 6 shows the monitoring effect of chloroquine on RBCs using cell phone based levitation system (i-LEV). In the i-LEV, increasing concentrations of chloroquine resulted in a smaller area. Images were taken over time in 60 minutes. As illustrated in FIG. 6A, initially 24 minutes are shown using 1.25 and 5 mg/mL of chloroquine concentration. FIG. 6B is then a graph showing the area analysis. Area of the blood were measured using an imageJ script developed in the lab. Area shows the viability of the cells. As the cells apoptosis with time, area gets smaller. Looking at FIG. 6C, the levitation height is measured using same script. Height is directly correlated with density of cells. Higher drug concentration leads to higher density of blood within 50 minutes.

Example III: Mechanobiology Studies Using the Levitation System

Figure 9:
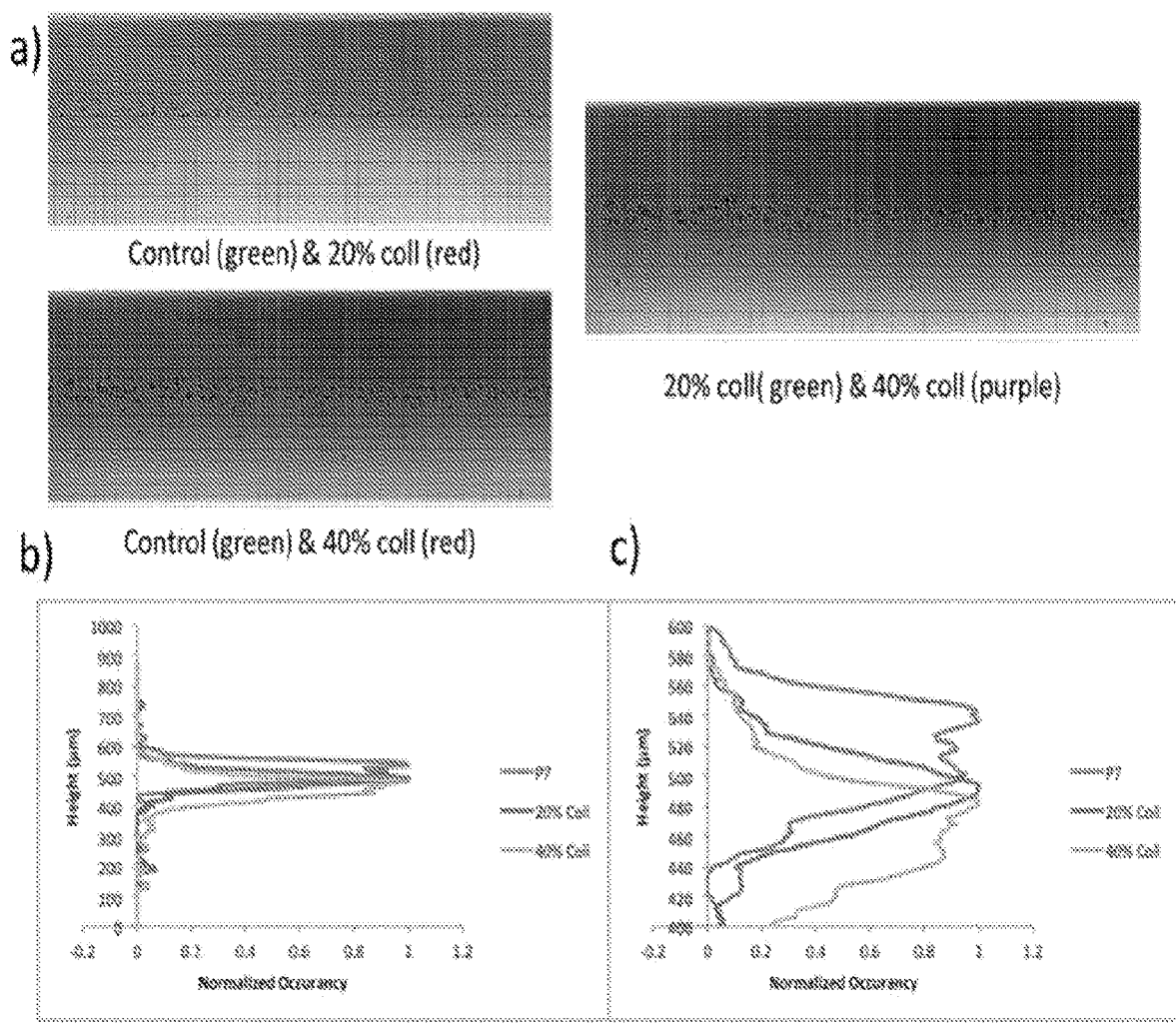
FIG. 9 illustrates the use of the levitation system for performing mechanobiology studies.

FIG. 9 shows the use of the levitation system, in mechanobiology studies. In FIG. 9A, breast cancer cells were placed in different collagen gels. 20% and 40% of collagen concentrations were used in this study. In this case, overlaid image won't be able to tell much details; however, in FIG. 9B (and the zoomed-in detail of FIG. 9B provided in FIG. 9C), density plots provide more details and enable saddle differences to be seen. Thus, the i-LEV device could be used for cell mechanics studies, including aging and stem cell differentiation.

Example IV: Embryo Differentiation Studies and Assessing the Health of Embryos

Figure 10:
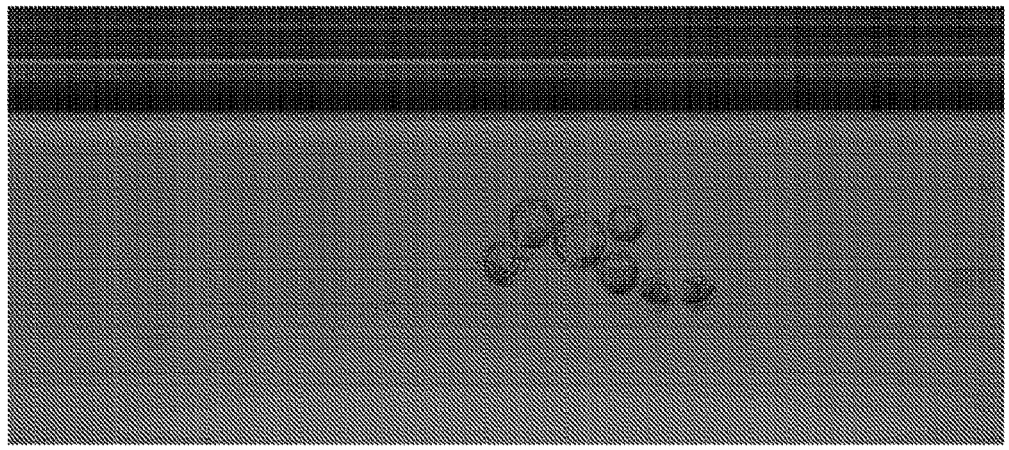
FIG. 10 illustrates the use of the levitation system for studying embryo differentiation and accessing the health of embryos.

Turning now to FIG. 10, the levitation system is shown being used to study embryo differentiation and access the health of embryos. Mixed populations of embryos were levitated at different days. The density of each embryo decreased over time. Accordingly, this system could be applied to monitor and understand healthy embryos which are levitated at different height.

Example V: Updated Rendering of i-LEV Design

Figure 12:
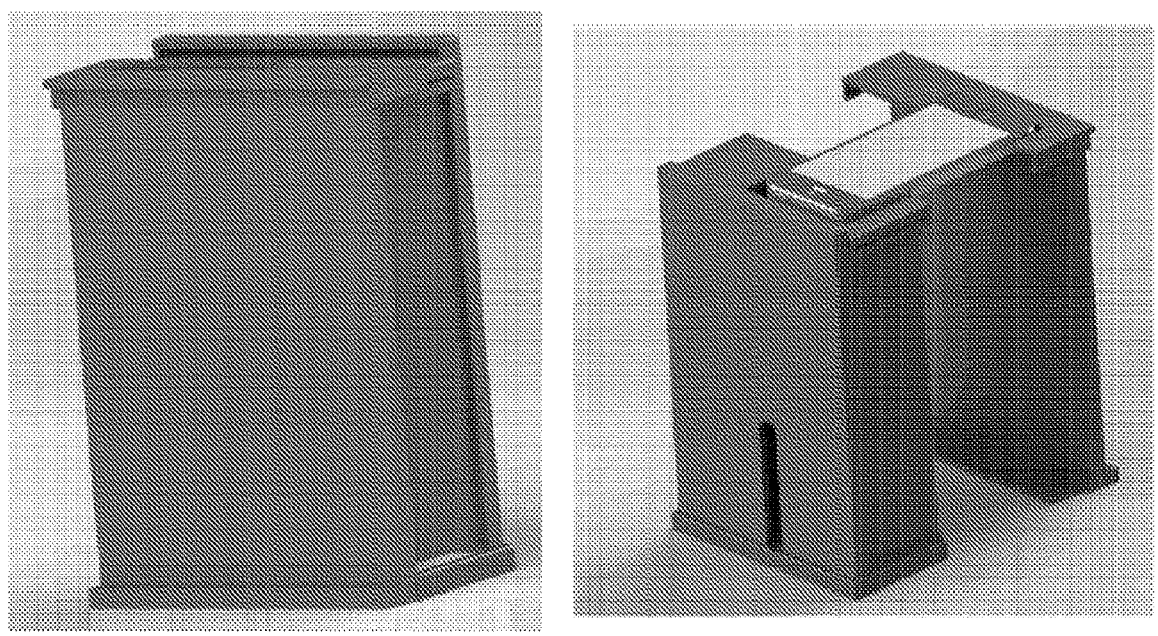
FIG. 12 illustrates a newer i-LEV design combining many of the features in more portable and compact way.
Figure 13:
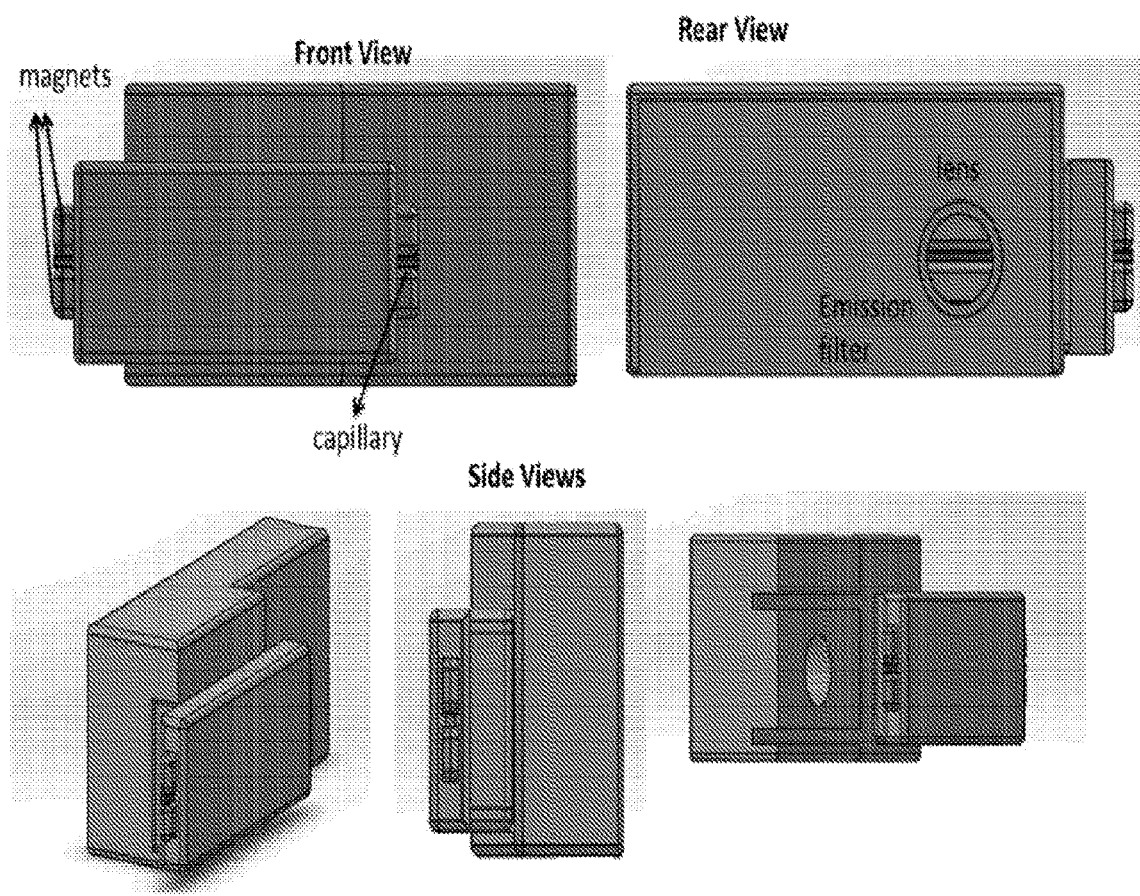
FIG. 13 illustrates another, updated design of the i-LEV for cell phone based imaging.

FIG. 13 illustrates yet another updated design of the i-LEV device for cell phone based imaging. In FIG. 13, a design is shown without mirrors and which more compact that earlier version found in FIGS. 1, 11 and 12. It will be appreciated that a magnetic levitation-based diagnosis system could take many physical forms.

High Throughput Magnetic Levitation Cell Separation

Figure 15:
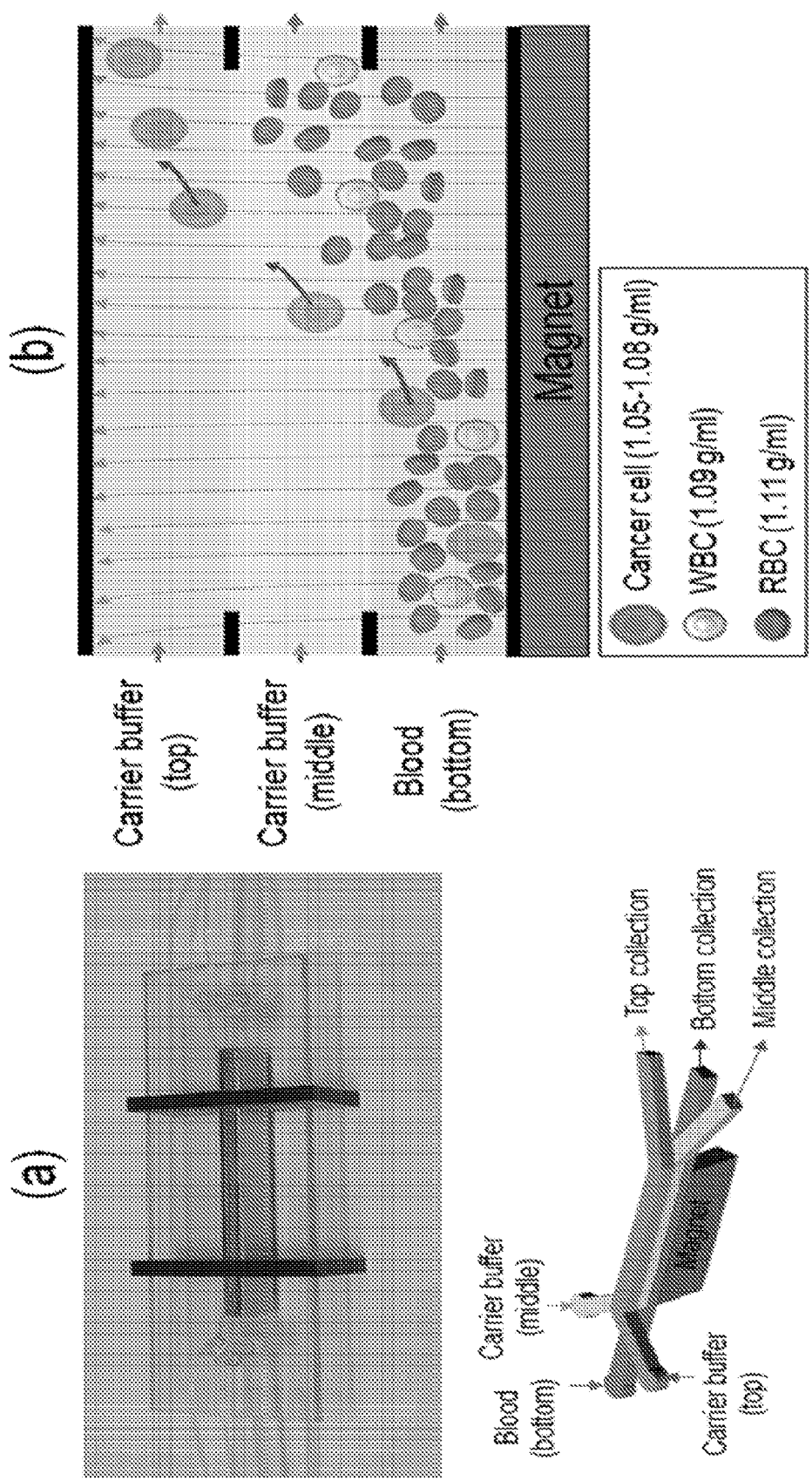
FIG. 15 depicts the design and principle for a platform for high throughput magnetic levitation cell (or other moiety) sorting.

The design and principle of the platform for high throughput magnetic levitation cell sorting are schematically shown in FIGS. 15A and 15B. The platform includes a microchannel connected to three sets of inlets and outlets, which are configured from top to bottom (top/middle/bottom), and a single neodymium magnet is placed underneath the bottom substrate of the microchannel. The microfluidic device is fabricated by assembling three different polycarbonate layers, each of which incorporate a microchannel cut formed by laser machining, using double-sided adhesives. After the chip assembly, a tubing (Tygon® microbore tubing, 0.010) is connected to inlet and outlet ports followed by the placement of a magnet using two PMMA holders. A blood sample spiked with paramagnetic gadolinium ($Gd^+$) is continuously introduced into the platform through the bottom inlet using a syringe pump at a constant flow rate, and a buffer solution with $Gd^+$ is separately infused through top and middle inlets.

Without the magnetic effect, particles are allowed to migrate between three different fluid flows only by diffusion, due to the laminar flow property of a microfluidic flow. When the magnetic field is applied throughout the microchannel, the magnetic susceptibility difference between a cell or other moiety and the surrounding paramagnetic medium causes the cell to move away from a higher (i.e., close vicinity at the magnets) to a lower magnetic field strength site (i.e., away from the magnets). For example, since cancer cells have lower intrinsic densities and larger sizes than blood cells, CTCs are levitated even faster than other blood cells, which consequently allows CTCs to transfer into the top fluid flow, and to be separately collected for subsequent downstream analysis.

Example VI: Density Separation of Test Beads

Figure 16:
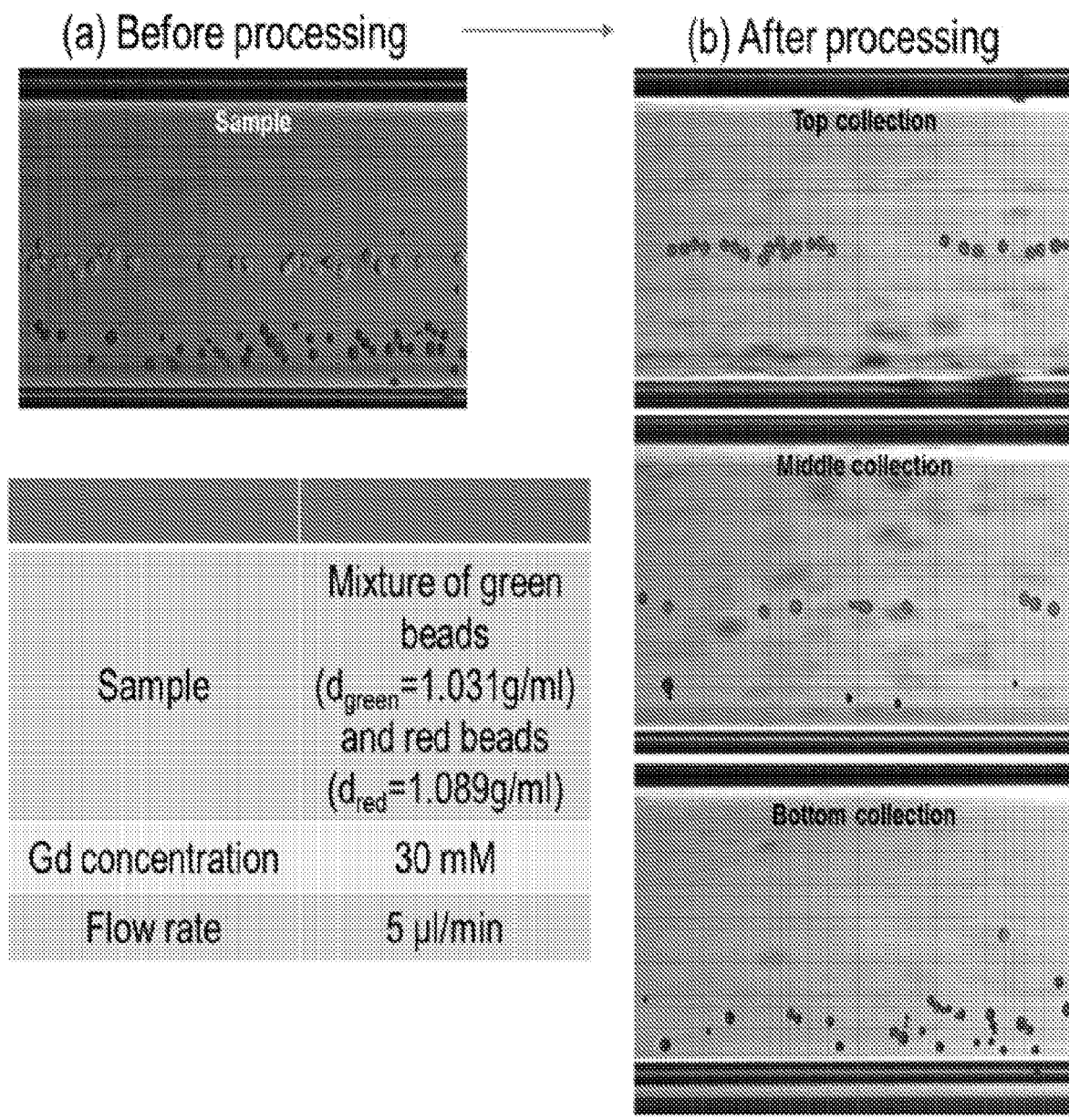
FIG. 16 depicts the experimental results of a high throughput magnetic levitation sorting device in which beads of different densities are sorted.

To test the system for separation and turning now to FIG. 16, the platform was tested for separation between two types of beads with different densities, green=1.031 g/ml (the upper band) and red=1.089 g/ml (the lower band). The sample mixture is shown before processing and collections in FIG. 16A and in FIG. 16B is shown in the top/middle/bottom outlets after processing in the magnetic levitation-based cellular imaging setup. Most green beads were collected from the top fluid flow, while most red beads were observed in the bottom collection, demonstrating the capability of the platform for particle separation by density.

Example VII: Density Separation of Breast Cancer Cells

Figure 17:
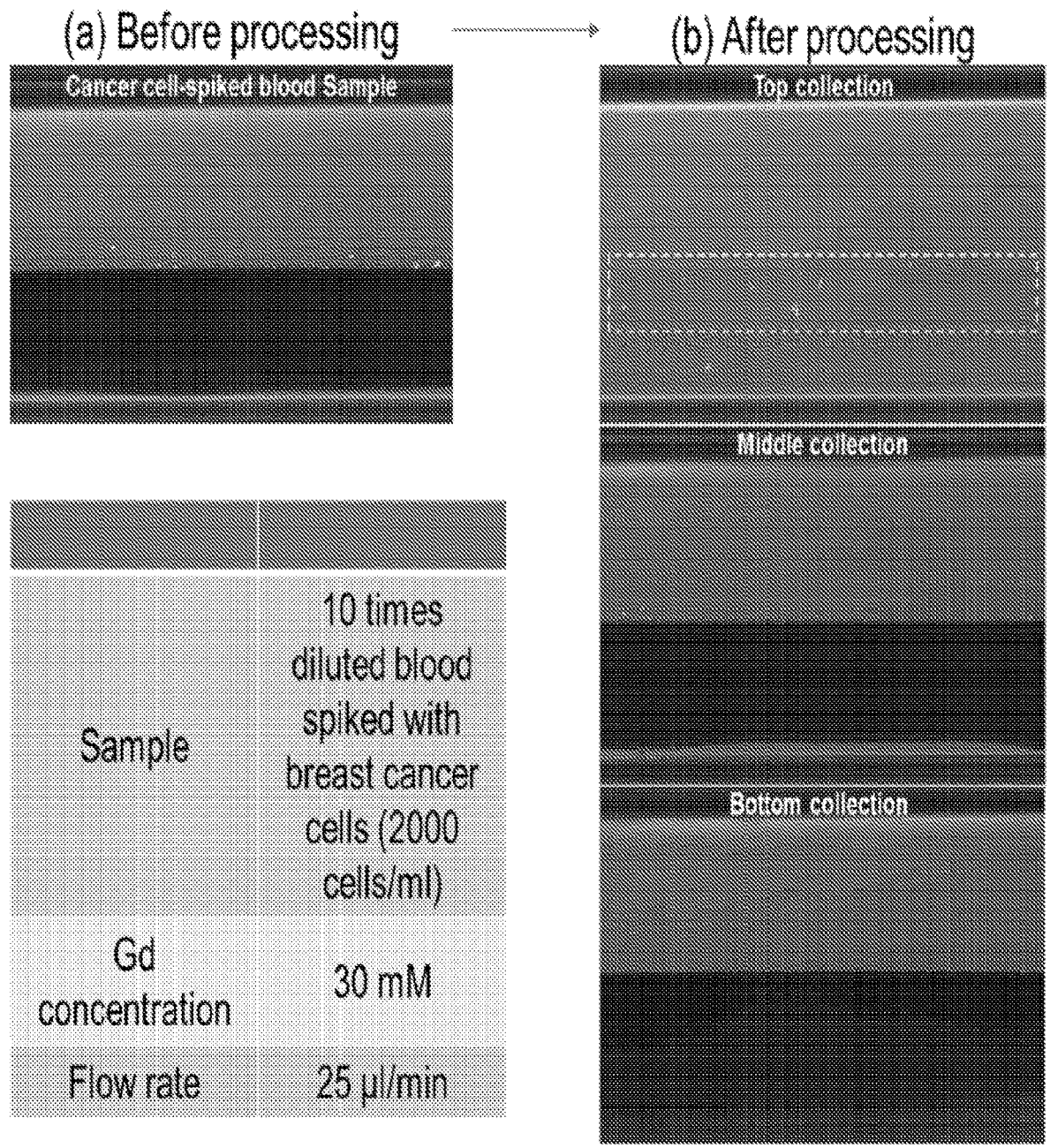
FIG. 17 depicts the experimental results of a high throughput magnetic levitation sorting device in which cancer cells are sorted out of a blood sample.

To test a more practical application and turning now to FIG. 17, the platform was tested using a 10 time-diluted blood sample spiked with a breast cancer cell (MDA-MB-231) at a concentration of 2000 cells/ml. FIG. 17A shows the sample before processing and collections and FIG. 17B shows the collections from top/middle/bottom outlets after processing were respectively introduced into the magnetic levitation-based cellular imaging setup. Most cancer cells were collected from the top fluid flow, in which other blood cells were depleted after the processing, demonstrating the isolation of cancer cells from blood without the use of antibody or additional labeling.

Example VIII: Alternative Two-Magnet Design

In one alternative design, the first microfluidic platform may incorporate a long, straight channel that divided into two near the outlet (i.e., top and bottom channels) by a thin film, connected to one inlet and two outlets. This device employs the principle of magnetic levitation to separate the cells based on their unique densities in a paramagnetic medium. For the device fabrication, polycarbonate sheets were first cut using a laser cutter and assembled using double-sided adhesive tape. The fabricated microfluidic chip is featured with 200 µm and 700 µm height bottom and top channel respectively. The first microfluidic design incorporates a long, straight channel that is split into two (top and bottom channels) by a thin film near the outlet, each of which is connected to an outlet, respectively. Two permanent NdFeB magnets are respectively placed on the top and bottom of the channel, with the same poles facing each other. Such a design for a magnetic levitation-based high-throughput blood cells sorting device can be found in FIG. 18, for example, which includes a pair of magnets.

Example IX: Plasma Blood Analysis

Figure 18:
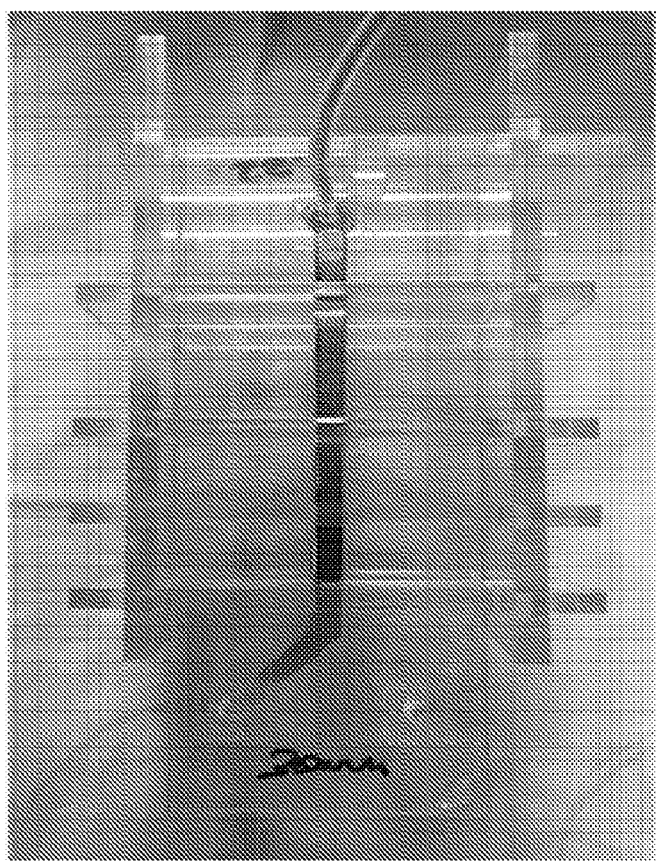
FIG. 18 depicts an alternative high throughput magnetic levitation sorting device.
Figure 18:
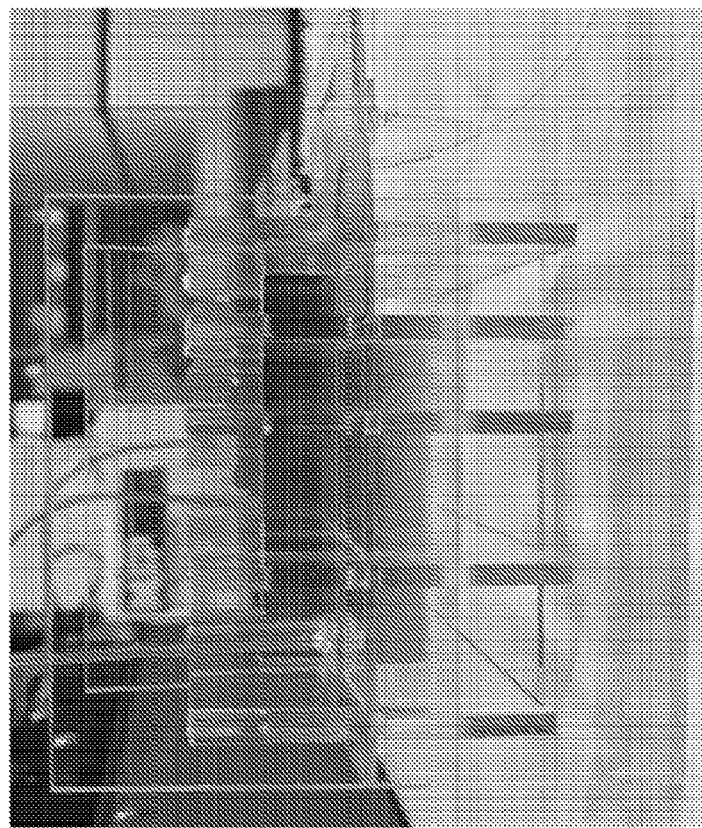
Figure 19:
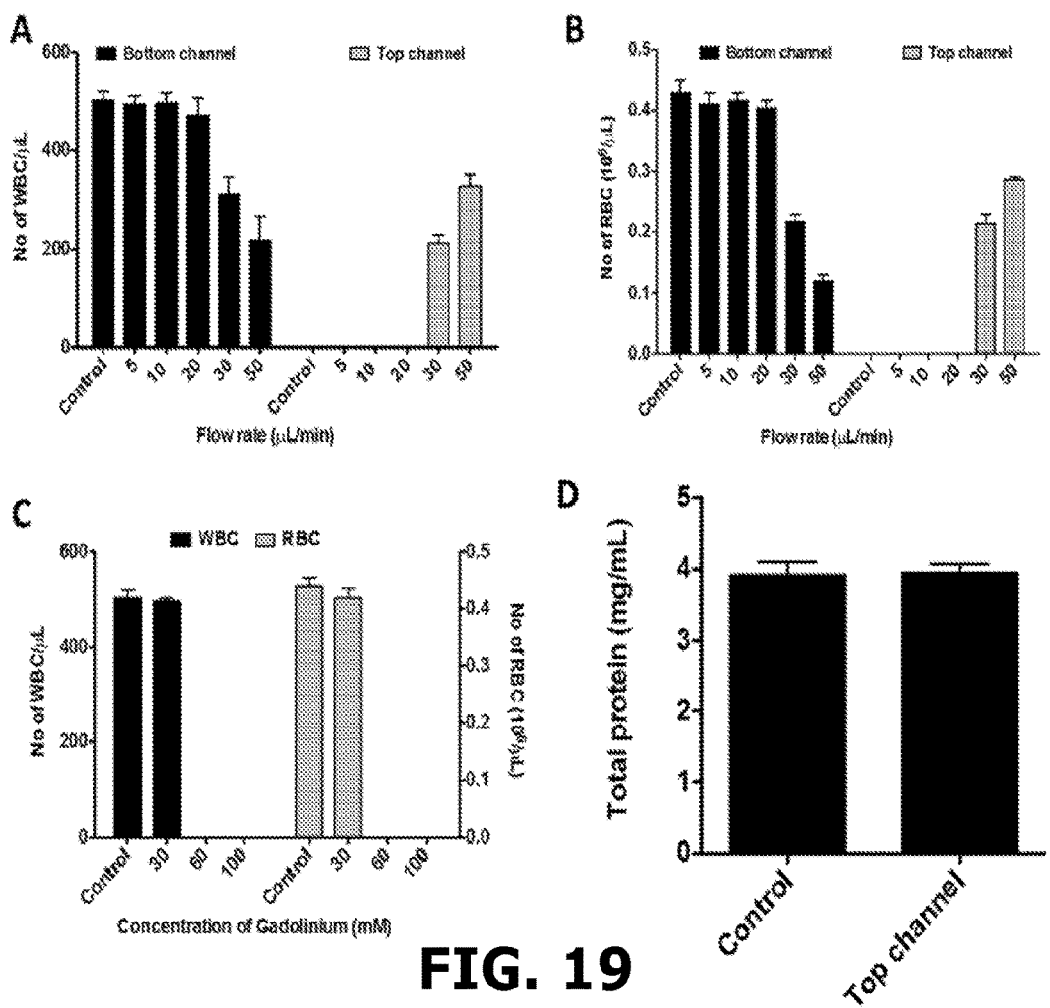
FIG. 19 illustrates the results of plasma blood analysis using a high throughput magnetic levitation sorting device.

Turning now to FIG. 19, plasma blood analysis is shown in such a device as depicted in FIG. 18. Referring now to FIGS. 19A, 19B, and 19C, at the flow rate of 5, 10, 20 uL/min blood cell sorting was observed, and blood cell was not recovered at top channel. Whereas, blood cell sorting was not found at higher flow rate such as 30 and 50 uL/min, since blood cells was also recovered at top channel. Due to the insufficient duration at higher flow rate, blood cells are not levitated and separated into homogeneous layer that cells are flowed on both channels. Thus, 20 uL/min is chosen as optimal flow rate for blood cell sorting in the exemplary system the tests were performed on. In FIG. 19D, total protein analysis of plasma collected from top channel and compared with plasma, which is separated by the centrifugation and it was found that the concentration of protein on plasma form the top channel is recovered as found in the traditional centrifugation method. It is concluded that under the optimized condition, the developed high throughput MagLev-based devices (i.e., those sorting devices previous described) is efficiently sorting the blood cells.

Example X: Fluorescence-Activated Cell Sorting (FACS) Analysis

Figure 20:
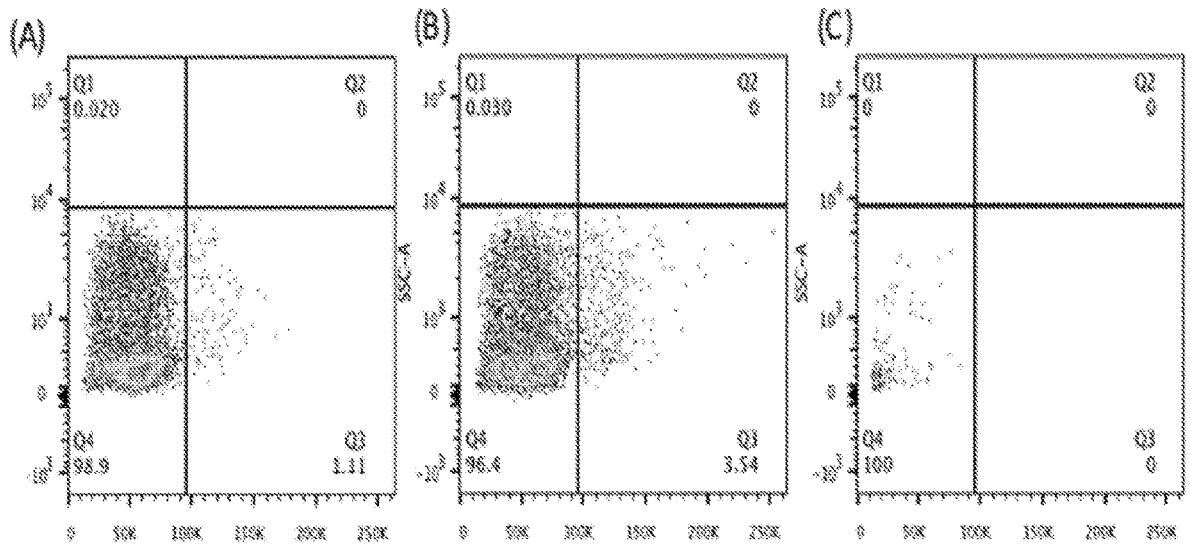
FIG. 20 illustrates fluorescence-activated cell sorting (FACS) analysis to establish the efficiency of the plasma separation.

Referring now to FIG. 20, plasma separation efficiency of Maglev based high-throughput blood cells sorting device was evaluated by fluorescence-activated cell sorting (FACS) analysis. Initially, whole blood and blood cells separated by Maglev device were stained with CD 45 Alexa 488 and CD 36 FITC antibodies, and subjected to FACS analysis. As shown in FIG. 20A, both RBCs and WBCs were observed in whole blood and, as shown in FIG. 20B, blood cells separated from bottom channel of the Maglev device, whereas at top channel of the device, blood cells were not observed as shown in FIG. 20C. The obtained results further conforms that under optimized conditions the developed Maglev device is able to separate the blood cells and plasma from whole blood.

Example XI: RBCs and WBCs Separation from Whole Blood

Figure 21:
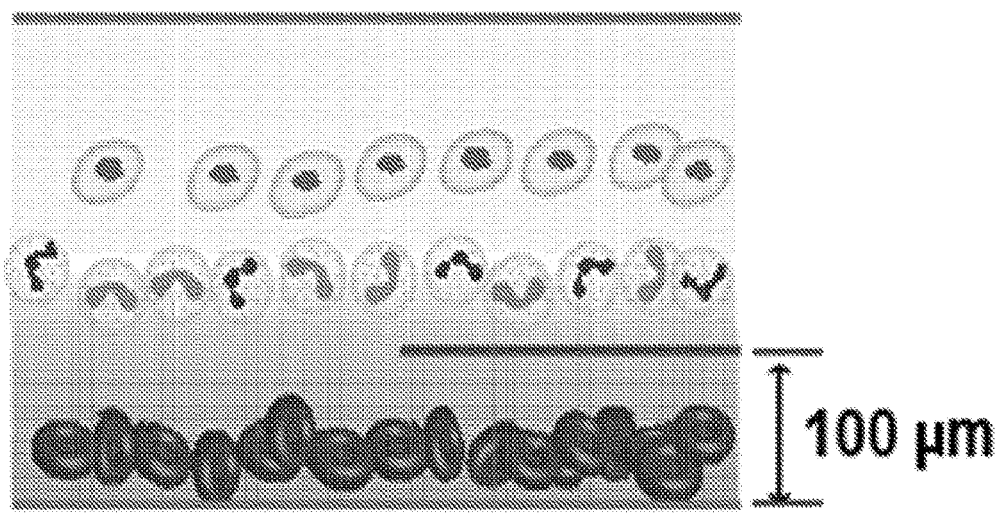
FIG. 21 illustrates the separation of RBCs and WBCs from whole blood.
Figure 21:
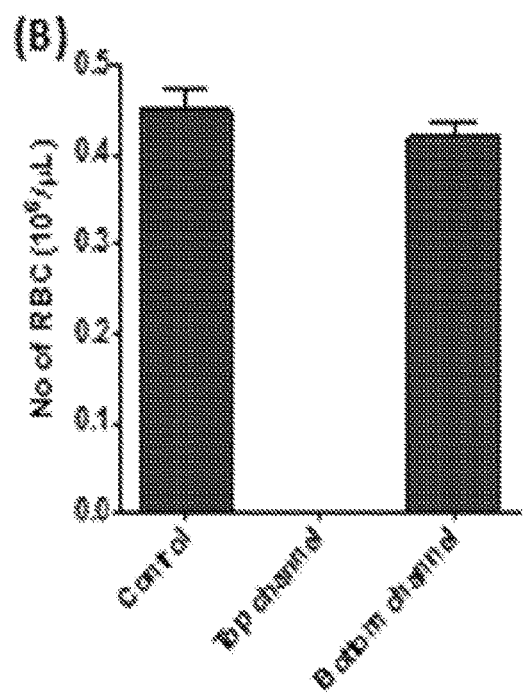
Figure 21:
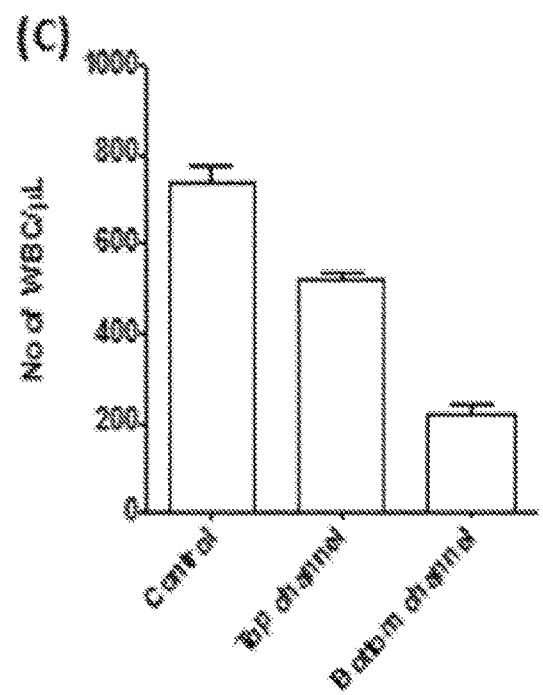

Turning now to FIG. 21, the developed Maglev device was also used to separate RBCs and WBCs from whole blood to show the ability to isolates the rare cells from whole blood, since the density of the rare cells is relatively equal or higher than the WBCs. In order to separate blood cells, height of the bottom channel was reduced into 100 µm, and the divider was assembled between the bottom and top channel as illustrated in FIG. 21A. Upon levitation, all the RBCs were flowed through the bottom channel that were levitated below 100 µm height, and they were not found at top channel as indicated in FIG. 21B. FIG. 21C also indicates that about 70% of WBCs were collected from the top channel, which may due that most of the WBCs are levitated higher than 100 µm height that flows through the top channel. The obtained results proved that the developed high throughput MagLev device is able to isolate rare cell, such as CTCs and fetal red blood cells from whole blood and tumors.

Example XII: Sorting Cancer Cells in Blood

When a mixture of cell types are flowing along the channel, the magnetic field gradient created by two permanent magnets separates individual cell types into a unique vertical position inside the channel determined by the density of the cell. For example, cancer cells can be easily separated from a complex mixture (i.e., blood) due to their large intrinsic density difference. In the disclosed microfluidic design, CTC/CTM that are typically levitated above blood cells can be collected from the top channel. We first tested the platform for plasma separation, in which whole blood sample with 30 mM $Gd^{3+}$ is flowed through the channel at a constant flow rate, 20 µL/min. Under the magnetic field, cells are moving from high magnetic induction to low, and levitated in a specific height in the channel according to their density signature. Due to the high density, blood cells RBCs and WBCs were flowed below the divider and collected at bottom outlet, while plasma flows above and collected from top channel outlet. Similarly, by reducing the bottom channel height into 100 µm, WBCs were separated and collected from the top channel, which shows the potential of this device that can also separate the CTCs from the whole blood sample.

Example XIII: Cell Separation/Blocking Using a Magnetic Field

Figure 22:
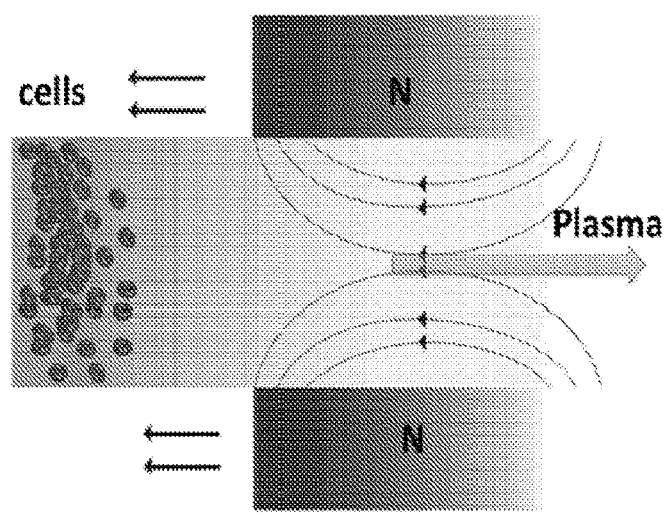
FIG. 22 depicts a schematic of cell separation from plasma in blood using a pair of magnets in an anti-Helmholtz configuration in which the magnets separates the cells from the plasma.

Turning now to FIG. 22, a third design and principle of this platform are shown in schematic diagram. The present Maglev based plasma separation employs the principle of high magnetic field induced cell blocking at high concentrated paramagnetic medium. While blood sample flowed into the channel, due to high magnetic field at edge of the magnate that creates high magnetic induction in the paramagnetic medium, cells move into low induction site and stacked in inlet chamber. The microfluidic channel may be a long straight channel featured with 1 mm height, 50 mm length and 4 mm width which connected with one inlet and outlet. The presented microfluidic plasma separation device is fabricated using a simple micro-fabrication using a polycarbonate sheet is cutting with laser cutter with desired channel feature, and assembled using a double side adhesive tape. Two permanent neodymium magnets are placed on top and bottom of the channel as same pole facing to each other. For the plasma separation experiment, a paramagnetic medium gadolinium ($Gd^{3+}$) spiked blood sample is flowed in to inlet using a syringe pump at a constant flow rate. Due to high magnetic induction at near the magnetic edge, cells are blocked, and stacked back in inlet chamber and allows only plasma into channel that was collected at outlet.

Figure 23:
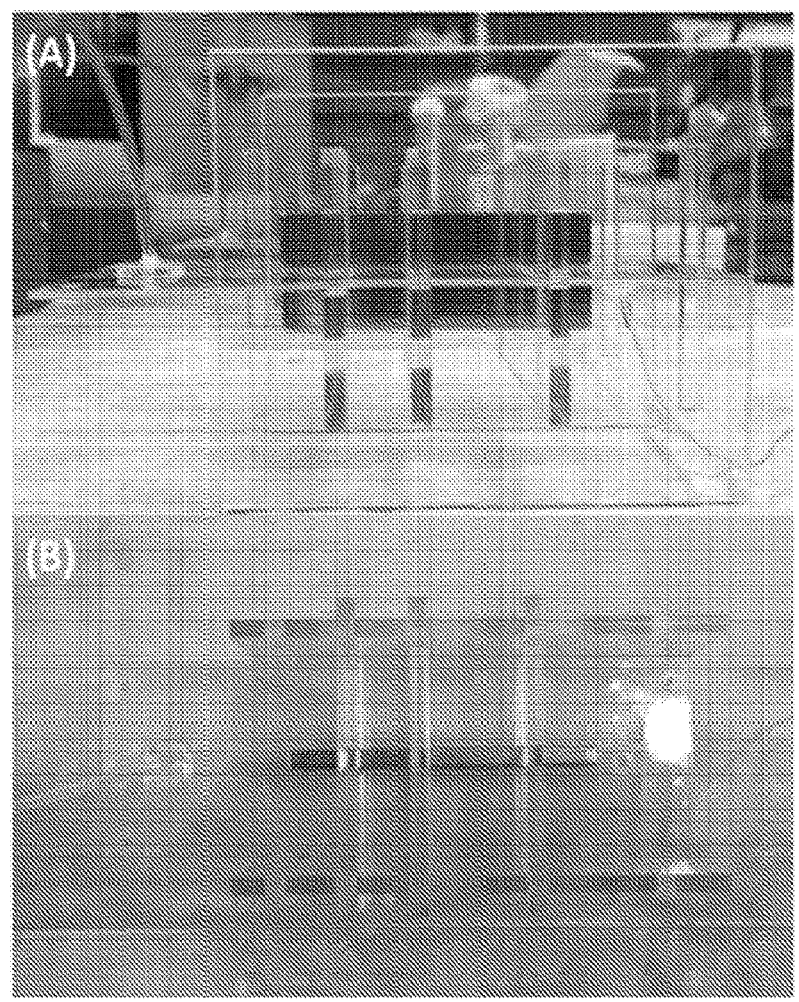
FIG. 23 is a high magnetic induction induced cell blocking based plasma separation device.
Figure 24:
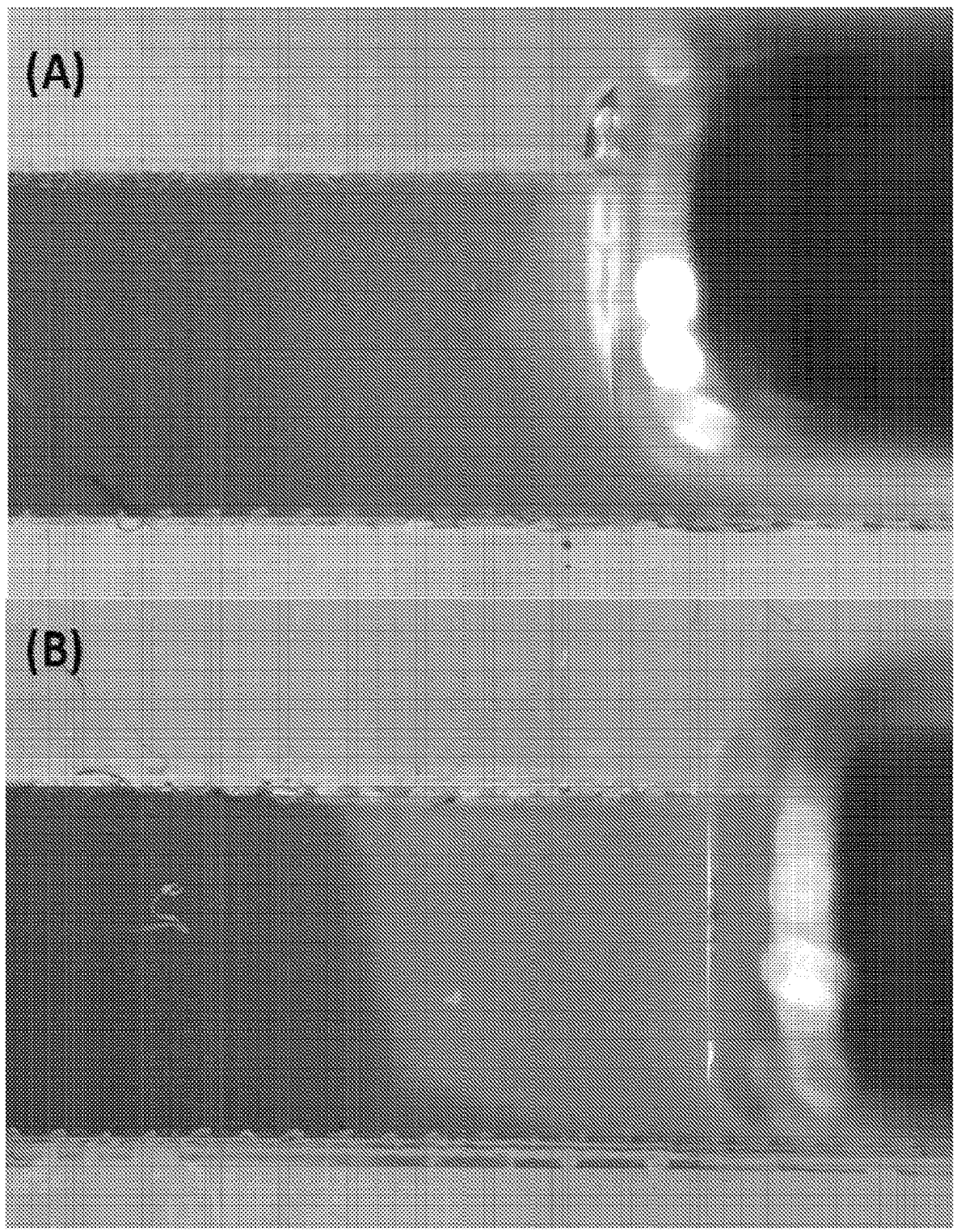
FIG. 24 are detailed views illustrating the optimization of the paramagnetic medium Ga$^{3+}$ concentration for efficient plasma separation from blood sample at 50 mM Ga$^{3+}$ (FIG. 24A) and 100 mM Ga$^{3+}$ (FIG. 24B) using the device of FIG. 23.
Figure 25:
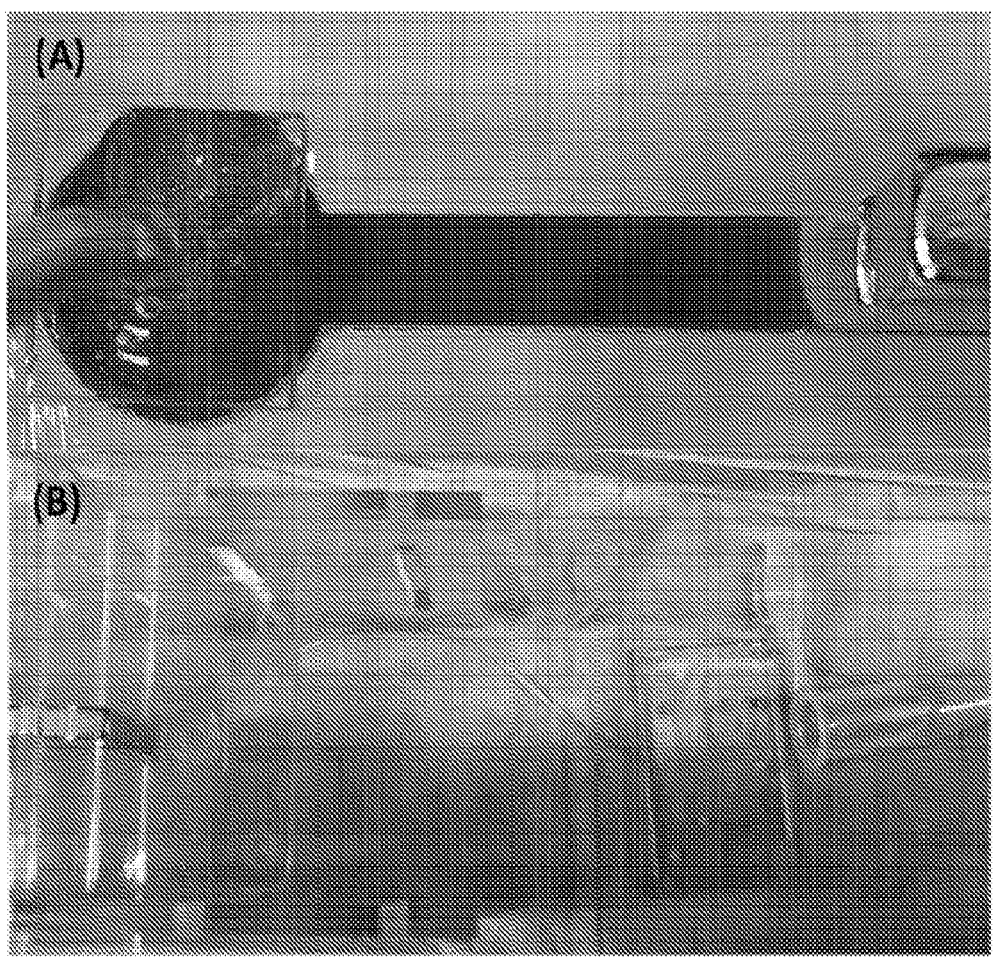
FIG. 25 illustrates, in FIG. 25A, the loading of the blood sample into the inlet of the device of FIG. 23 and, in FIG. 25B, the plasma exiting the outlet.

In FIG. 23, high magnetic induction induced cell blocking based plasma separation device is shown in a side view (FIG. 23A) and a top view (FIG. 23B). FIGS. 24 and 25 shows the optimization of paramagnetic medium $Gd^{3+}$ concentration for efficient plasma separation from blood sample. In FIG. 25A, the blood is shown being loaded into the cell blocking based plasma separation device (i.e., the MagLev), in FIG. 24 detailed views are shown illustrating the blocking, and FIG. 25B shows the plasma collection at outlet (from 100 mM Gd$^{3+}$ spiked 10 time diluted with PBS blood sample flowed at constant flow rate, 20 μL/min according to the experiment described below).

In this experiment, 10 times diluted with PBS whole blood spiked with 50 mM Gd$^{3+}$ (in FIG. 23A) and 100 mM Gd$^{3+}$ (in FIG. 23B) was flowed at a constant rate, 20 μL/min through the device of FIG. 22. As shown in FIG. 24, the magnetic repulsion force is increased with increasing the concentration of Ga$^{3+}$, which creates high magnetic induction that blocks the cell effectively as compared to low concentration of 50 mM Gd$^{3+}$.

Multi-Cellular 3D Assembly Based on Magnetic Signatures and Simulation of Microgravity Magnetic levitation can be used to rapidly create multi-cellular 3D cell assembly with controlled shape. This method could surpass conventional 2D tissue culture by offering cell culturing conditions able to mimic the in vivo cell-cell and cell-ECM interactions and organization. Compared to other methods, the magnetic levitation methodologies described herein do not require engineered scaffolds or magnetic nanoparticles (for levitation). Assembled cell aggregates can be used for tissue engineering, disease modeling, drug-screening and cell/tissue biology study.

Among other things, this system could enable studies to investigate how the microgravity affects cell biology for space applications, without using expensive and complicated research equipment. It could allow genomic, transcriptomic and proteomic analysis of cells under microgravity conditions.

Among other things, this method allows sorting, recovery and characterization exploiting both magnetic/density properties and imaging/molecular profiling. Cells, that are magnetically separated in the device can be removed and characterized both with live and non-live imaging methodologies (for example, transmitted light, fluorescent microscopy, immunostaining) in absence of magnetic field, but without losing the magnetic/density sorting. In addition, cells of interests can be selectively recovered from the levitation device for analysis (for example, genomic, transcriptomic and proteomic) or further culturing, depending on the imaging method. This method can be broadly used for cell/tissue biology study. It is also envisioned that this method could be also applicable to objects different than cells.

Example XIV: Spheroid Assembly Method

Figure 26:
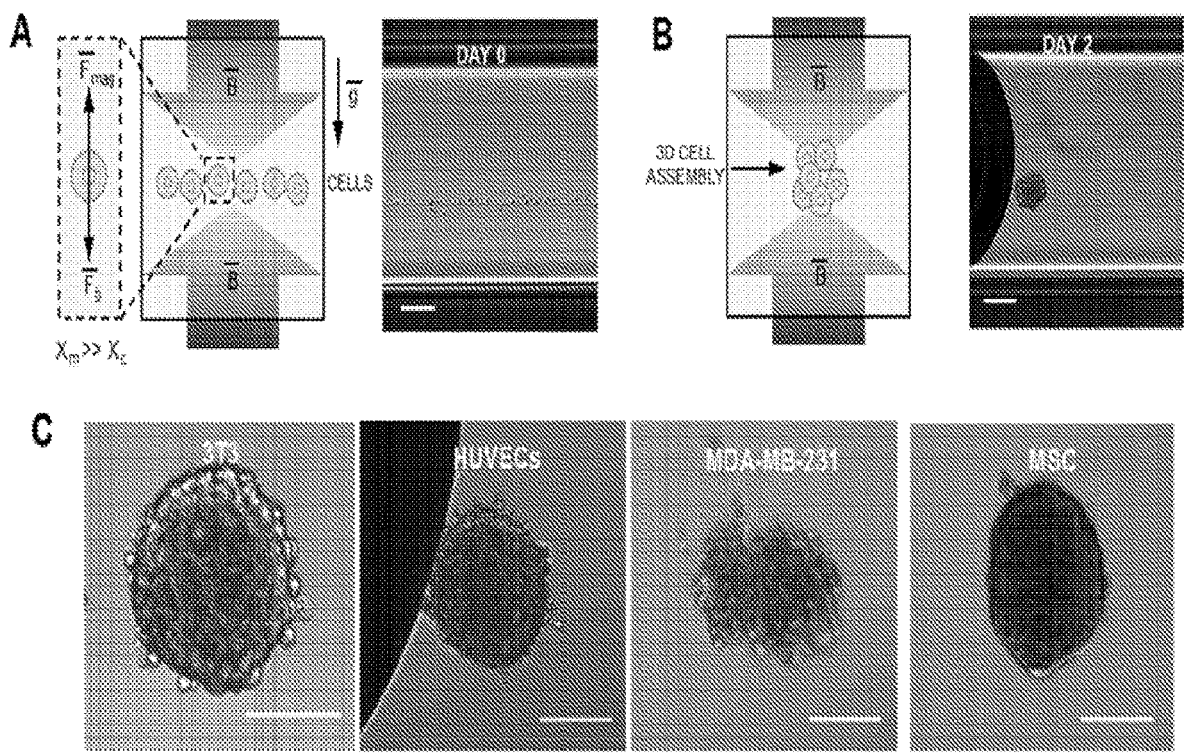
FIG. 26 illustrates a spheroid assembly method.

FIG. 26 illustrates a spheroid assembly method. With reference being made to FIGS. 26A and 26B, thanks to the magnetic induction (B) and gravity (g) cells levitate and are focused in an equilibrium plane where magnetic forces ($F_{mag}$) and buoyancy force ($F_b$) balance each other. Magnetic susceptibility of the medium ($\chi_m$) is larger than the cells' magnetic susceptibility ($\chi_c$). As illustrated comparatively between the Day 0 and the Day 2 images in FIGS. 26A and 26B, during levitation, cells self-assemble into stable spherical aggregates with time. FIG. 26C provides images of various cell types NIH-3T3, GFP Human Umbilical Vein Endothelial Cells (GFP-HUVEC), MDA-MB-231 and Mesenchymal Stem (MSC). Cell concentration was 50 thousand cells/ml at 50 mM Gd$^+$ in cellular medium. The white scale bar is 100 μm.

Figure 27:
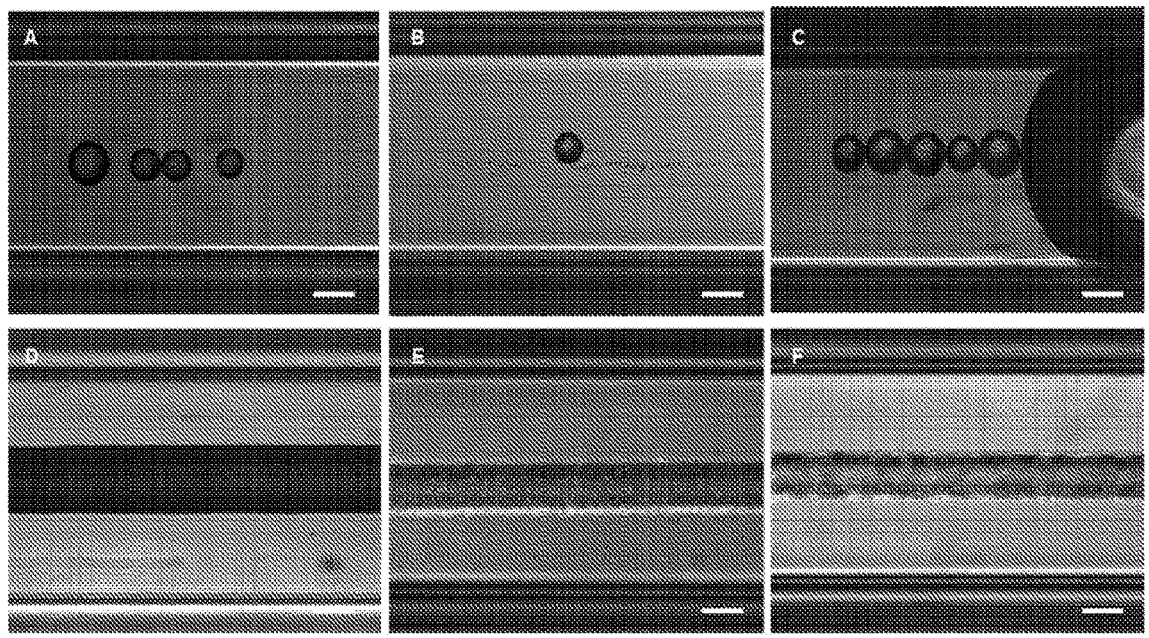
FIG. 27 illustrates another method of multi-cellular 3D assembly based on magnetic signatures.

Example XV: Second Example of Multi-Cellular 3D Assembly Based on Magnetic Signatures FIG. 27 illustrates another method for multi-cellular 3D assembly based on magnetic signatures. Corning Synthemax II polystyrene microcarriers were levitated in 50 mM Gadolinium concentration as depicted in FIG. 27A. FIG. 27B shows an image of co-levitation of polystyrene micro carriers and 3T3 NIH cells after 10 min and FIG. 27C shows the same after 3 days. As depicted in FIG. 27D, 250-300 μm polymeric strand were inserted in levitation device in 100 mM Gadolinium concentration. The image in FIG. 27E shows co-levitation of polymeric strand and GFP-HUVECs cells after 10 min and the image in FIG. 27F shows the same after 1 day in 75 mM Gadolinium concentration. In all of these images, the scale bar is 200 μm.

Figure 28:
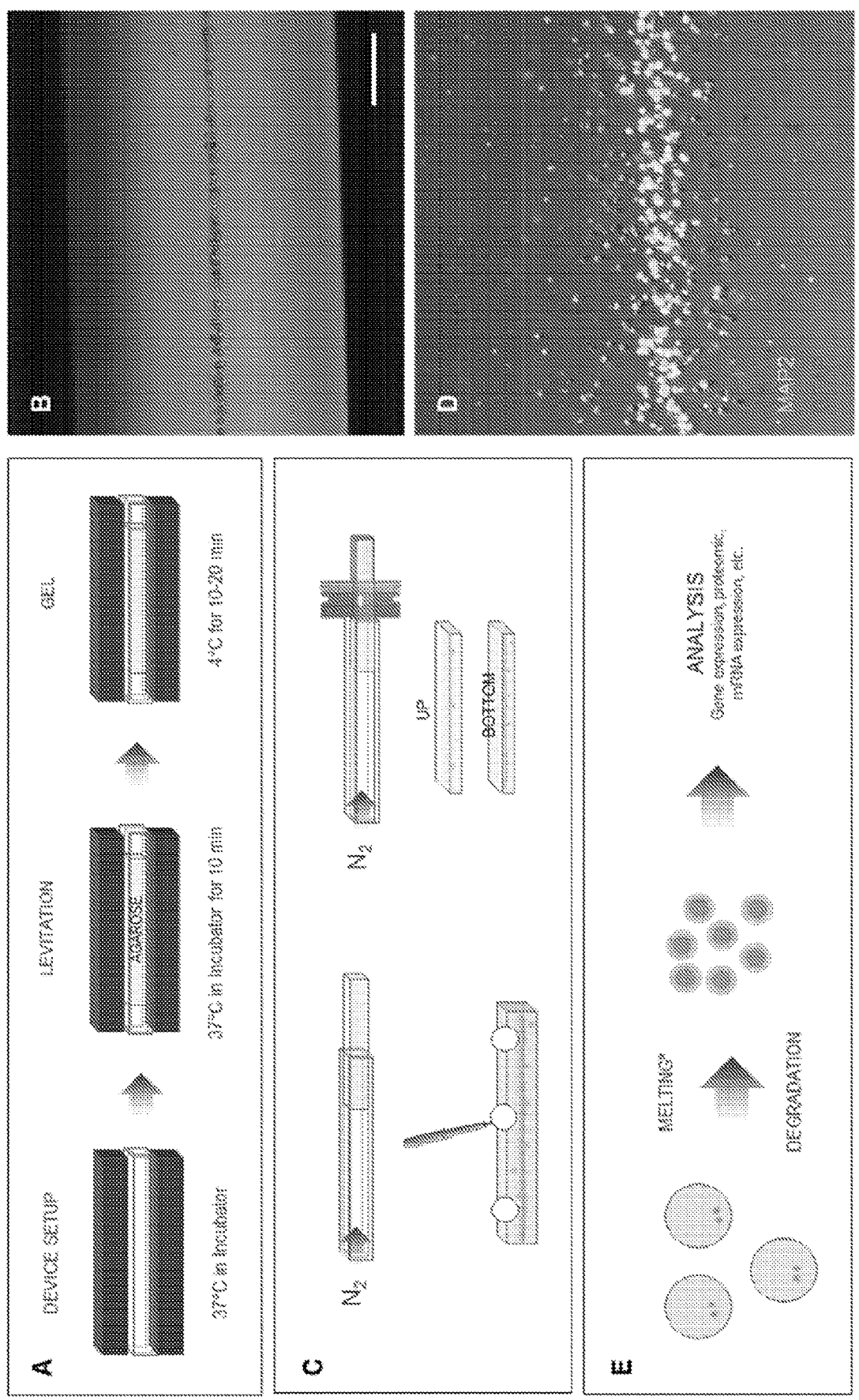
FIG. 28 illustrates a method for cell sorting, recovery and characterization based on magnetic levitation.

Example XVI: Method for Cell Sorting, Recovery and Characterization Based on Magnetic Levitation Referring now to FIG. 28, a method for cell sorting, recovery and characterization based on magnetic levitation is illustrated. Illustration of the method is depicted in FIG. 28A. Cells (e.g., NIH-3T3) levitate in agarose gel and the solidified/cross-liked gel is then removed from the capillary of a gentle flow of nitrogen gas as depicted in FIG. 28B. After removal cells of interest can be isolated by cutting, punching and laser capture microdissection as depicted in FIG. 28C. The gel can be also fixed and immunostained. Results shown the immunostaining of agarose section containing levitated neural cell fraction from mouse cerebellum as depicted in FIG. 28D. Gel sections can be melted or degraded to release to cellular sample to be analyzed as depicted in FIG. 28E.

Example XVII: Spheroid Aggregation Time Study

Figure 29:
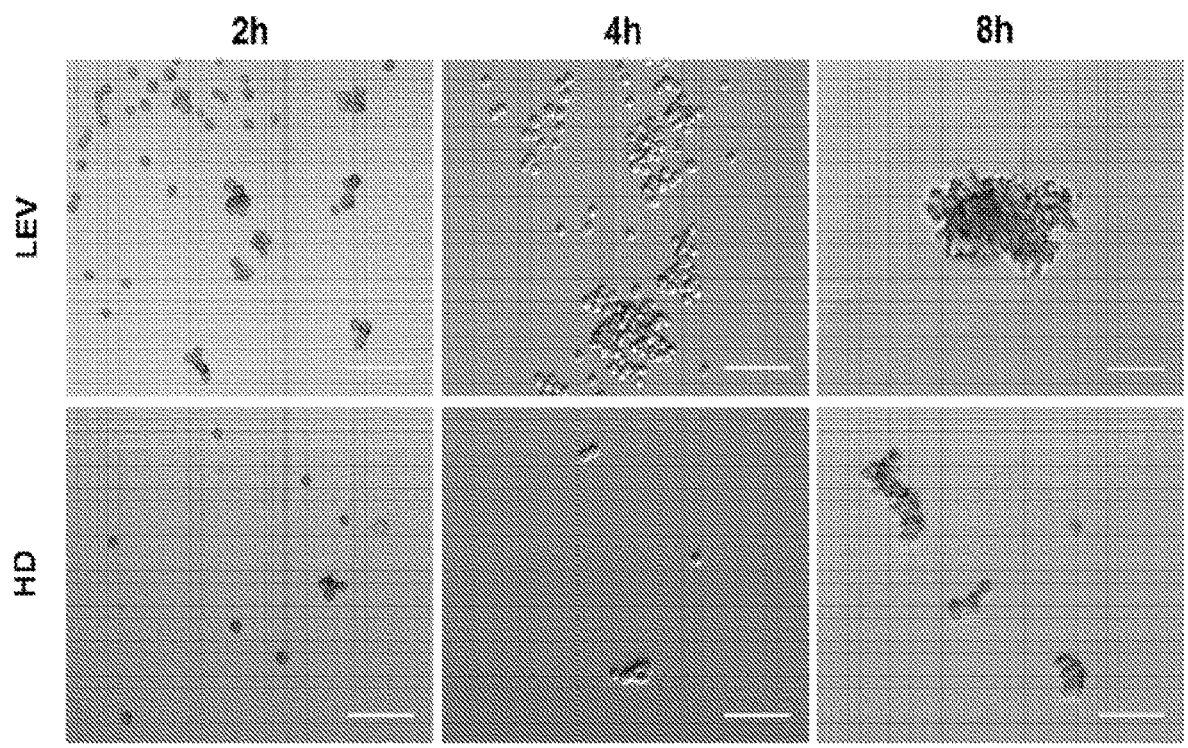
FIG. 29 provides images of an aggregation time study.

With reference being made to FIG. 29, images of an aggregation time study are provided. 3T3 cells were assembled, extracted and imaged at 2, 4 and 8 hours. Magnetic levitation (LEV) and hanging drop (HD) were compared. After 8 hours, stable cell aggregates were formed in the magnetic levitation device. The white scale bar in these images is 200 μm.

Example XVIII: Effects of Gd Concentration and Levitation on Cell Viability

Figure 30:
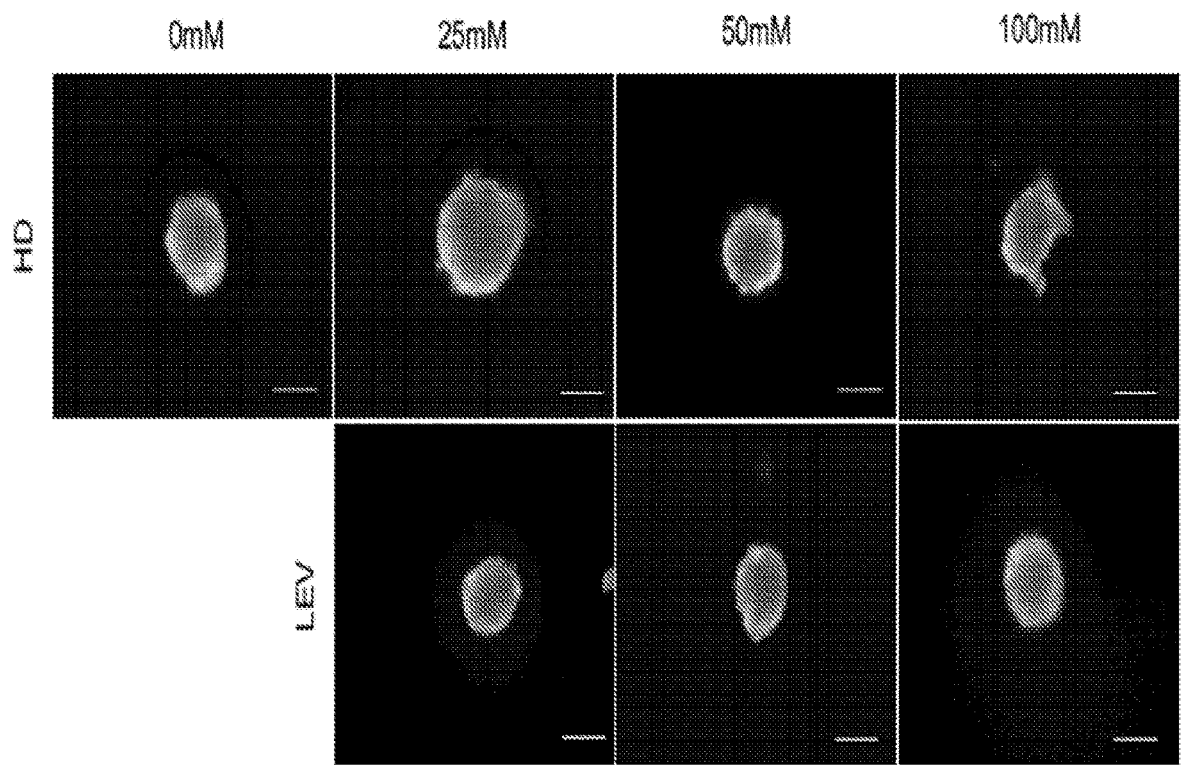
FIG. 30 provides a series of images depicting the effects of gadolinium concentration and levitation on cell viability.

Referring now to FIG. 30, the effects of Gd concentration and levitation on cell viability are illustrated. 3T3 cells were exposed for 48 hours to different concentration of Gd$^+$ (0, 25, 50, 100 mM) during magnetic levitation (LEV) and hanging drop (HD). Spheroid viability was then assessed with live/dead assay (calcein/ethidium homodimer$^{-1}$). The obtained results show that the majority of the cells in the aggregates are alive. The white scale bar is 100 μm.

Example XIX: Merging of Spheroids

Figure 31:
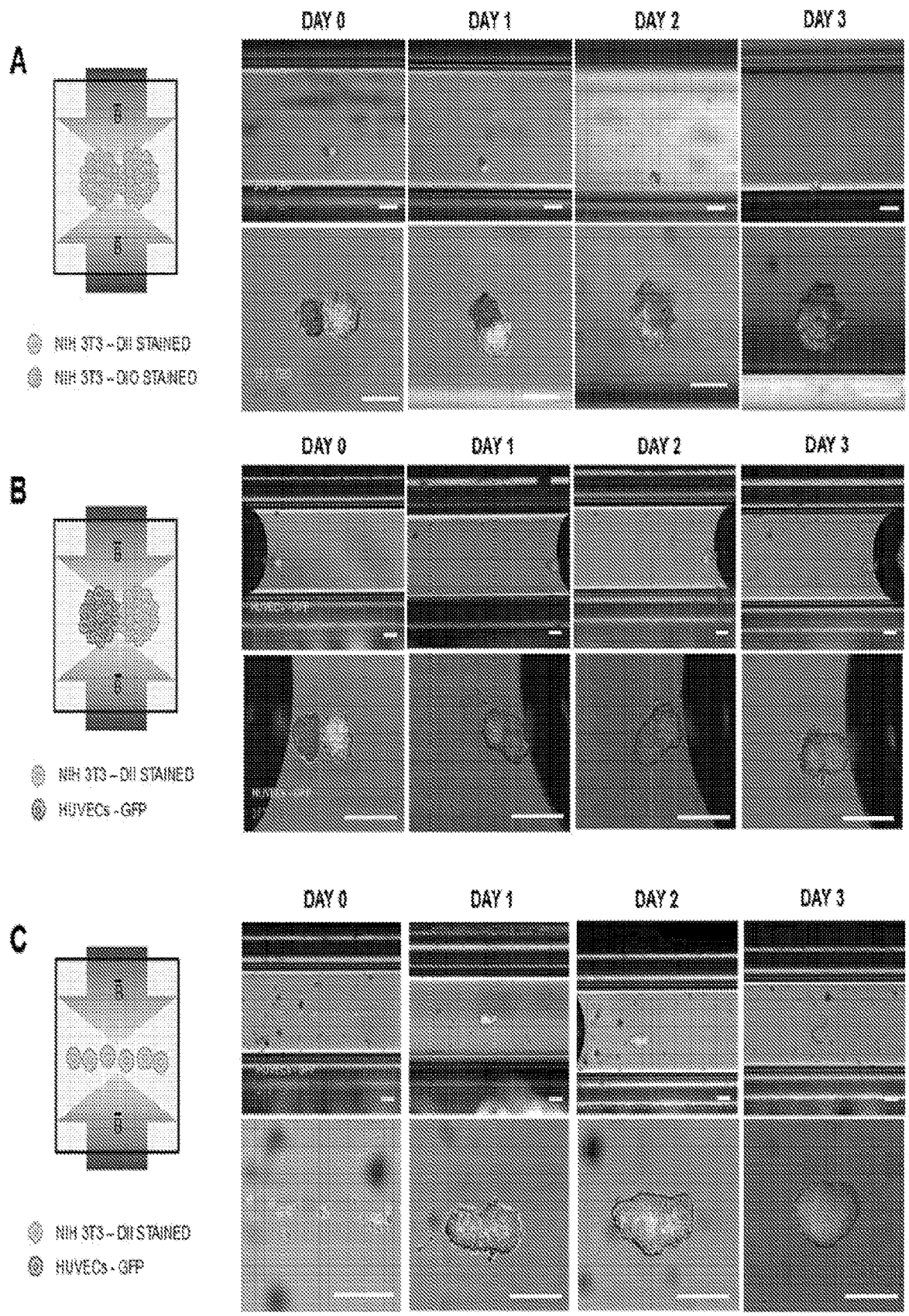
FIG. 31 depicts the merging of various types of spheroids over time.

Referring now to FIG. 31, the merging of DIO-stained (green) and DII-stained 3T3 (red) spheroids is depicted in FIG. 31A, the merging of HUVECs-GFP (green) and DII-stained 3T3 (red) spheroids is depicted in FIG. 31B. Spheroids were previously fabricated by magnetic levitation (48 hours, 50 mM Gd) and then inserted together in one levitation device. Spheroids interaction was monitored for 3 days. In FIG. 31C, HUVECs-GFP (green) and DII-stained 3T3 (red) cells are guided together to form a multicellular spheroid. Bright-field and fluorescence images are presented.

The obtained results show that the levitation system is able to rapidly assembly multicellular spheroids with controlled geometry and cellular organization. The while scale bars are 200 mm.

Example XX: Functionality Study of 3T3 Spheroids

Figure 32:
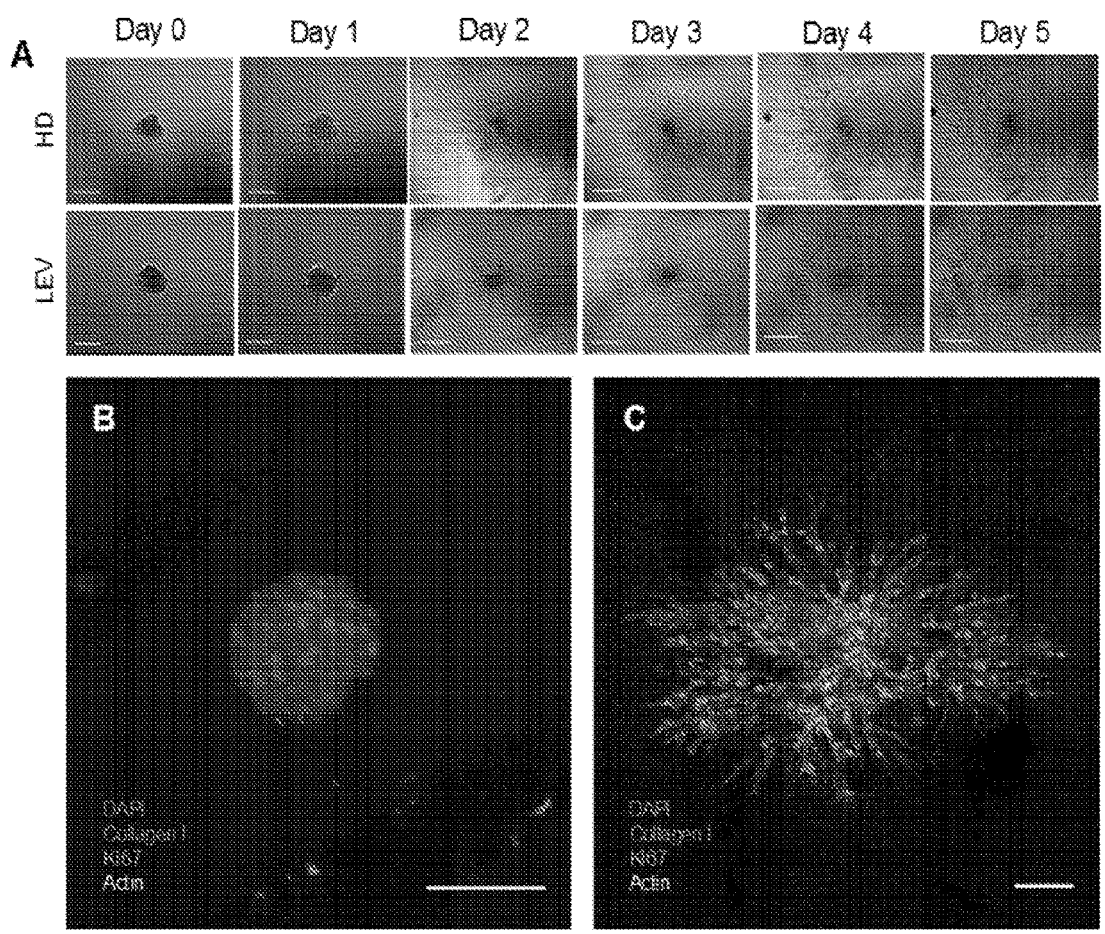
FIG. 32 illustrates the growth study and immunostaining of NIH 3T3 spheroids.

Turning now to FIG. 32, 3T3 spheroids were assembled with magnetic levitation (LEV) and hanging drop (HD) method (48 hours, 50 thousand cells/ml, 50 mM $Gd^+$). The spheroids were then placed in non-adhesive 96-well plate, embedded within fibrin gel (20 mg/ml) and cultured for 5 days as illustrated in FIG. 32A. Every day bright-field images of the spheroids were collected. In FIG. 32A, the scale bar is 200 μm for days 0-2 and 500 μm for days 3-5. FIG. 32B illustrates the spheroids immunostaining after levitation and FIG. 32C illustrates after 5 days in fibrin gel. Nuclei (DAPI, blue), cell proliferation (ki67, magenta), collagen I (red) secretion and actin filaments (green) [colors depicted in greyscale]. The obtained results show that the assembled spheroids are functional. The white scale bar is 200 μm.

Example XXI: Microfluidic Magnetic Levitation System for Assembly

Figure 33:
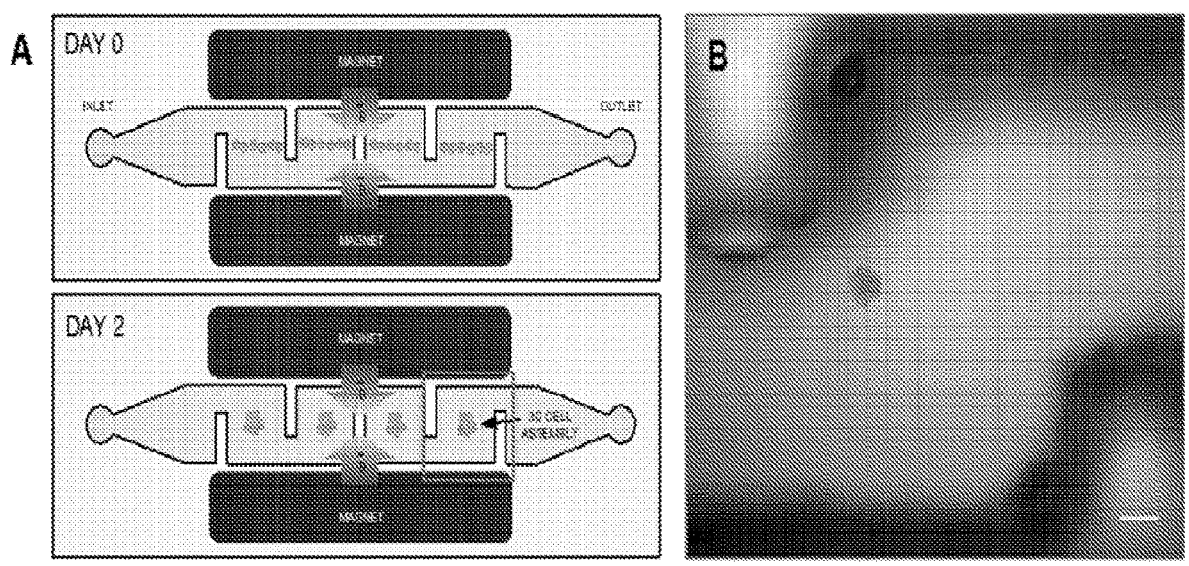
FIG. 33 depicts an exemplary magnetic levitation system for promoting high-throughput assembly of spheroids.

Referring now to FIG. 33A, a schematic of microfluidic magnetic levitation system for assembly of spheroids is provided. In the proposed system, during magnetic levitation, cells are compartmentalized between the microfluidic device walls. Therefore, multiple spheroids (one for each compartment) can be obtained in a high-throughput fashion. FIG. 33B depicts one such spheroid formed at a bend. Cell concentrations of 150 thousand cells/ml were used (48 hours, 60 mM $Gd^+$). In FIG. 33B the scale bar is 200 mm. Assorted Additional Applications of these Magnetic Levitation Systems and Tools It is contemplated that the various tools, methods, and systems described herein may be applied to a wide range of applications. Some of these applications are now provided to indicate some of the various utility of the tools, methods, and systems provided in this disclosure.

Example XXII: Magnetic Bead Strategy for Target Cell (i.e. Bacteria, Yeast, Virus, Pathogen, Circulating Tumor Cells, Circulating Epithelial Cells, Etc.) Identification and Enrichment with Magnetic Levitation Magnetic micro/nanoparticles can be conjugated with species-specific antibodies. Binding of the antibody to the molecular target will change the magnetic signature of the target cell (i.e., a bacteria cell causing an infection). After capture of a specific pathogen type with the magnetic particles, its magnetic signature will increase which will cause the target cell/molecule/pathogen to sink toward to bottom of the microchannels. Captured cells/molecules then can be flushed out and enriched for further analysis, (i.e., antibiotic susceptibility analysis).

Example XXIII: High Throughput Bacterial Cell Isolation and Antibiotic Susceptibility Testing from Clinical Samples Bacterial cells are significantly denser compared to red and white blood cells. After sample injection into the high throughput microfluidic levitation system, bacteria and blood cells will be levitated according to their density signatures and separated into homogenous layers. Due to their higher density, bacterial cells will levitate at a different height and will be collected at another (i.e., bottom) outlet, while red and white blood cells will levitate at a different height and be collected from the other outlets. The high throughput microfluidic platform also enables a unique ability to reuse the isolated pathogens and perform repeated antibiotic susceptibility tests on the same samples. With current clinical assays, bacteria need to be cultured and expanded in number given that the number of isolated bacterial cells is about 10-100 cells/ml. In the microfluidic levitation platform, the bacterial cells will be tested with one antibiotic and investigated for rapid changes in the levitation profiles. If the bacterial population is resistant to the treatment, the bacterial cells will be flowed out of the channels, the chambers will be washed with PBS to get rid of the remaining antibiotic solution and the same bacterial population will be tested with another antibiotic candidate. Thus, this capability will significantly eliminate the need to culture the pathogens that are very low in number for future antibiotic susceptibility testing.

Figure 34:
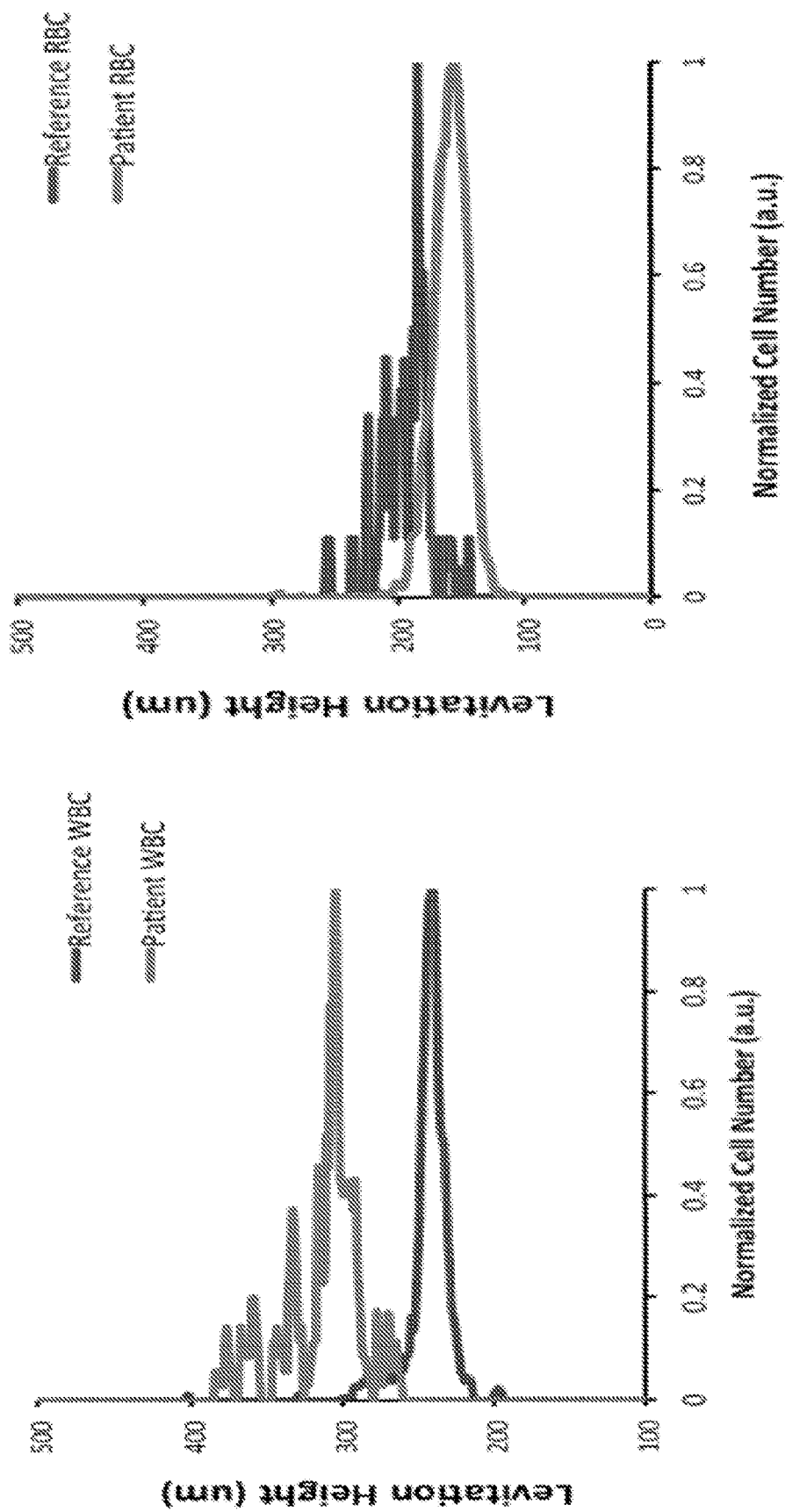
FIG. 34 depicts the use of the levitation platform applied to the profile of a pair of patient blood samples to identify the presence of chronic disease.

Example XXIV: Levitation Platform Applied to Profile the Blood Cells of Patients Suffering from Chronic Diseases With reference to FIG. 34, the levitation platform can be applied to profile the blood cells of patients suffering from chronic diseases. For instance, levitation profile of blood cells (i.e., red blood cells (RBC) and white blood cells (WBC)) from a severely ill chronic fatigue syndrome (CFS) patient is significantly different than the profile of WBC from healthy controls.

Figure 35:
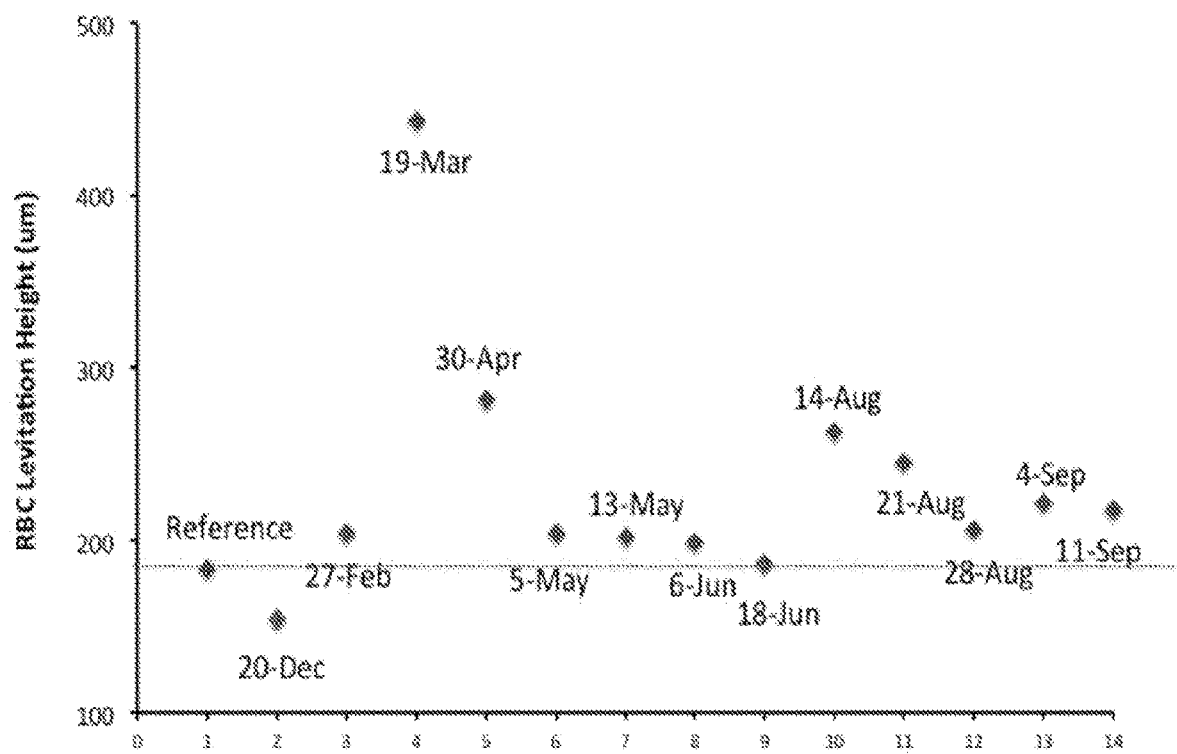
FIG. 35 illustrates the continuous monitoring of RBCs over time in a patient having chronic fatigue syndrome.
Figure 36:
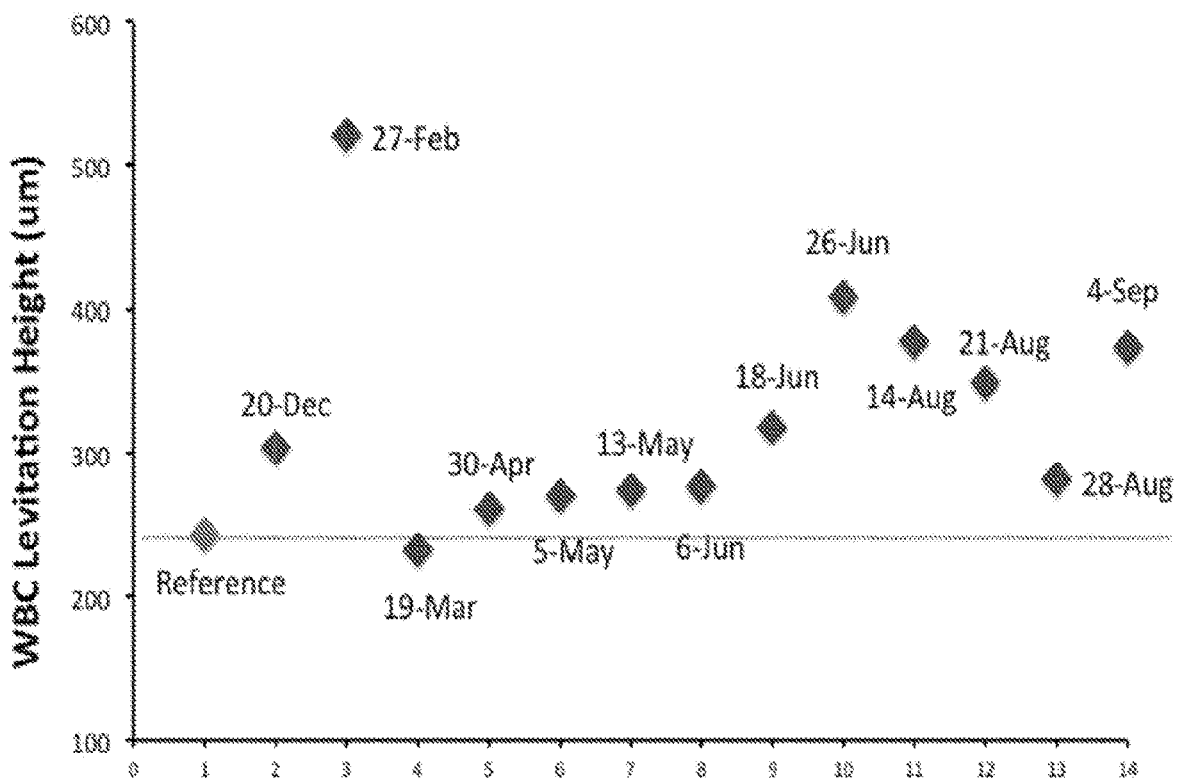
FIG. 36 illustrates the continuous monitoring of WBCs over time in a patient having chronic fatigue syndrome.

Example XXV: Continuous Monitoring and Levitation Profiling of Red Blood Cells from Patients Suffering from Chronic Diseases FIGS. 35 and 36 depict continuous monitoring and levitation profiling of red blood cells and white blood cells, respectively, from patients suffering from chronic diseases (i.e., chronic fatigue syndrome). Such continuous monitoring may help to identify root causes or changes in blood profile over time.

Figure 37:
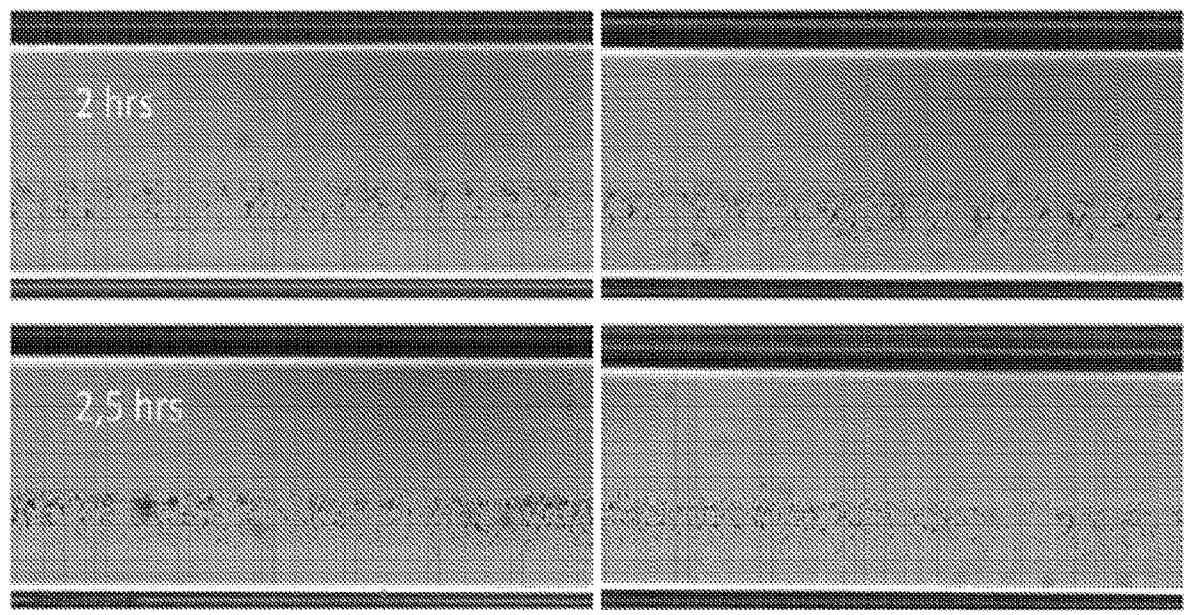
FIG. 37 shows the screening and monitoring the effect of metabolites, chemicals using levitation device.
Figure 37:
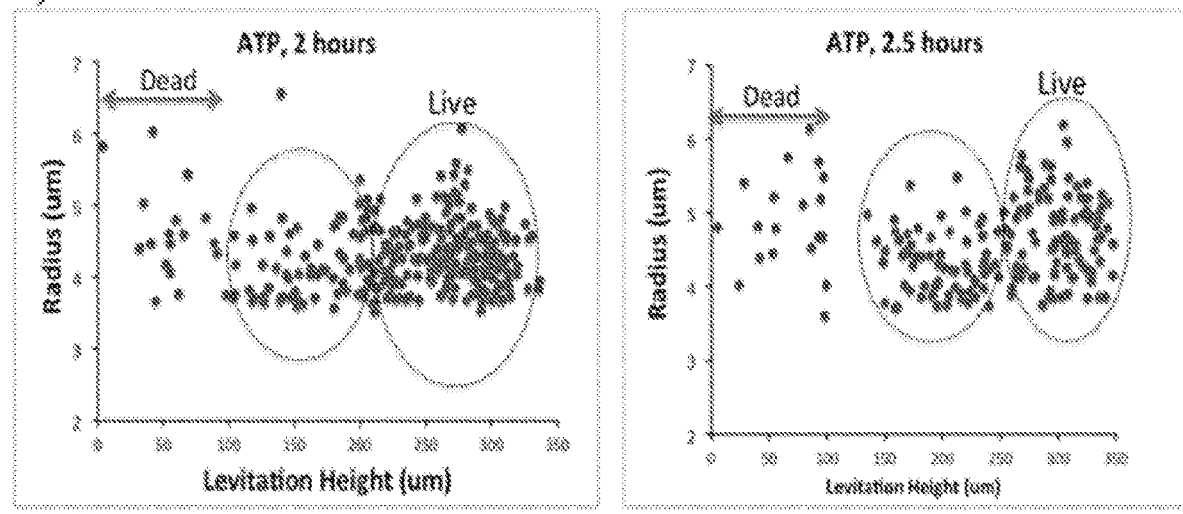

Example XXVI: Screening and Monitoring the Effect of Metabolites, Chemicals Using Levitation Device FIG. 37 shows the screening and monitoring the effect of metabolites, chemicals using levitation device. FIG. 37A shows a levitation system being used to study the effect of ATP addition to the white bloods cells that are isolated from a patient suffering from a chronic disease (i.e., chronic fatigue syndrome, cancer, infectious diseases). FIG. 37B illustrates cell viability, number of live and dead white blood cells can be monitored, detected and counted according to their levitation profiles in real-time with single-cell resolution.

Example XXVII: Antimicrobial Applications

Additionally, this magnetic levitation system can be applied to many antimicrobial applications such as, but not limited to: the detection of bacterial cells from soil, portable and rapid detection of bacterial cells from surfaces (i.e., swap samples), the surveillance of microbes on medical device surfaces or in hospital management systems, and the detection and separation of spores from vegetative bacterial cells.

Example XXVIII: Levitation of Bacterial Cells

Figure 38:
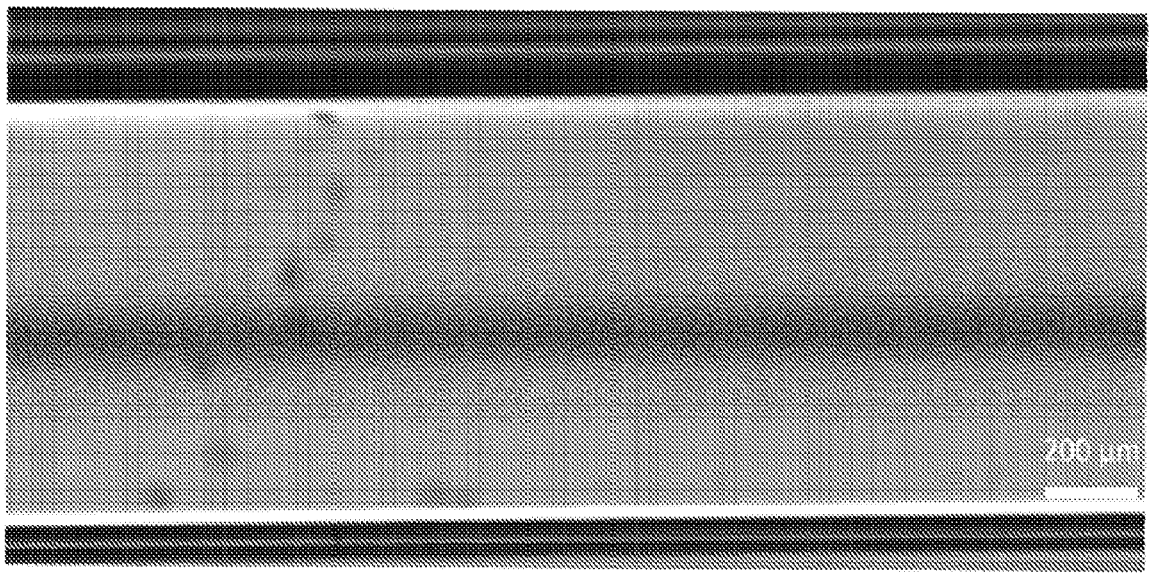
FIG. 38 depicts the magnetic levitation of bacterial cells.

With reference being made to FIG. 38, bacteria cells can be levitated and detected in different biological mediums and soil (i.e., fetal bovine serum). Overnight cultures of *E. coli* (Dh5α) was diluted in FBS and levitated in 100 mM Gd$^+$ solution. Bacteria cells formed their intrinsic levitation bands after one hour of levitation.

Example XXIX: Rapid Detection of Bacterial Cells from Surfaces

Figure 39:
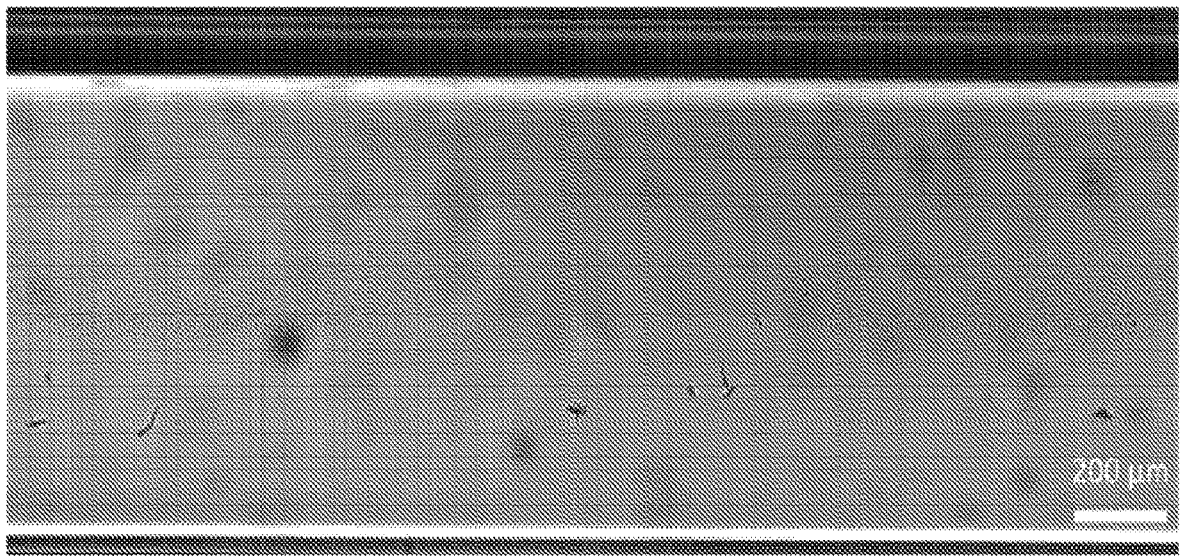
FIG. 39 provides images of bacterial cell bands obtained using magnetic levitation on samples swabbed from a surface to be tested.
Figure 39:
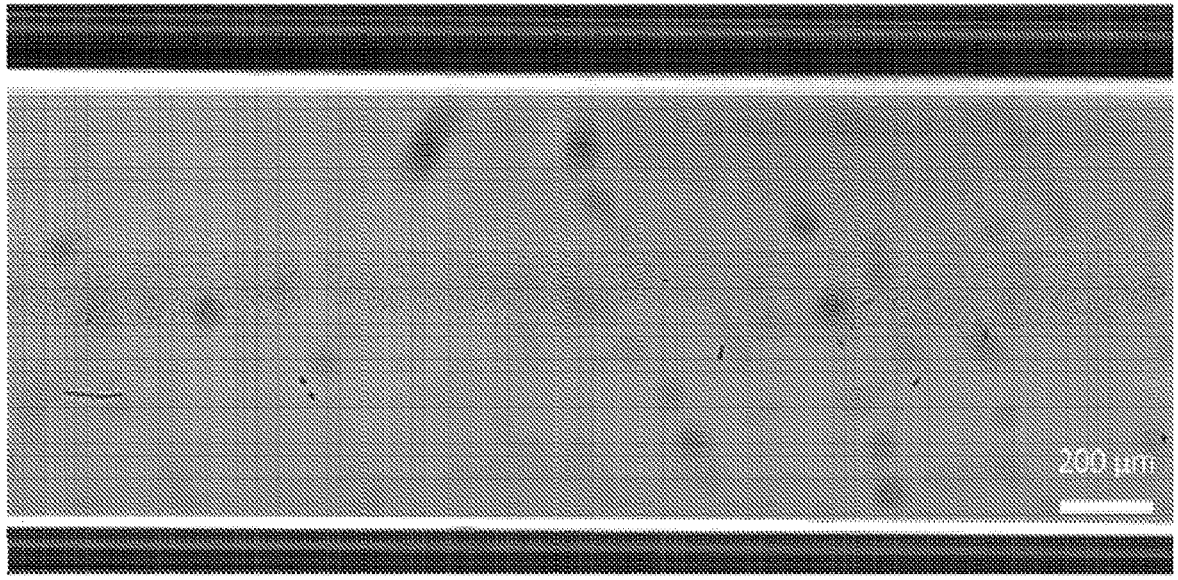
Figure 40:
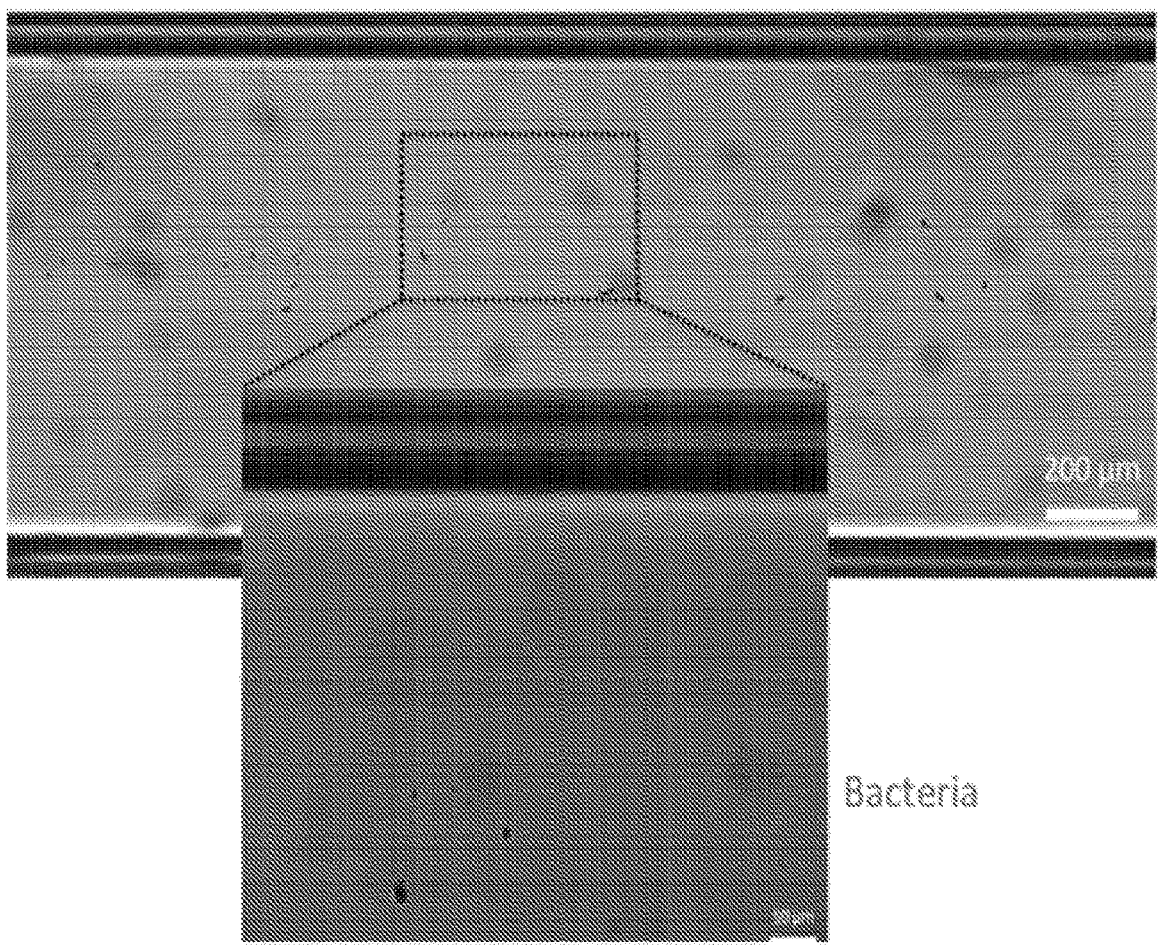
FIG. 40 illustrates that bacteria cells can be rapidly detected from surfaces within 5 minutes under high paramagnetic conditions.
Figure 40:
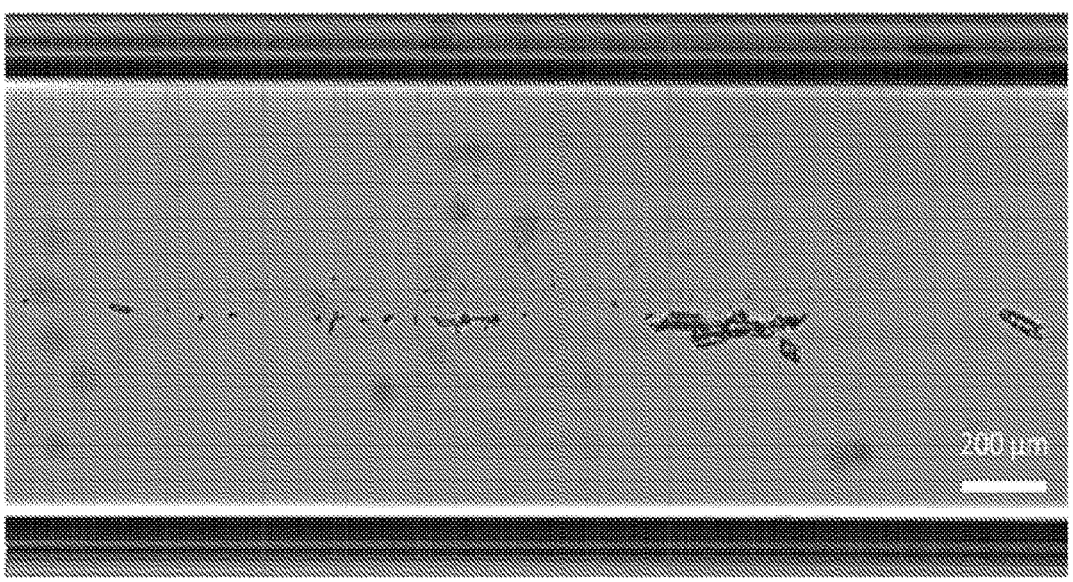

FIGS. 39 and 40 demonstrate that bacteria cells can be rapidly detected from surfaces. 100 ul of liquid *E. coli* (Dh5α) culture was poured onto the glass slides and then the surface was cleaned with a cotton swap. Then, the cotton swaps were vortexed in PBS and 30 ul swap sample was levitated in 200 mM Gd+ solution. Bacteria cells formed their intrinsic levitation bands within 30 minutes. Thus, bacteria can be rapidly detected from surfaces with the portable levitation system.

Turning now to FIG. 40, it is shown that bacteria cells can be rapidly detected from surfaces within 5 minutes under high paramagnetic conditions. 100 ul of liquid *E. coli* (Dh5α) culture was poured onto the glass slides and then the surface was cleaned with a cotton swap. Then, the cotton swaps were vortexed in PBS and 30 ul swap sample was levitated in 900 mM Gd+ solution. Bacteria cells formed their intrinsic levitation bands within 5 minutes. Thus, bacteria can be rapidly detected from surfaces with the portable levitation system.

Example XXX: Levitation of Other Types of Moieties and Cells

Figure 41:
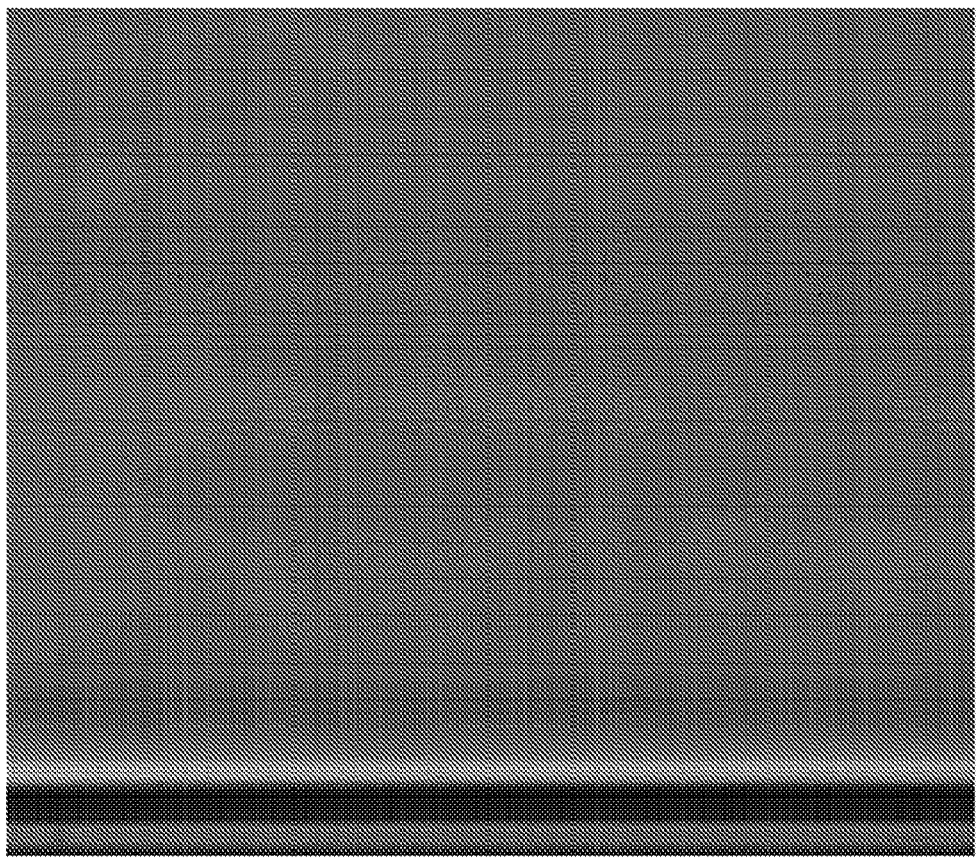
FIG. 41 illustrates the levitation and detection of spores in the magnetic levitation system.
Figure 42:
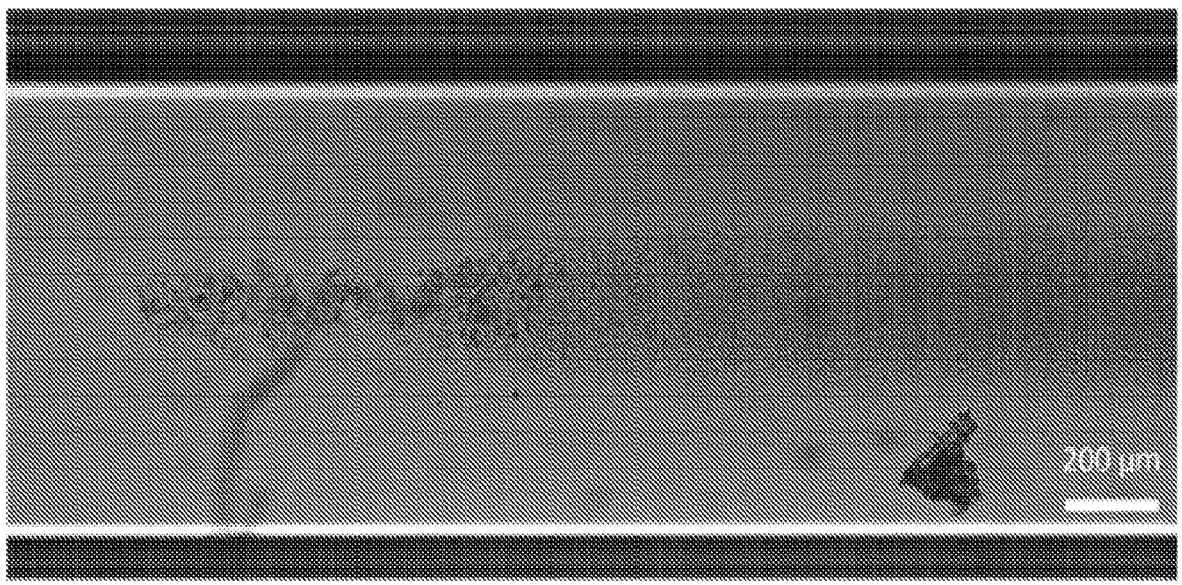
FIG. 42 illustrates that vegetative bacterial cells can be levitated and detected within the levitation system.

Other types of cells can be levitated within the disclosed systems under proper levitation configuration conditions. As some further examples, FIG. 41 illustrates the levitation and detection of spores in the magnetic levitation system (see the lightly dotted band). Likewise, FIG. 42 illustrates that vegetative bacterial cells can be levitated and detected within the levitation system.

Example XXXI: Prediction of Oocyte Quality Using Magnetic Levitation

The quality of oocytes can be predicted according to their levitation and density profiles for applications in reproductive studies such as in-vitro fertilization (IVF).

Figure 43:
FIG. 43 illustrates the levitation profiles of oocytes.

Referring now to FIG. 43, the levitation profiles of various oocytes are illustrated. Oocytes isolated from mice were levitated at different paramagnetic solutions (10 mM, 15 mM and 30 mM Gd+). Density of oocytes at different stages can be monitored and calculated from their levitation profile.

Example XXXII: Levitation Profiles of Uninfected Vs. HIV-Infected CD4 T Cells

Figure 44:
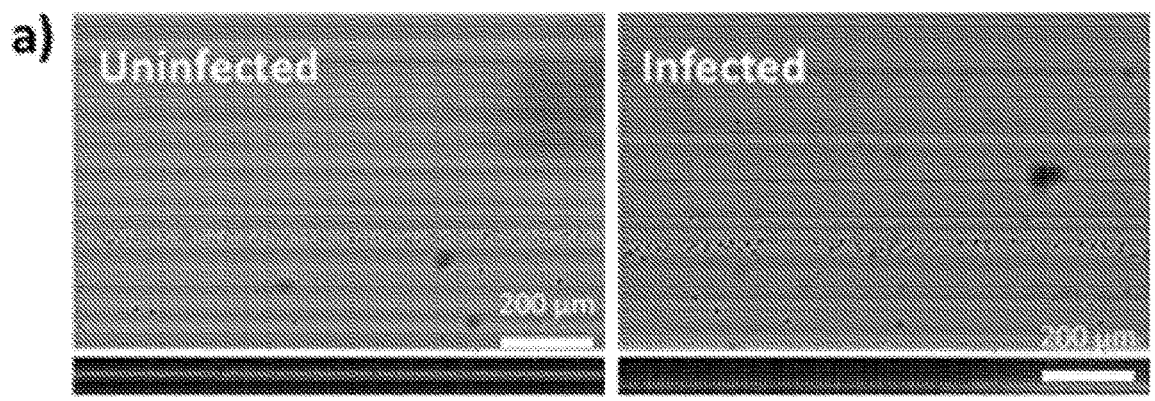
FIG. 44 demonstrates that uninfected and HIV-infected blood CD4 T cells have significantly different levitation profiles in the magnetic levitation-based platform.
Figure 44:
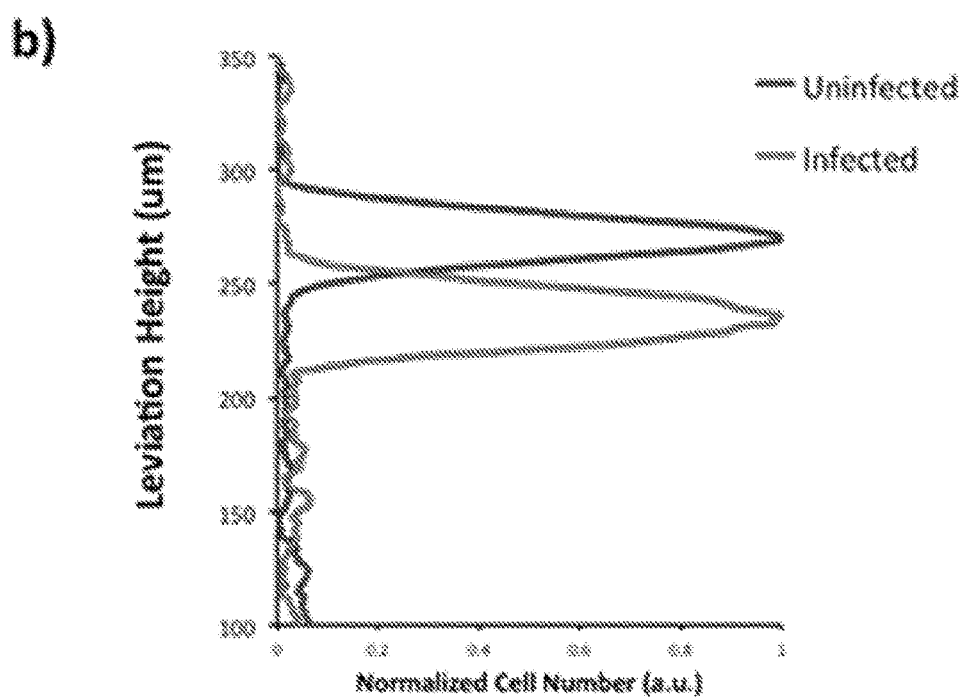

The magnetic levitation device was also used to study the levitation Profiles of uninfected vs. HIV-infected CD4 T cells. 100,000 uninfected and HIV-infected blood CD4 T cells were levitated in phosphate buffered saline solution (PBS) with 30 mM paramagnetic solution, respectively. The samples were levitated for 20 minutes and the levitation profiles were compared. As illustrated in FIGS. 44A and 44B, uninfected and HIV-infected blood CD4 T cells have significantly different levitation profiles in the magnetic levitation-based platform.

Figure 45:
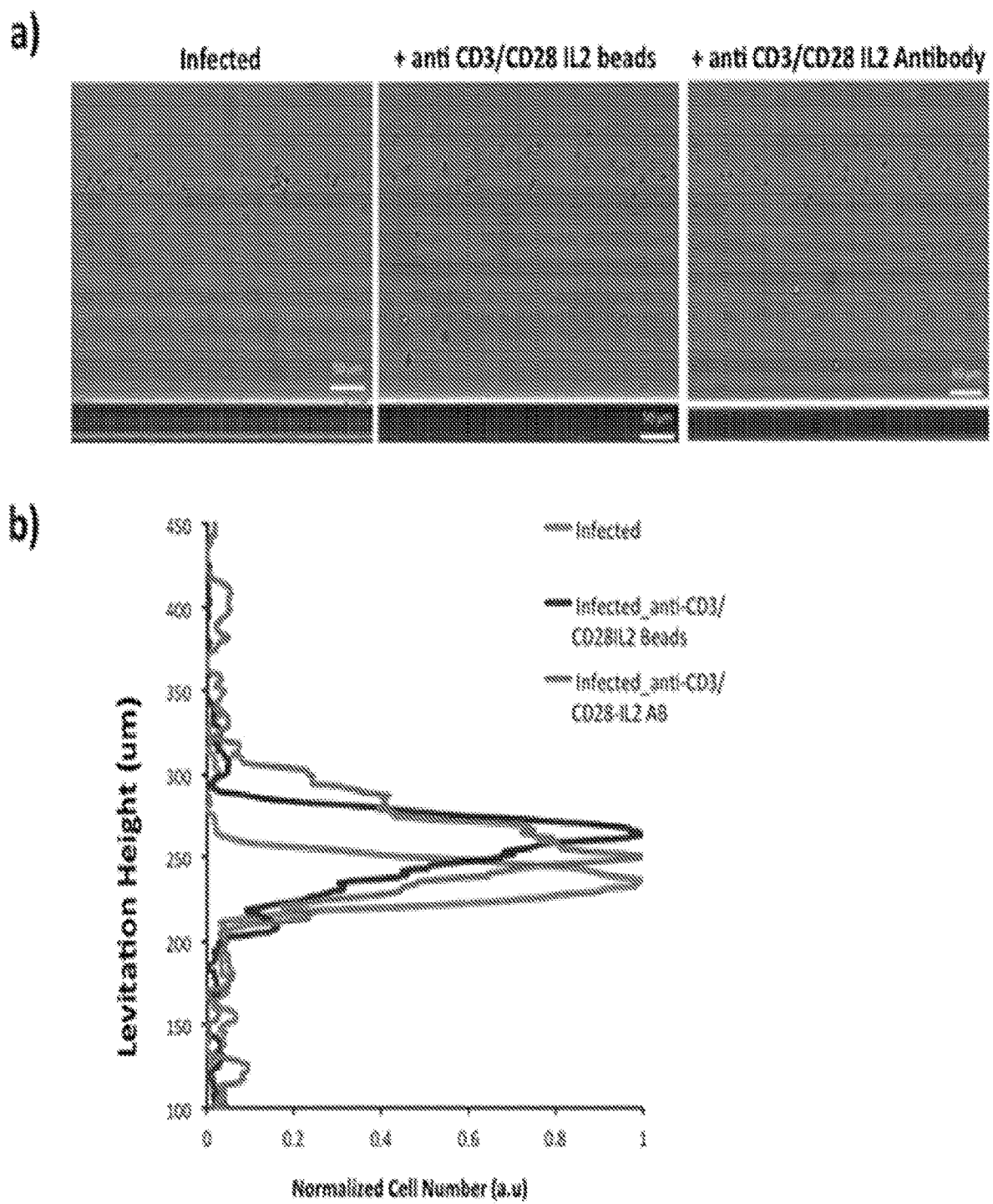
FIG. 45 shows stimulation with anti-CD3/CD28/IL2 beads and anti-CD3/CD28/IL2 antibody change the levitation profiles of HIV-infected blood CD4 T cells.

For comparative purposes, the effect of stimulation on infected cells is illustrated in FIG. 45. 100,000 HIV-infected CD4 T cells stimulated with anti-CD3/CD28/IL2 beads and anti-CD3/CD28/IL2 antibody were levitated in PBS solution with 30 mM paramagnetic solution, respectively, as shown in FIG. 45A (and quantified in FIG. 45B). HIV-infected blood CD4 T cells were used as controls. The samples were levitated for 20 minutes and the levitation profiles were compared. It was shown that stimulation with anti-CD3/CD28/IL2 beads and anti-CD3/CD28/IL2 antibody changes the levitation profiles of HIV-infected blood CD4 T cells.

Example XXXIII: Additional Design for Microfluidic High-Throughput Magnetic Levitation Platform (i.e., the Addition of Needles and Suction)

Figure 46:
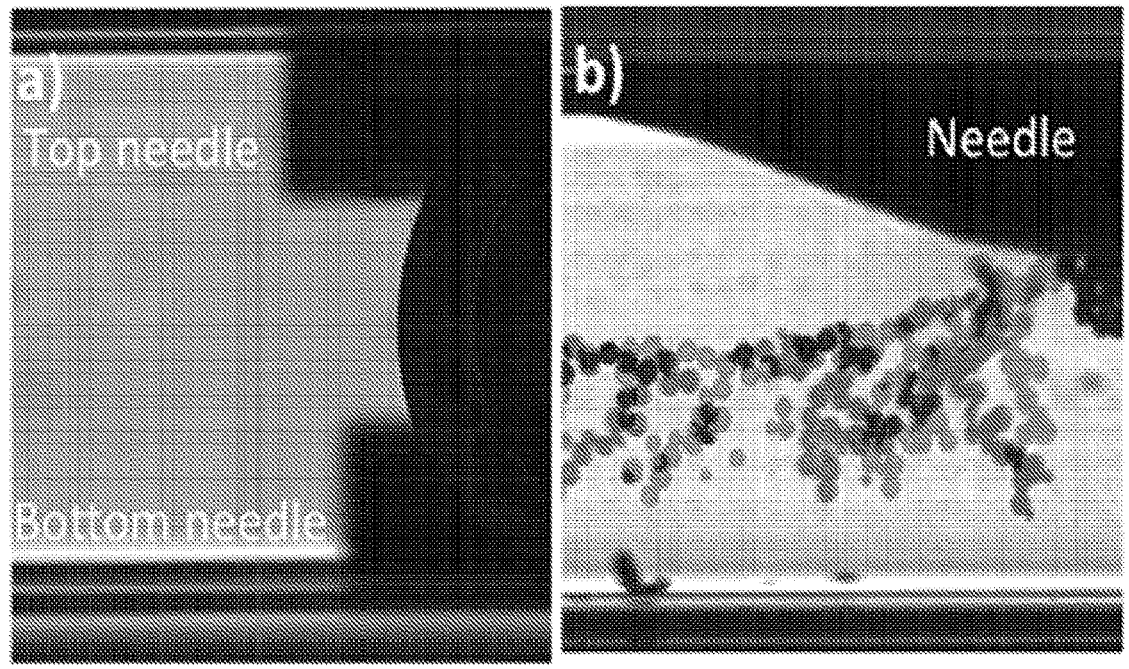
FIG. 46 shows the design for a microfluidic, high-throughput magnetic levitation device including needles at the end of a channel.
Figure 46:
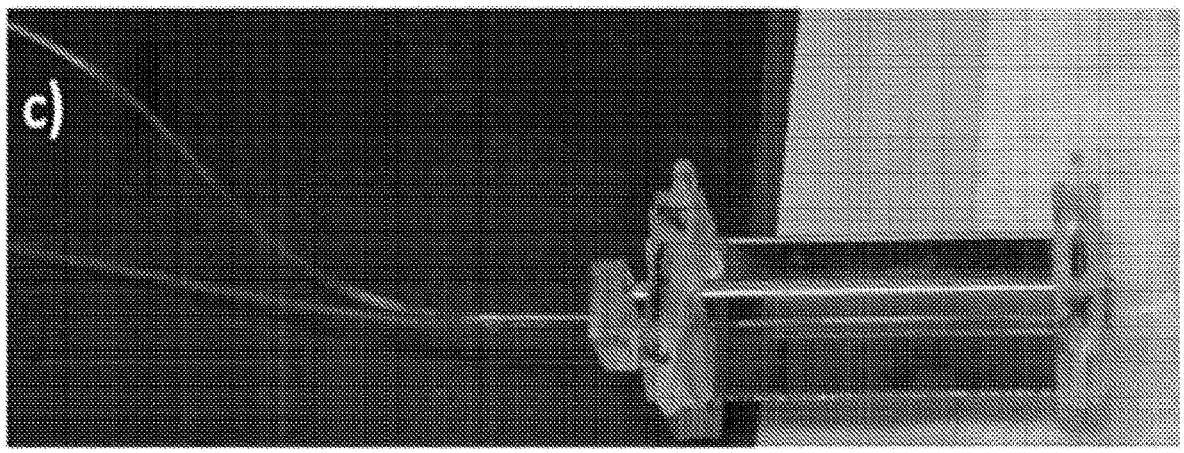

Turning now to FIG. 46, an image of a microfluidic levitation platform (µMagLev) is illustrated that includes of a microcapillary channel, inlets, two or more needles at the end of the microcapillary channel: a) one or more needles at the top of the channel, b) one or more needles at the bottom of the channel, as well as collection outlets. In addition, these needles can be located anywhere in the 3D spatial domain of the channel or outside. Samples (i.e., beads, cancer cells, blood, etc.) can be mixed in the inlet and then a variety of negative pressure and flow rates can be used to withdraw the samples according to their densities. Samples with lower density or lower magnetic susceptibility can be withdrawn by a microfluidic pump with the bottom needle and collected in the bottom outlet tube. Samples with higher density or higher magnetic susceptibility can be withdrawn with the bottom needle and collected in the bottom outlet tube. Other design parameters of the magnetic platform (e.g., magnet strength, geometric positioning of magnets, dimensions) can further be modified accordingly to enable rapid processing and better sorting.

In FIG. 46A, two needles are at the end of the microcapillary channel. Then in FIG. 46B, it is shown that beads and cells can be simultaneously flowed, sorted, withdrawn and collected by negative pressure during flow. In FIG. 46C, a photo of a prototype for the microfluidic maglev system is shown.

Figure 47:
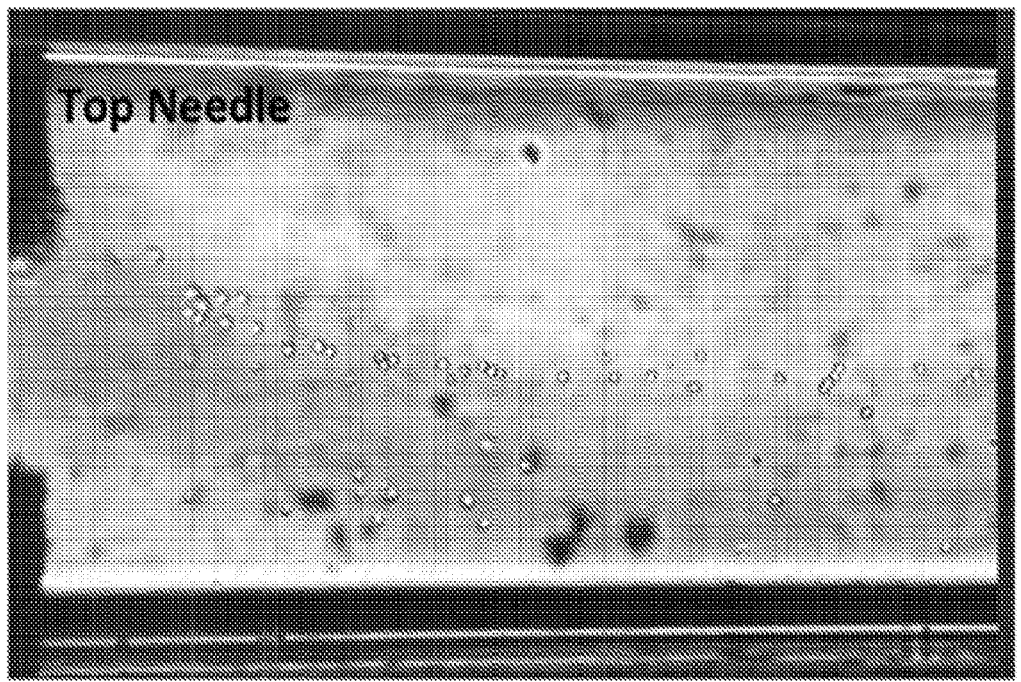
FIG. 47 shows cell manipulation and collection within the microfluidic magnetic levitation system.
Figure 47:
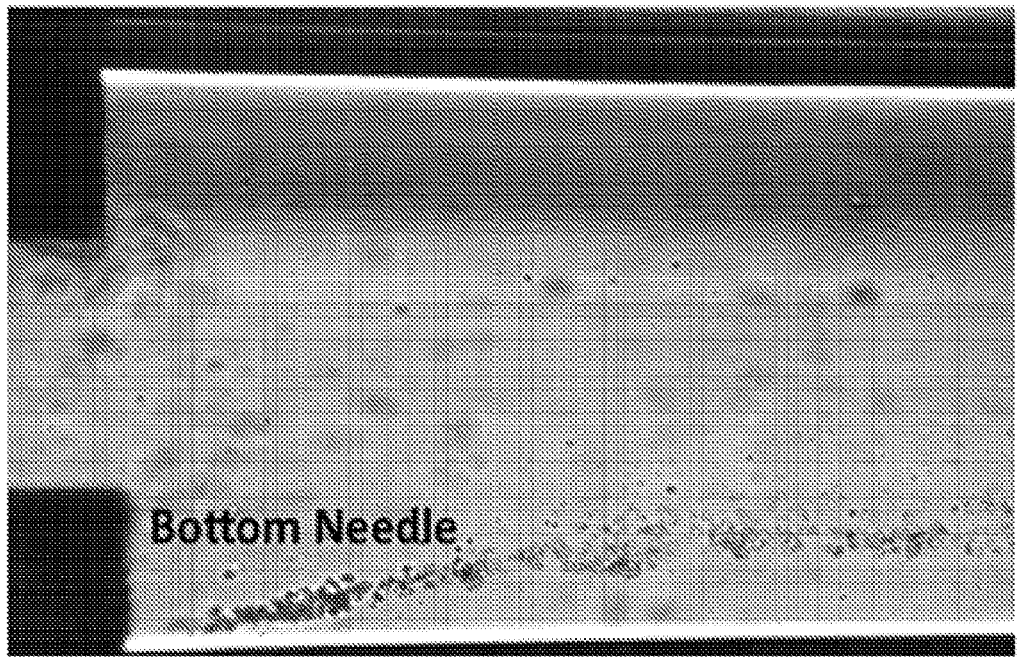

Turning now to FIG. 47, cell manipulation and collection within the microfluidic magnetic levitation system is illustrated. In FIG. 47A, samples with lower density or lower magnetic susceptibility can be withdrawn by a microfluidic pump with the top needle and collected in the top outlet tube. In addition, samples can be withdrawn to the top collection needle by keeping the suction of the top needle higher than the suction at the bottom needle (suction$_{top\ needle}$>suction$_{bottom\ needle}$). Flow rates at multiple suction ports can be relatively manipulated to determine where the levitated samples will be collected from. In FIG. 47B, higher density samples can be withdrawn with the bottom needle and collected in the outlet tube connected to the bottom collection needle. In addition, samples can be withdrawn to the bottom collection needle by keeping the suction of the top needle lower than the suction at the bottom needle (suction$_{top\ needle}$<suction$_{bottom\ needle}$).

Example XXXIV: Results for Droplet Sorting and Droplet Sequencing

Droplets can be levitated within the magnetic levitation system providing various different methods for analysis and diagnostics. Droplets can be suspended in different solutions and detergents (i.e., fetal bovine serum, plasma, fetal-bovine serum with PBS-Tween, plasma with PBS-Tween) with paramagnetic solution. Droplets encapsulating biological moieties (i.e., cells, RNA, DNA, virus, bacteria, etc.) can be sorted and separated. Droplets encapsulating different types of cells can have different levitation profiles and then sorted and collected for further characterization for genomic, transcriptomic, proteomic, and metabolic analysis. Droplets containing live and dead cells can have different levitation profiles. This can be used for Drop-Seq applications to separate droplets containing dead cells vs. live cells. Droplets encapsulating only the live cells then can be used for Drop-Seq. This capability will significantly reduce the cost and processing time for Droplet-Sequencing methods.

Figure 48:
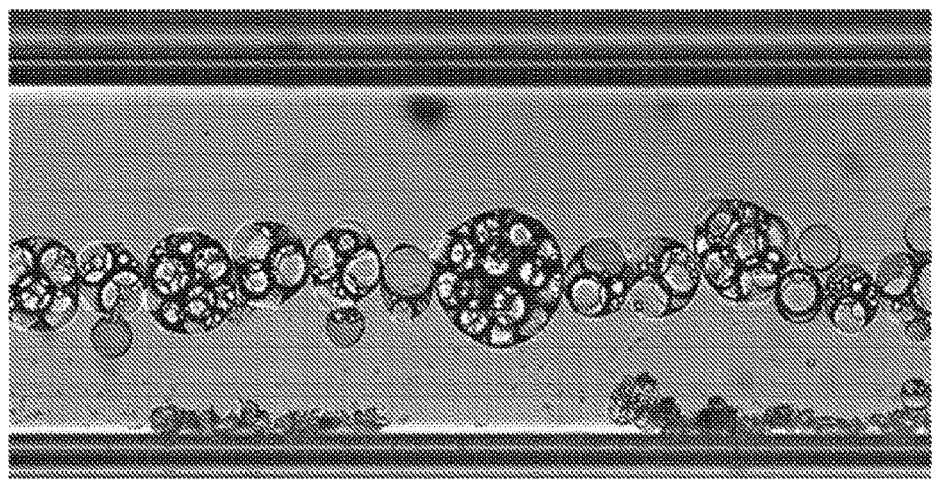
FIG. 48 illustrates the levitation of droplets in fetal bovine serum (FBS) with 150 mM paramagnetic solution (i.e., gadolinium).
Figure 49:
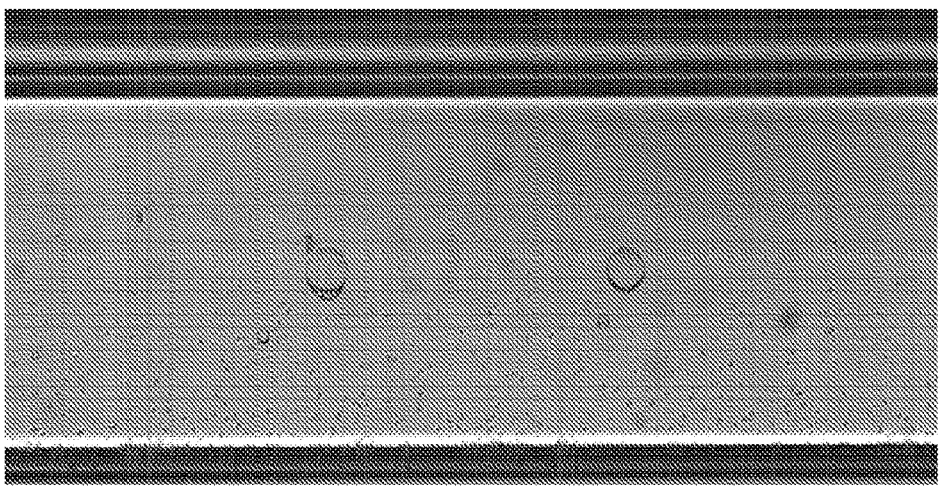
FIG. 49 illustrates the levitation of droplets in fetal bovine serum (FBS)+PBS-Tween 20 with 150 mM paramagnetic solution (i,e, gadolinium).
Figure 50:
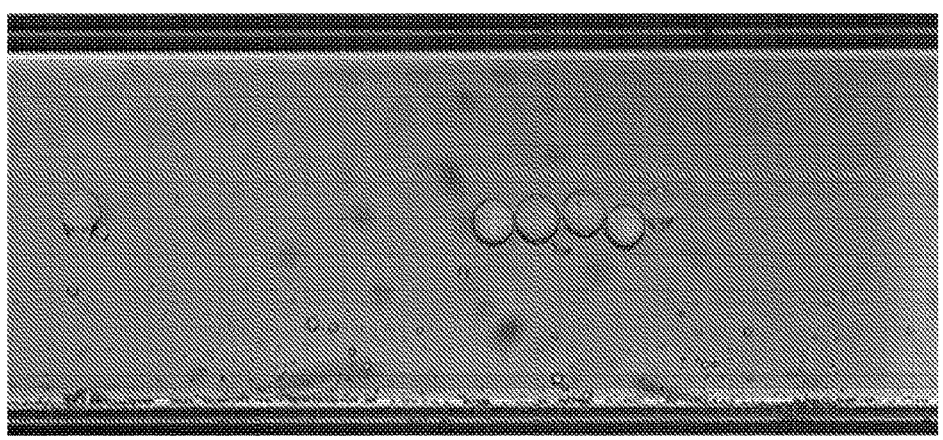
FIG. 50 illustrates the levitation of droplets in fetal bovine serum (FBS)+PBS-Tween 20 with 150 mM paramagnetic solution (i,e, gadolinium) in which the droplet encapsulate different biological moieties.

Looking first at FIG. 48, droplets are levitated in fetal bovine serum (FBS) with 150 mM paramagnetic solution (i,e, gadolinium). In FIG. 49, droplets are levitated in fetal bovine serum (FBS)+PBS-Tween 20 with 150 mM paramagnetic solution (i,e, gadolinium). PBS-Tween solution helps to disperse the droplets. In FIG. 50, droplets are levitated in fetal bovine serum (FBS)+PBS-Tween 20 with 150 mM paramagnetic solution (i,e, gadolinium). Droplets encapsulating different biological moieties can be levitated, sorted and separated. Empty droplets vs droplets containing a fluorescently labeled viral particle can be levitated and imaged. Fluorescent vs non-fluorescent droplets can be sorted within the levitation system.

Example XXXV: Collection of Data for Cancer Studies

Figure 51:
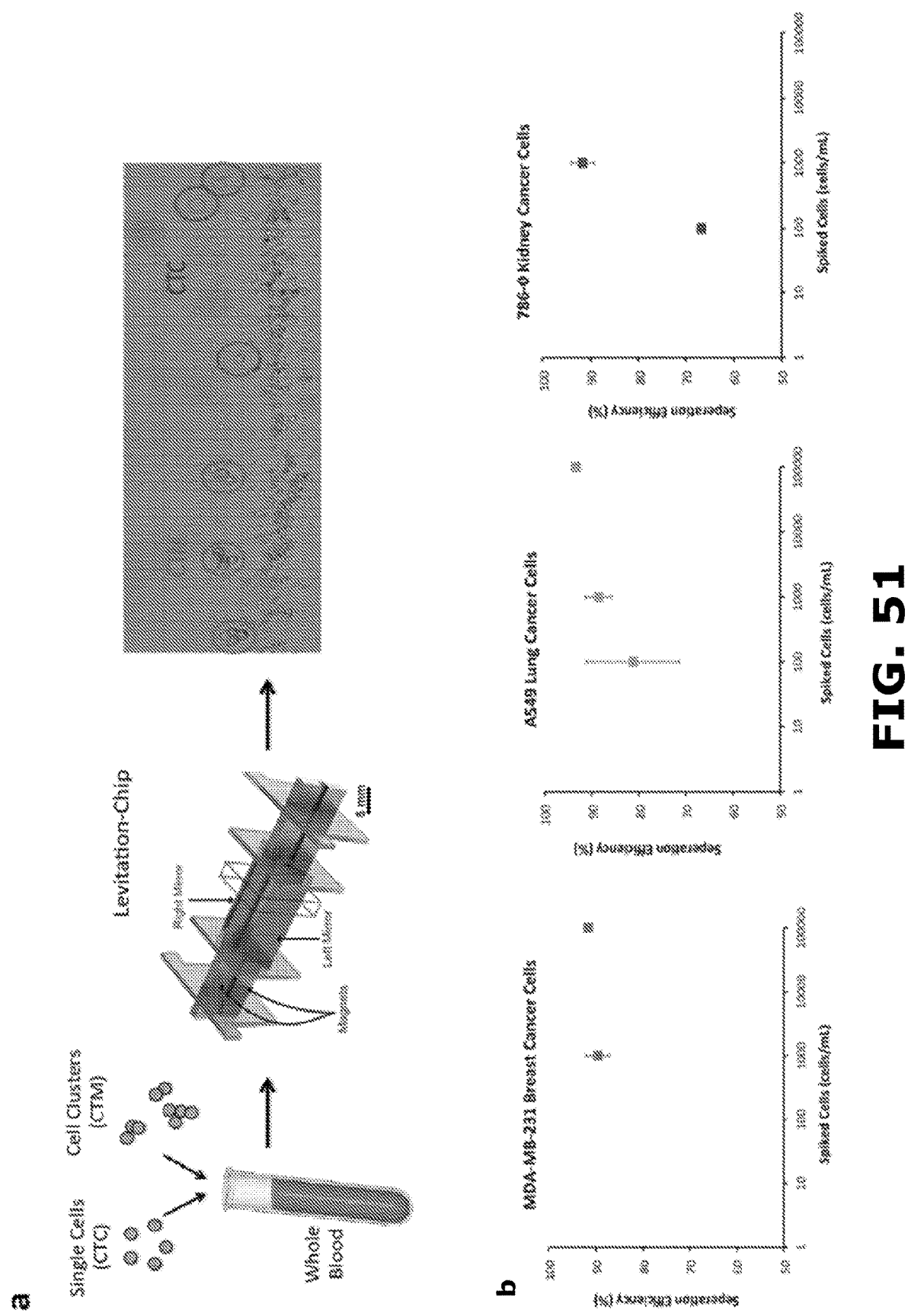
FIG. 51 illustrates the characterization of the chemistry- and label-free magnetic levitation chip in cancer studies.

FIG. 51 characterizes a chemistry- and label-free magnetic levitation chip. The levitation chip can separate circulating tumor cells and circulating tumor clusters within the same device at the same time. As illustrated in FIG. 51A, a procedure is depicted that can be used to test for the presence of calcein-labeled single cells (CTC) and aggregates of cancer cells (CTM). Single cells of kidney cancer cells (CTC) and clusters (CTM) of kidney cancer cells can be separated and sorted at the same time, within the same device be detected without using any labels, in spike-in experiments with WBCs. Then, in FIG. 51B, the separation efficiency of cancer cells from blood via magnetic blueprinting is shown. Efficiency at different concentrations of spiked cancer cells (100 cells/mL, 1,000 cells/mL, 100,000 cells/mL) were analyzed and compared for different cancer cell types (i.e., lung, breast and kidney cancer). Separation efficiency is defined as the ratio of cancer cells levitated above the blood cell band to the total number of spiked cancer cells. (N=3 independent experiments, data are represented as the mean±standard error of the mean (SEM)).

Blood sample from kidney cancer patients was diluted at a 1:20 ratio in FBS and then levitated in 30 mM Gd+ solution in the magnetic levitation device. After 20 minutes of levitation, CTCs and clusters of CTCs (blue circles, i.e., the three circles on the right) were levitated above the band consisting of RBCs and WBCs depicted in FIG. 51A, rightmost image. These putative CTCs were observed to be very light in density, as they have levitated at the top of the microcapillary channels.

Figure 52:
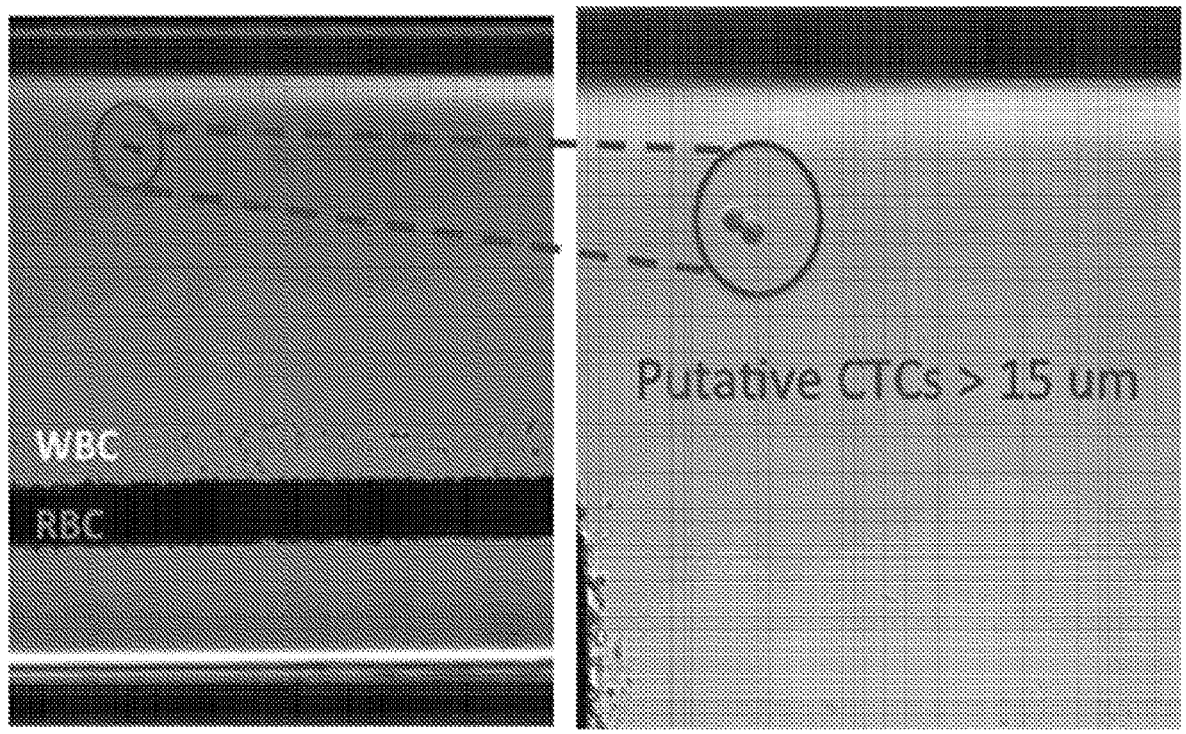
FIG. 52 shows the magnetic levitation profiling of blood samples from kidney cancer (renal cell carcinoma) patients.

FIG. 52 illustrates the magnetic levitation profiling of blood samples from kidney cancer (renal cell carcinoma) patients. Blood sample was diluted at 1:20 ratio in FBS and then levitated in 30 mM Gd+ solution. Cluster of CTCs (the circled region in both panels) were levitated above the band consisting of RBCs and WBCs.

The present invention has been described in terms of one or more preferred embodiments, and it should be appreciated that many equivalents, alternatives, variations, and modifications, aside from those expressly stated, are possible and within the scope of the invention.

What is claimed is:

1. A method of separating and collecting a heterogeneous population of cells, the method comprising:
   obtaining a microcapillary or microfluidic channel comprising two or more outlets;
   placing in the microcapillary or microfluidic channel the heterogeneous population of cells in a paramagnetic medium;
   separating the heterogeneous population of cells in the microcapillary or microfluidic channel based on differences in magnetic susceptibility and density of the heterogeneous population of cells; and
   withdrawing fluid comprising the separated cells from the two or more outlets using variable flow rates by microfluidic pumps at respective ones of the two or more outlets simultaneously to fractionalize the fluid comprising the separated cells across the two or more outlets by manipulation of the variable flow rates relative to one another.

2. The method according to claim 1 wherein the microcapillary or microfluidic channel is coupled to a single magnet for performing a step of levitating the heterogeneous population of cells in the microcapillary or microfluidic channel based on differences in magnetic susceptibility and density of the heterogeneous population of cells.

3. A method according to claim 2 wherein the cells are blood cells.

4. A method according to claim 3 wherein the heterogeneous population of cells include circulating tumor cells which are separated from the heterogeneous population of cells.

5. The method according to claim 1 wherein the heterogeneous population of cells comprises a blood sample with fetal cells and wherein fetal cells are separated from the blood sample in which the blood sample and a paramagnetic medium are placed in the microcapillary or microfluidic channel subjected to a magnetic field; the fetal cells are levitated within the microcapillary or microfluidic channel based on the magnetic susceptibility and density of the fetal cells; and the fetal cells are isolated using a levitation height threshold of the microcapillary or microfluidic channel.

6. A method according to claim 5 wherein the concentration of blood cells in the blood sample as provided to the microcapillary or microfluidic channel is 100,000/mL or lower.

7. A method according to claim 5 wherein the concentration of blood cells in the blood sample as provided to the microcapillary or microfluidic channel is from 0.8 to 25 million/mL.

8. A method according to claim 5 wherein the concentration of blood cells in the blood sample as provided to the microcapillary or microfluidic channel is from 50 to 250 million/mL.

9. A method according to claim 5 wherein the concentration of blood cells in the blood sample as provided to the microcapillary or microfluidic channel is from 1 to 5 million/mL.

10. A method according to claim 1 wherein the two or more outlets of the microcapillary or microfluidic channel include a top outlet and a bottom outlet.

11. A method according to claim 10 wherein a flow from the top outlet is greater than a flow from the bottom outlet.

12. A method according to claim 10 wherein a flow from the bottom outlet is greater than a flow from the top outlet.

13. A method according to claim 1 wherein the collected cells are from a blood sample.

14. A method according to claim 1 wherein the cells are collected from a saliva sample.

15. A method according to claim 1 wherein the cells are collected from a vaginal swab sample.

16. A method according to claim 1 wherein the cells are collected from an environmental sample.

17. A method according to claim 1 wherein the collected cells include cancer cells.

18. A method according to claim 1 wherein the cells are collected from a plasma sample.

19. A method according to claim 1 wherein the cells are collected from a serum sample.

\* \* \* \* \*